US008741648B2

(12) United States Patent
Rajesh et al.

(10) Patent No.: US 8,741,648 B2
(45) Date of Patent: Jun. 3, 2014

(54) REPROGRAMMING T CELLS AND HEMATOPOIETIC CELLS

(75) Inventors: Deepika Rajesh, Madison, WI (US); Amanda Mack, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 12 days.

(21) Appl. No.: 13/376,361

(22) PCT Filed: Jun. 4, 2010

(86) PCT No.: PCT/US2010/037376
§ 371 (c)(1),
(2), (4) Date: Feb. 16, 2012

(87) PCT Pub. No.: WO2010/141801
PCT Pub. Date: Dec. 9, 2010

(65) Prior Publication Data
US 2012/0135525 A1    May 31, 2012

Related U.S. Application Data

(60) Provisional application No. 61/184,546, filed on Jun. 5, 2009, provisional application No. 61/240,116, filed on Sep. 4, 2009.

(51) Int. Cl.
*C12N 5/071* (2010.01)
*C12N 15/85* (2006.01)
*C12N 15/86* (2006.01)
*C12N 5/02* (2006.01)

(52) U.S. Cl.
CPC ........ *C12N 5/0696* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2800/108* (2013.01)
USPC ............................ 435/455; 435/366; 435/377

(58) Field of Classification Search
CPC ...... C12N 5/0696; C12N 2501/603–2501/606; C12N 2800/108
See application file for complete search history.

(56) References Cited

U.S. PATENT DOCUMENTS

| | | | |
|---|---|---|---|
| 6,090,625 A | 7/2000 | Abuljadayel | |
| 2009/0191159 A1 | 7/2009 | Sakurada et al. | 424/93.7 |
| 2009/0252711 A1 | 10/2009 | Boquest et al. | 424/93.7 |
| 2010/0093090 A1 | 4/2010 | Deng et al. | 435/377 |
| 2011/0044961 A1 | 2/2011 | Giorgetti et al. | 424/93.21 |

FOREIGN PATENT DOCUMENTS

| | | |
|---|---|---|
| WO | WO 2009/032194 | 3/2009 |
| WO | WO 2009/157593 | 12/2009 |
| WO | WO 2011/032166 | 3/2011 |

OTHER PUBLICATIONS

Thomson et al. (PNAS, 92:7844-7848 (Aug. 1995).*
NIH (Stem Cells: Scientific Progress and Future Research Directions, Department of Health and Human Services, Chapter 1, pp. 1-4, Jun. 2001.*
Djuric and Ellis, 202, Stem Cell Research and Therapy, 2010,1:3, pp. 1-6.*
Maherali, Cell Stem Cell 3, Dec. 4, 2008,m pp. 595-605.*
Nagaoka M et al (2006) E-Cadherin-Coated Plates Maintain Pluripotent ES Cells without Colony Formation. PLoS One 1(1): e15, pp. 1-7.*
Meissner, Nature Biotechnology, 2007, 25:1177-1181.*
Aasen et al., "Efficient and rapid generation of induced pluripotent stem cells from human keratinocytes," *Nat. Biotechnol.*, 26(11):1276-1284, 2008.
Biswas et al., "Gene amplification by polymerase chain reaction for detection of *Ehrlichia risticii* DNA in Potomac horse fever," *Annals NY Acad Sci.*, 590:582-583, 1990.
Biswas, et al., "Diagnostic application of polymerase chain reaction for detection of *Ehrlichia risticii* in equine monocytic ehrlichiosis (Potomac horse fever)," *J. Clin. Microbiol.*, 29(10):2228-2233, 1991.
Bode et aL, "The hitchhiking principle: Optimizing episomal vectors for the use in gene therapy and biotechnology" *Gene Ther. Mol. Biol.*, 6:33-46, 2001.
Boland et al., "Adult mice generated from induced pluripotent stem cells," *Nature.* Aug 2, 2009. [Epub ahead of print].
Brown et al., "Reprogramming human peripheral blood cells," poster presented at International Society for Stem Cell Research, 7th Annual Conference, Barcelona, Spain, Jul. 8-11, 2009.
Choi et al., "Generation of mature human myelomonocytic cells through expansion and differentiation of pluripotent stem cell-derived lin⁻CD34⁺CD43⁺CD45⁺ progenitors," *The Journal of Clinical Investigation*, 119(9):2818-2829, 2009.
Chou et al., "Efficient human iPS cell derivation by a non-integrating plasmid from blood cells with unique epigenetic and gene expression signatures," *Cell Research*, 21:518-529, 2011.
Christ et al., "Improved purification of hematopoietic stem cells based on their elevated aldehyde dehydrogenase activity," *Haematologica*, 92(9):1165-1172, 2007.
Guo et al., "CD34⁻ hematopoietic stem cells: current concepts and controversies," *Stem Cells*, 21:15-20, 2003.
Hochedlinger et al., "Monoclonal mice generated by nuclear transfer from mature B and T donor cells," *Nature*, 415(28):1035-1038, 2002.
Hong et al., "Suppression of induced pluripotent stem cell generation by the p53-p21 pathway," *Nature*, 460:1132-1135, 2009.
Karanu et al., "Differential response of primitive human CD34⁻ and CD34⁺ hematopoietic cells to the Notch ligand Jagged-1," *Leukemia*, 17:1366-1374, 2003.
Kim et al.,"Genomic variation and segregation of equine infectious anemia virus during acute infection," *J. Virol.*, 66(6):3879-3882, 1992.
Kleeberger et al., "Viability and recovery of peripheral blood mononuclear cells cryopreserved for up to 12 years in a multicenter study," *Clin. Diagn. Lab Immunol.*, 6(1):14-19, 1999.

(Continued)

*Primary Examiner* — Valarie Bertoglio
(74) *Attorney, Agent, or Firm* — Parker Highlander PLLC

(57) ABSTRACT

Methods and compositions relating to the production of induced pluripotent stem cells (iPS cells) are disclosed. For example, induced pluripotent stem cells may be generated from CD34⁺ hematopoietic cells, such as human CD34⁺ blood progenitor cells, or T cells. Various iPS cell lines are also provided. In certain embodiments, the invention provides novel induced pluripotent stem cells with a genome comprising genetic rearrangement of T cell receptors.

16 Claims, 16 Drawing Sheets

(56) References Cited

OTHER PUBLICATIONS

Kunisato et al., "Direct generation of induced pluripotent stem cells from human non-mobilized blood," *Stem Cells Dev.*, 20(1):159-68, 2011.
Loh et al., "Generation of induced pluripotent stem cells from human blood," *Blood*, 113(22):5476-5479, 2009.
Loh et al., "Reprogramming of T cells from human peripheral blood," *Cell Stem Cell*, 7:15-19, 2010.
Maherali and Hochedlinger, "Guidelines and techniques for the generation of induced pluripotent stem cells," *Cell Stem Cell*, 3(6):595-605, 2008.
Office Communication issued in Chinese Patent Application No. 201080024535.2, dated Aug. 31, 2012. (English translation).
PCT International Search Report and Written Opinion issued in International application No. PCT/US2010/037376, dated Jan. 31, 2011.
PCT Invitation to Pay Additional Fees and Partial International Search Report issued in International application No. PCT/US2010/037376, dated Aug. 31, 2010.
Seki et al., "Generation of induced pluripotent stem cells from human terminally differentiated circulating T cells," *Cell Stem Cell*, 7:11-14, 2010.
Staerk et al., "Reprogramming of human peripheral blood cells to induced pluripotent stem cells," *Cell Stem Cell*, 7:20-24, 2010.
Takahashi et al., "Induction of pluripotent stem cells from adult human fibroblasts by defined factors ," *Cell*, 131(5):861-872, 2007.
Takahashi et al., "Induction of pluripotent stem cells from mouse embryonic and adult fibroblast cultures by defined factors," *Cell*, 126(4):663-676, 2006.
Vodyanik et al., "Leukosialin (CD43) defines hematopoietic progenitors in human embryonic stem cell differentiation cultures," *Blood*, 108(6):2095-105, 2006.
Yu et al., "Human induced pluripotent stem cells free of vector and transgene sequences," *Science*, 324(5928):797-801, 2009.
Yu et al., "Induced pluripotent stem cell lines derived from human somatic cells," *Science*, 318:1917-1920, 2007.
Zhou, et al., "Generation of induced pluripotent stem cells using recombinant proteins," *Cell Stem Cell*, 4(5):381-4, 2009.
Office Action issued in Chinese Application No. 201080024535.2, mailed May 30, 2013, and English language translation thereof.
Eminli, et. al., "Differentiation stage determines potential of hematopoetic cells for reprogramming into induced pluripotent stem cells," *Nature Genetic*, 41 968-976, 2009.
Extended European Search Report issued in European application No. 12177512.6, dated Jan. 21, 2013.
Office Action issued in Chinese Application No. 201080024535.2, mailed Feb. 4, 2013, and English language translation thereof.
Office Action issued in European Application No. 10728042.2, mailed Jan. 18, 2013.

\* cited by examiner

| Locus | Repeat # | TiPS L-1 | TiPS L-2 | Fib-iPS | Parent PBMC |
|---|---|---|---|---|---|
| D16S539 | 5, 8-15 | 11,12 | 11,12 | 10,13 | 11,12 |
| D7S820 | 6-14 | 8,10 | 8,10 | 9,12 | 8,10 |
| D13S317 | 7-15 | 8,12 | 8,12 | 11,13 | 8,12 |
| D5S818 | 7-15 | 12,13 | 12,13 | 12,13 | 12,13 |
| CSF1PO | 6-15 | 12,12 | 12,12 | 11,13 | 12,12 |
| TPOX | 6-13 | 9,11 | 9,11 | 8,9 | 9,11 |
| Amelogenin | NA | X,Y | X,Y | X,X | X,Y |
| TH01 | 5-11 | 7,9 | 7,9 | 8,9.3 | 7,9 |
| vWA | 11, 13-21 | 16,18 | 16,18 | 16,19 | 16,18 |
FIG. 7
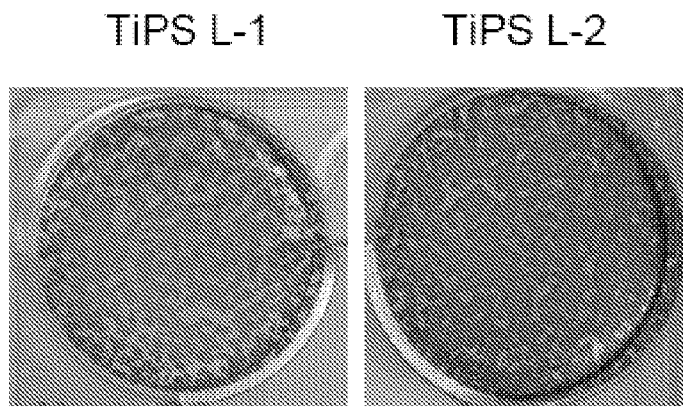
FIG. 8
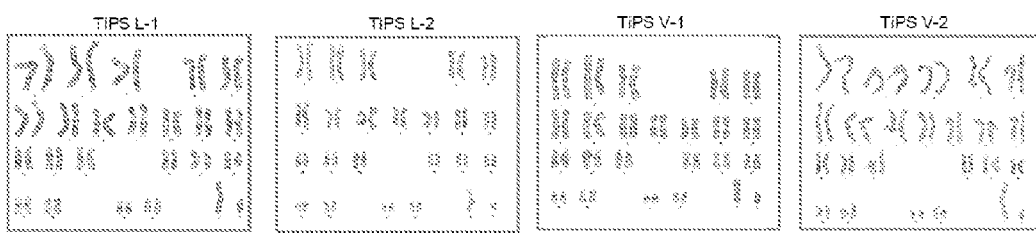
FIG. 9
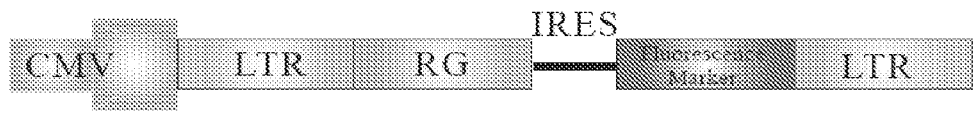
FIG. 10

US 8,741,648 B2

REPROGRAMMING T CELLS AND HEMATOPOIETIC CELLS

This application is a national phase application under 35 U.S.C. 371 of International Application No. PCT/US2010/037376, filed Jun. 4, 2010, which claims priority to U.S. Application No. 61/184,546 filed on Jun. 5, 2009 and U.S. Application No. 61/240,116 filed on Sep. 4, 2009, the entire disclosure of each of which are specifically incorporated herein by reference in its entirety without disclaimer.

BACKGROUND OF THE INVENTION

1. Field of the Invention

The present invention relates generally to the field of molecular biology and stem cells. More particularly, it concerns reprogramming of somatic cells, especially T cells and hematopoietic cells.

2. Description of Related Art

In general, stem cells are undifferentiated cells which can give rise to a succession of mature functional cells. For example, a hematopoietic stem cell may give rise to any of the different types of terminally differentiated blood cells. Embryonic stem (ES) cells are derived from the embryo and are pluripotent, thus possessing the capability of developing into any organ or tissue type or, at least potentially, into a complete embryo.

Induced pluripotent stem cells, commonly abbreviated as iPS cells or iPSCs, are a type of pluripotent stem cell artificially derived from a non-pluripotent cell, typically an adult somatic cell. Induced pluripotent stem cells are believed to be identical to natural pluripotent stem cells, such as embryonic stem cells in many respects, such as in terms of the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

IPS cells were first produced in 2006 (Takahashi et al., 2006) from mouse cells and in 2007 from human cells (Takahashi et al., 2007a; Yu et al, 2007). This has been cited as an important advancement in stem cell research, as it may allow researchers to obtain pluripotent stem cells, which are important in research and potentially have therapeutic uses, without the controversial use of embryos.

In humans, iPS cells are commonly generated from dermal fibroblasts. However, the requirement for skin biopsies and the need to expand fibroblast cells for several passages in vitro make it a cumbersome source for generating patient-specific stem cells. Moreover, previous methods for reprogramming of human somatic cells are inconvenient because they need to obtain somatic cells directly from a human subject, or maintain the cells in a labor-intensive cell culture system. Therefore, there is a need to develop methods to induce pluripotent stem cells from alternative sources which are simple, convenient, and easily accessible. In developing the present invention, the inventors considered that blood samples may be such a source because blood may be collected from a patient or a healthy individual, stored or transferred, for example, from a central unit for distribution to one or more remote places. However, there have been no reports in producing pluripotent stem cells from T cells from such a clinically accessible source until this application to the inventors' knowledge, demonstrating a substantial need to develop such technologies.

SUMMARY OF THE INVENTION

The present invention overcomes a major deficiency in the art in providing induced pluripotent stem cells derived from T cells and/or hematopoietic progenitor cells by reprogramming. The present methods could produce iPS cells from a clinically accessible source of T cells, such as a 3 ml whole blood sample, circumventing the need of mobilization of hematopoietic cells. In other embodiments, hematopoietic cells, such as human or mammalian CD34$^+$ CD45$^+$ CD43$^-$ hematopoietic precursor cells, may be obtained from a blood sample and converted to iPS cells. Hematopoietic precursor cells may be obtained from a blood sample of peripheral blood, e.g., via enrichment of CD34$^+$ cells or depletion of non-CD34$^+$ cell lineages. In certain embodiments, CD34$^+$ hematopoietic cells may be obtained from a blood sample, such as a refrigerated or cryopreserved blood sample, which was obtained without mobilizing CD34$^+$ hematopoietic progenitor cells in the subject prior to obtaining the blood sample. In this way, iPS cells may be generated from a wide variety of blood samples, including peripheral blood samples found at blood banks.

Therefore, there are provided methods for producing induced pluripotent stem cells from T cells and/or hematopoietic progenitor cells comprising the steps of: (a) obtaining a cell population comprising T cells and/or hematopoietic progenitor cells; and (b) producing iPS cells from T cells and/or hematopoietic progenitor cells of the cell population to provide an iPS cell population. Exemplary sources of the cell population may include, but are not limited to, blood samples, blood components, bone marrow, lymph node, fetal liver, or umbilical cord. The source of the cell population may comprise a blood sample or cells derived from a blood sample, wherein the blood sample was obtained from a subject without externally mobilizing hematopoietic progenitor cells in the subject (e.g., via external administration of a hematopoietic growth factor to the subject) prior to obtaining the blood sample.

The cell population may be obtained from a cryopreserved blood sample or the source of cell population or the cell population may have been cryopreseved. It was demonstrated that a crypreserved blood sample could be used as a source of T cells for successful reprogramming into iPS cells in the Examples.

A particular advantage of certain aspects of the present invention is the ability to practice certain aspects of the present invention through the use of a small volume of blood samples. The suitable volume of a blood sample could be from about 1 to about 5 ml, about 1 to 10 ml, about 1 to 15 ml, or more specifically, about 3 ml.

Hematopoietic stem/progenitor cells, like CD34$^+$ cells, may be induced with extrinsically applied G-CSF to mobilize into peripheral blood for enrichment in a peripheral blood source. It has been found in certain aspects of the present invention that peripheral blood cells from non-mobilized donors can achieve successful reprogramming, therefore mobilization of bone marrow cells by extrinsically applied growth factors are not needed. Thus, in a particular aspect, the source of the cell population may be a subject whose cells have not been mobilized with one or more extrinsically applied hematopoietic growth factors, e.g., granulocyte colony-stimulating factor (G-CSF). The term "extrinsic" or "external," as used interchangeably herein, refers to application of a mobilizing agent from outside the organism, in contrast to use of CD34$^+$ cells that have been mobilized to some degree by intrinsic factors that originate from within the organism.

To provide a population of T cells suitable for reprogramming, the cell population comprising T cells may be prepared under conditions that will activate the T cells in vitro, such as in the presence of an anti-CD3 antibody, or in vivo (and thus have a specific TCR for a particular antigen, e.g., a cancer antigen for melanoma such as GP-100). This may also include the use of tetramers, vaccines and/or in vitro peptide stimulations known in the art. The cell population may also be cultured in vitro with one or more cytokines (e.g., IL-2) to expand the T cell population therein. The T cells may be human T cells. In a particular aspect, the T cells may be $CD4^+$, $CD8^+$ T cells, or a combination thereof. Non-limiting examples of T cells include T helper 1 (TH1) cells, T helper 2 (TH2) cells, TH17 cells, cytotoxic T cells, regulatory T cells, natural killer T cells, naïve T cells, memory T cells, gamma delta T cells and any T cells.

In certain aspects, the cell population comprises from about 80% to about 99%, about 90% to about 99%, about 97% to about 99%, or any intermediate range of T cells, which may correspond to from at least, about, or at most, $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $2 \times 10^4$, $3 \times 10^4$, $4 \times 10^3$, $5 \times 10^4$, $6 \times 10^4$, $7 \times 10^4$, $8 \times 10^4$, $9 \times 10^4$, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$ T cells or any range derivable therein. For example, the inventors demonstrated reprogramming in 96 well plates with as little as approximately $1-5 \times 10^3$ T cells per well (FIGS. 6A-6B).

To provide a population of hematopoietic precursor cells, the cell population comprising hematopoietic cells may be prepared under conditions that will result in an enrichment or expansion of $CD34^+$ cells. Specifically, the invention finds that mobilization of bone marrow cells is not required for obtaining enough $CD34^+$ cells for reprogramming. For example, magnetic activated cell sorting (MACS) or fluorescence activated cell sorting (FACS) may be used to enrich $CD34^+$ hematopoietic cells; in certain embodiments, an Indirect CD34 MicroBead Kit or a Direct CD34 MicroBead Kit (both available from Miltenyi Biotec, Bergisch Gladbach, Germany) may be used with MACS to enrich $CD34^+$ hematopoietic cells from a sample, such as a peripheral blood sample. Additional methods are also known in the art for obtaining mobilized $CD34^+$ hematopoietic progenitor cells from peripheral blood, including the methods described in Gratwohl et al. (2002). Nonetheless, in certain preferred embodiments, the $CD34^+$ hematopoietic precursor cells may be obtained from a subject which has not been exposed to one or more hematopoietic growth factors; thus, the $CD34^+$ hematopoietic precursor cells may advantageously be obtained from a blood sample of a donor that has not been mobilized by one or more extrinsically applied growth factors, including blood samples typically found in blood banks In other embodiments, $CD34^+$ cells may be enriched in a sample via depletion of mature-hematopoietic cells, such as T cells, B cells, NK cells, dendritic cells, monocytes, granulocytes, and/or erythroid cells. For lineage depletion, the cell suspension may be incubated with a cocktail of antibodies (e.g., one or more of CD2, CD3, CD11b, CD14, CD15, CD16, CD19, CD56, CD123, CD235a) which may then be used to remove the above mentioned lineage positive cells (e.g., Karanu et al., 2003). The Lineage cell Depletion Kit (Miltenyi Biotec, Bergisch Gladbach, Germany) is also commercially available and may be used for this purpose. In certain embodiments, a combination of SCF, Flt3L, and/or IL-3 cytokines may be used to expand and proliferate $CD34^+$ cells prior to conversion to iPS cells, e.g., using the method described in Akkina et al. (1996) or StemPro™-34 media (available from Invitrogen, Carlsbad, Calif., USA).

It is anticipated by the inventors that virtually any hematopoietic progenitor cell or $CD34^+$ hematopoietic cell may be reprogrammed into an iPS cell via the methods described herein. In certain embodiments, hematopoietic precursor cells obtained or derived from a peripheral blood sample may be converted into iPS cells via the methods provided herein. The hematopoietic precursor cells may express both CD34 and CD45, or CD34, CD45, and CD43. In certain instances it may be desirable to generate hematopoietic precursors from stem cells such as human embryonic stem cells (hESC); in these embodiments, $CD34^+$ $CD43^+$ $CD45^+$ hematopoietic cells highly enriched in myeloid progenitors may be generated, e.g., by coculture of hESC with OP9 feeder cells as described in Choi et al. (2009). In certain instances the hematopoietic precursor cells may be negative for CD34 (e.g., Guo et al., 2003); it is anticipated that these hematopoietic precursor cells may nonetheless be differentiated into iPS cells.

To produce iPS cells from T cells and/or hematopoietic progenitor cells of the cell population, the methods may comprise introducing one or more reprogramming factors into the T cells and/or hematopoietic progenitor cells. In a certain aspect, the reprogramming factors may be reprogramming proteins comprising a Sox family protein and an Oct family protein, one or more or each of which may be operatively linked to a protein transduction domain for cellular entry. In a further embodiment of the invention, the reprogramming factors may be encoded by one or more expression cassettes, and may include, for example, a Sox family protein and an Oct family protein. Sox and Oct are thought to be central to the transcriptional regulatory hierarchy that specifies ES cell identity. For example, Sox may be Sox1, Sox2, Sox3, Sox15, or Sox18, particularly Sox2; Oct may be Oct4. Additional factors may increase the reprogramming efficiency, like Nanog, Lin28, Klf4, c-Myc, SV40 Large T antigen, or Esrrb; specific sets of reprogramming factors may be a set comprising Sox2, Oct4, Nanog and, optionally, Lin-28; or comprising Sox2, Oct4, Klf and, optionally, c-Myc.

In a particular embodiment, the one or more expression cassettes may comprise one or more polycistronic transcription units. The polycistronic unit may comprise different combination of operably linked coding regions, for example, (i) at least two reprogramming genes, such as Sox-Oct, c-Myc-Klf, or Nanog-Lin28; alternatively, (ii) a reprogramming gene linked with a selectable or screenable marker. The aspect (i) may be preferred because the inventors have found that by switching to using bicistronic vectors that have two of the reprogramming factors per vector (Sox2 and Oct4, cMyc and Klf4, or Nanog and Lin28) without any fluorescent marker (vector maps are represented in FIGS. 11A-11C) instead of using four separate bicistronic vectors with one reprogramming factor and a fluorescent marker (such a vector map is represented in FIG. 10), the reprogramming efficiency of using these former vectors have improved dramatically and the iPS colonies come up earlier (~day 10-14 rather than day 20-24).

To co-express multiple gene in the same polycistronic transcription unit, the polycistronic transcription unit may comprise an internal ribosome entry site (IRES) or a sequence coding for at least one protease cleavage site and/or self-cleaving peptide for polycistronic transcription. For example, the self-cleaving peptide is a viral 2A peptide.

In a still further embodiment, the one or more expression cassettes are comprised in a reprogramming vector selected from the group consisting of a viral vector, an episomal vector, or a transposon. More specifically, the vector may be a retroviral vector, such as murine leukemia virus (MLV), Moloney murine leukemia virus (MMLV), Akv-MLV, SL-3-3-MLV or another closely related virus. The viral vector could also be a lentiviral vector. In certain aspects, the transcriptional regulatory element may comprise a long terminal repeat region (LTR) to mediate integration of viral genes.

In an alternative aspect, the vector may be an episomal vector, such as an EBV-based vector, or a transposon-based vector.

In a further embodiment, the reprogramming factors may be introduced by liposome transfection, nucleofection, electroporation, particle bombardment, calcium phosphate, polycation, or polyanion, or any methods suitable for introducing exogenous elements into the cells.

In some further aspects, the iPS cells could be selected based on one or more embryonic stem cell characteristics, such as an undifferentiated morphology, an embryonic stem cell-specific marker, an adherent property, pluripotency, multi-lineage differentiation potential or any characteristics known in the art. For example, it may be particularly convenient to select the progeny cells on the basis of the undifferentiated morphology. The embryonic stem cell-specific marker could be one or more specific markers selected from the group consisting of SSEA-3, SSEA-4, Tra-1-60 or Tra-1-81, Tra-2-49/6E, GDF3, REX1, FGF4, ESG1, DPPA2, DPPA4, and hTERT. This selection step may be employed at more than one time points after reprogramming to ensure that cells are in a pluripotent state and does not return to a differentiated state. IPS cells are also different from the T cells and hematopoietic progenitor cells in their adherent property to a surface, which could also be employed in a convenient separation method.

In a particular aspect, the iPS cells may be selected based on essentially no expression of introduced exogenous elements such as vector genetic elements or reporter genes comprised in the expression cassettes, because a reprogrammed cell is able to silence exogenously introduced material as a cell has become pluripotent. Therefore, an essential loss of integrating vector genetic elements, or reporter expression, e.g., fluorescence, is an indication in addition to morphological characteristics that cell has been reprogrammed. For example, the silence of reporter expression may be selected by fluorescence-activated cell sorting (FACS), CAT assay or luminescence assay based on the reporter gene introduced. "Essential loss" or "essentially free" of exogenous elements means that less than 1%, 0.5%, 0.1%, 0.05%, or any intermediate percentage of cells of an iPS cell population comprises exogenous elements. The iPS cell population may be essentially free of integrated, exogenous viral elements.

For clinical application of the iPS cells, the methods may further comprise differentiating the iPS cells to a differentiated cell, for example, a cardiomyocyte, a hematopoietic cell, a myocyte, a neuron, a fibroblast, a pancreatic cell, a hepatocyte, or an epidermal cell. In a further aspect, a differentiated cell, tissue or organ, which has been differentiated from the iPS cell population as described above may be disclosed. The tissue may comprise nerve, bone, gut, epithelium, muscle, cartilage or cardiac tissue; the organ may comprise brain, spinal cord, heart, liver, kidney, stomach, intestine or pancreas. In certain aspects, the differentiated cell, tissue or organ may be used in tissue transplantation, drug screen or developmental research to replace embryonic stem cells.

In a still further aspect, an induced pluripotent stem cell produced according to the methods above may also be disclosed. There may also be provided an induced pluripotent stem cell comprising a genome comprising an incomplete set of V, D, and J segments of T cell receptor genes compared with an embryonic stem cell, which may be a human cell. In a particular aspect, the induced pluripotent stem cell may be essentially free of integrated, exogenous viral elements.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) Flow cytometric analysis of input cell source CD3 surface expression. (i) CD3 surface expression on day −3 non-activated PBMCs and day 0 activated T-cells from the PBMC population in a representative donor. (ii) CD3 expression gated on the transduced (GFP$^+$) cell population 72 hours post-transduction in a representative donor to demonstrate preferential transduction of CD3$^+$ cells. (iii) Histogram representation of the above metrics (i-ii) in an average of 10 donor Vacutainer-derived samples. (FIG. 2B) Flow cytometric analysis of hESC pluripotency markers OCT4, Tra-1-81, SSEA-3 and SSEA-4 in representative leukapheresis ("TiPS L-2") and Vacutainer© ("TiPS V-1") derived TiPS lines. (FIG. 2C) T-cell receptor (TCR) β chain rearrangement analysis using multiplexed PCR primers targeted to conserved regions within the V-J region of the TCR β locus. Polyclonal starting T-cell populations are represented by a bell-shaped curve of amplicon peaks within the valid fragment size range on the electropherogram. Fibroblast (non-T-cell) iPS cells ("Fib-iPS") lack germline rearrangement at the TCR β locus and serve as a negative control. The clonally derived TiPS lines (representative data from two leukapheresis lines and one Vacutainer© line, "TiPS L-1", "TiPS L-2" and "TiPS V-2", respectively) show one distinct peak of defined size. DNA fragment analysis was performed on an ABI 3730 DNA analyzer.

(FIG. 3A) RT-PCR analysis of representative leukapheresis ("TiPS L-1 and L-2") and Vacutainer© ("TiPS V-2") derived TiPS cell lines for expression of hES cell-marker genes DNMT38, LEFTB, NODAL, REX1, ESG1, TERT, GDF3, and UTF1. GAPDH was used as positive loading control for each sample. (FIG. 3B) PCR analysis of genomic DNA confirms integration of the transgenes. Forward primers for the reprogramming gene ("RG") of interest and reverse primers for the IRES were utilized. OCT4 forward and reverse primers were used as the PCR reaction positive control, as shown in vector map. (FIG. 3C) RT-PCR analysis of TiPS cell lines shows silencing of the exogenous transgenes, with GAPDH as positive control for each sample. hESC line H1 and a fibroblast derived iPSC line (Fib-iPS) served as positive cell controls, and activated donor T-cells served as a negative cell control. (FIG. 3D) TiPS clones expressed human embryonic stem cell-specific pluripotency markers as shown by flow cytometry analysis.

(FIG. 4A) Teratoma formation shows in vivo differentiation potential. TiPS cells injected into SCID/beige mice formed teratomas at 5 to 12 weeks. Hematoxylin and eosin staining shows tissues consistent with derivation from the three primary germ layers including simple epithelium with goblet cells indicating gastrointestinal or respiratory tissue (endoderm), cartilage (mesoderm) and retinal pigmented epithelium (ectoderm). Representative images from TiPS L-2 cell line were acquired using an Olympus IX71 microscope using a 40× objective. (FIG. 4B) In vitro differentiation into neurons. TiPS L-2 cells were induced into neuronal differentiation as aggregates then stained for neuronal marker beta III-tubulin with an Alexa Fluor 594 secondary antibody; cell nuclei were counterstained with Hoechst stain. Images were acquired using a 20× objective. Contrast was adjusted and images were merged using Image J software. (FIG. 4C) Cardiac induction of TiPS cells via cell aggregate method. Cell aggregates contain beating cardiac troponin T (cTNT)-positive cardiomyocytes at day 14 to 15. Flow data from representative samples is shown. Images were acquired using a 10× objective. (FIG. 4D) In vitro differentiation into hematopoietic progenitor cells. Hematopoietic progenitor cells (HPCs) generated via a serum-free embryoid body (EB) differentiation protocol for 12 days in two TiPS lines compared to an hESC line (H1) and a fibroblast derived iPSC line (Fib-iPS). HPCs were quantified via flow cytometry by dissociating the EBs into single cells and staining with fluorochrome-conjugated monoclonal antibodies to CD34, CD45, CD43, CD31, CD41 and CD235a. (FIG. 4E) Hematopoietic clonogenic (CFU) assays were performed by placing EB differentiated and individualized cells into serum-free MethoCult media containing cytokines (SCF, G-CSF, GM-CSF, IL-3, IL-6, and EPO). Colonies were scored after 14 days of incubation according to morphologic criteria as erythroid (CFU-E/BFU-E), macrophage (CFU-M, data not shown), granulocyte (CFU-G, data not shown), granulocyte-macrophage (CFU-GM), and granulocyte-erythroid-macrophage-megakaryocyte (CFU-GEMM). Total CFU count is also denoted (CFU). Images were acquired using an Olympus CKX41 microscope with a 2× objective.

FIG. 6A. Donor A' T cells are infected with bicistronic vectors SO (Sox2 and Oct4) and CK (c-Myc and Klf4) and plated on MEFs. Live cell anti-Tra1-60 labeling was conducted to detect iPS cell colonies. FIG. 6B. Donor A' T cells are infected with bicistronic vecotors SO (Sox2 and Oct4) and NL (Nanog and Lin28) and plated on MEFs. Live cell anti-Tra1-60 labeling was conducted to detect iPS cell colonies. Input cell number was shown as "Input #" to indicate the number of T cells in the starting material.

FIG. 7. DNA fingerprinting. Short Tandem Repeat (STR) analysis shows TiPS cell lines are identical to parent activated T-cells for all 15 allelic polymorphisms detected across the 8 STR loci analyzed. Representative data from two TiPS lines (TiPS L-1 and TiPS L-2) is shown.

FIG. 8. Alkaline phosphatase (AP) staining. TiPS lines TiPS L-1 and TiPS L-2 are AP positive. Images were acquired on an HP Scanjet G3110 computer scanner.

FIG. 9. TiPS cell lines display normal karyotype. TiPS cell lines "TiPS L-1" and "TiPS L-2" were grown for 6 passages on MEFs, and lines "TiPS V-1" and "TiPS V-2" were grown on Matrigel for 8 of 18 total passages and 30 of 34 total passages, respectively. Cells were subjected to G banding analysis and no clonal abnormalities were detected.

FIG. 10. Vector map of the MMLV retroviral construct used for reprogramming experiments. "RG" denotes reprogramming gene.

FIG. 11A. Vector map of MMLV-Oct4-IRES-Sox2 (abbreviated as "Oct4-Sox2"). FIG. 11B. Vector map of MMLV-cMyc-IRES-Klf4 (abbreviated as "cMyc-Klf4"). FIG. 11C. Vector map of MMLV-Nanog-IRES-Lin28 (abbreviated as "Nanog-Lin28").

DESCRIPTION OF ILLUSTRATIVE EMBODIMENTS

I. Introduction

Figure 1:
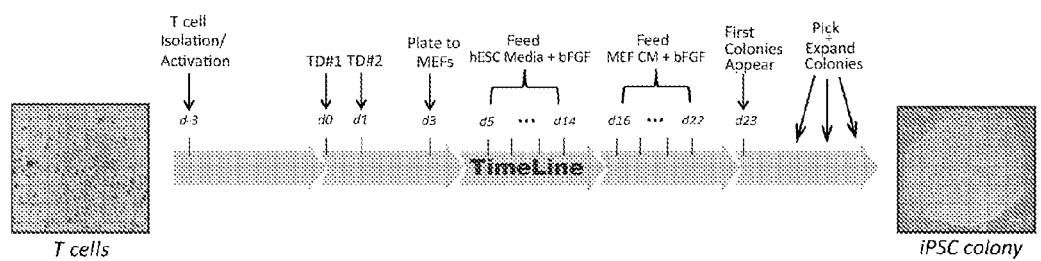
FIG. 1: Overview of T-cell reprogramming process, beginning with activated T-cells and resulting in iPSC colonies with hESC-like morphology. T-cell and iPSC colony images were acquired on an Olympus IX71 microscope with 10× and 20× objectives, respectively.

In vitro reprogramming of somatic cells to an undifferentiated pluripotent state by viral transfer of defined factors such as SOX2, OCT4, NANOG and LIN28 or SOX2, OCT4, c-Myc, and KLF4 (Yu et al., 2007; Takahashi et al., 2007b) has opened the way for the generation of patient-specific human iPSCs using multiple cell types (Loh et al., 2009; Aasen et al., 2008) This premise has been further advanced by derivation of iPSCs via transient expression of genes or by using protein transduction of appropriate transcription factors (Yu et al., 2009; Zhou et al., 2009). To date, the majority of iPSC research in humans has focused on fibroblasts as a cell source. While fibroblasts offer certain advantages as a starting material due to their commercial availability and ease of gene delivery, they are suboptimal for large-scale clinical derivation of iPSC lines due to the need for invasive skin biopsies and the difficulty of establishing stable lines from primary tissue. Non-mobilized peripheral blood is perhaps the ideal cell source for reprogramming due to the ease of obtaining patient samples (Maherali and Hochedlinger, 2008). Additionally, large numbers of frozen blood samples, from living and deceased donors, are stored in biorepositories worldwide (Kleeberger et al., 1999).

The instant invention overcomes several major problems with current reprogramming technologies by generating induced pluripotent stem cells from T cells and/or hematopoietic precursor cells. As discovered by the present invention, more abundant and tractable blood cell source the derivation of iPSCs from T lymphocytes could be obtained from the equivalent of 1 ml whole blood. These T-cell derived iPSCs ("TiPS") share essential characteristics with hESCs as well as fibroblast-derived iPSC lines. Additionally, they retain their characteristic T-cell receptor (TCR) gene rearrangements, a property which could be exploited, for example, as a genetic tracking marker or in re-differentiation experiments to study human T-cell development.

Prior to the present invention, the inventors had significant uncertainties about the likelihood that reprogramming T cells or hematopoietic progenitor cells would be successful for several reasons. First, it was uncertain that whether T cells and/or hematopoietic precursor cells in blood samples would be present in sufficient quantities for reprogramming. Second, the possible effect of gene loss from V(D)J recombination of T-cell receptor genes in reprogramming had not been studied. Third, most of the cell types that have been reprogrammed so far are adherent cell types. T cells are non-adherent and are cultured in suspension. It had not been clear until this invention that T cells undergone reprogramming could make the transition to an adherent culture condition suitable for adherent iPS cells. Thus, methods of the present invention have been the first to enable generation of iPS cells from T cells or hematopoietic precursor cells. The T cells can be easily obtained from various sources, such as a small volume of blood sample. Similarly, hematopoietic precursor cells, such as (CD34$^+$/CD43$^-$/CD45$^+$/CD38$^-$) or (CD34$^-$, CD133$^+$/CD38$^-$) hematopoietic precursor cells, may be enriched from a peripheral blood sample.

A particular advantage of the present invention lies in rearranged and reduced V, D, J gene segments of T-cell receptors which may be retained in reprogrammed progeny cells. This serves as a specific characteristic or "bar code" of different clonal populations of T cell-derived iPS cells, and also help differentiates those iPS cells from pluripotent stem cells which have not undergone V(D)J recombination. In addition, the difference in adherent property between T cells and iPS cells make an advantage in automatic separation. Similarly, differences in adherent properties between hematopoietic precursor cells and iPS cells may be utilized for separation. By transferring reprogrammed T cells or hematopoietic progenitor cells to a culture condition suitable for adherence, such as placing irradiated mouse embryonic fibroblasts (MEFs) on the bottom of the culture vessel for T cells, iPS cells which are derived from the T cells or hematopoietic progenitor cells could adhere to the bottom while the T cells and/or hematopoietic progenitor cells remain in suspension. Further embodiments and advantages of the invention are described below.

II. Definitions

"Reprogramming" is a process that confers on a cell a measurably increased capacity to form progeny of at least one new cell type, either in culture or in vivo, than it would have under the same conditions without reprogramming. More specifically, reprogramming is a process that confers on a somatic cell a pluripotent potential. This means that after sufficient proliferation, a measurable proportion of progeny having phenotypic characteristics of the new cell type if essentially no such progeny could form before reprogramming; otherwise, the proportion having characteristics of the new cell type is measurably more than before reprogramming. Under certain conditions, the proportion of progeny with characteristics of the new cell type may be at least about 1%, 5%, 25% or more in the in order of increasing preference.

An "activator" of a T cell or a condition that will activate a T cell refers to a stimulus that activates T cells and include antigens, which may be presented on antigen presenting cells or on other surfaces; polyclonal activators, which bind to many T cell receptor (TCR) complexes regardless of specificity, and include lectins, e.g., concanavalin-A (Con-A) and phytohemagglutinin (PHA) and agents such as antibodies that bind specifically to invariant framework epitopes on TCR or CD3 proteins; and superantigens, which stimulate a significant number of T cells, and include, e.g., enterotoxins, such as *Staphyloccal* enterotoxins.

The terms "T lymphocyte" and "T cell" are used interchangeably, and refer to a cell that expresses a T cell antigen receptor (TCR) capable of recognizing antigen when displayed on the surface of antigen presenting cells or matrix together with one or more MHC molecules or, one or more non-classical MHC molecules.

"CD4$^+$ T cells" refers to a subset of T cells that express CD4 on their surface and are associated with cell-mediated immune response. They are characterized by the secretion profiles following stimulation, which may include secretion of cytokines such as IFN-gamma, TNF-alpha, IL-2, IL-4 and IL-10. "CD4" are 55-kD glycoproteins originally defined as differentiation antigens on T-lymphocytes, but also found on other cells including monocytes/macrophages. CD4 antigens are members of the immunoglobulin supergene family and are implicated as associative recognition elements in MHC (major histocompatibilit+y complex) class II-restricted immune responses. On T-lymphocytes they define the helper/inducer subset.

"CD8$^+$ T cells" refers to a subset of T cells which express CD8 on their surface, are MHC class I-restricted, and function as cytotoxic T cells. "CD8" molecules are differentiation antigens found on thymocytes and on cytotoxic and suppressor T-lymphocytes. CD8 antigens are members of the immunoglobulin supergene family and are associative recognition elements in major histocompatibility complex class I-restricted interactions.

"Hematopoietic progenitor cells" or "hematopoietic precursor cells" refers to cells which are committed to a hematopoietic lineage but are capable of further hematopoietic differentiation and include hematopoietic stem cells, multipotential hematopoietic stem cells (hematoblasts), myeloid progenitors, megakaryocyte progenitors, erythrocyte progenitors, and lymphoid progenitors. Hematopoietic stem cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T-cells, B-cells, NK-cells). The hematopoietic progenitor cells may express CD34. The hematopoietic progenitor cells may co-express CD133 and be negative for CD38 expression. In certain embodiments, certain human hematopoietic may not express CD34, but these cells may nonetheless be converted into iPS cells via the methods disclosed herein. Hematopoietic precursor cells include CD34$^+$/CD45$^+$ hematopoietic precursor cells and CD34$^+$/CD45$^+$/CD43$^+$ hematopoietic precursor cells. The CD34$^+$/CD43$^-$/CD45$^-$ hematopoietic precursor cells may be highly enriched for myeloid progenitors. Various lineages of hematopoietic cells, such as $CD34^+/CD43^+/CD45^+$ hematopoietic precursor cells, may be converted to iPS cells via the methods disclosed herein. Hematopoietic cells also include various subsets of primitive hematopoietic cells including: $CD34^-/CD133^+/CD38^-$ (primitive hematopoietic precursor cells), CD43(+) CD235a(+)CD41a(+/−) (erythro-megakaryopoietic), lin(−) CD34(+)CD43(+)CD45(−) (multipotent), and lin(−)CD34 (+)CD43(+)CD45(+) (myeloid-skewed) cells, CD133+/ ALDH+ (aldehydehehydrogenase) (e.g., Hess et al. 2004; Christ et al., 2007). It is anticipated that any of these primitive hematopoietic cell types or hematopoietic precursor cells may be converted into iPS cells as described herein.

A "vector" or "construct" (sometimes referred to as gene delivery or gene transfer "vehicle") refers to a macromolecule or complex of molecules comprising a polynucleotide to be delivered to a host cell, either in vitro or in vivo. A vector can be a linear or a circular molecule.

A "plasmid", a common type of a vector, is an extra-chromosomal DNA molecule separate from the chromosomal DNA which is capable of replicating independently of the chromosomal DNA. In certain cases, it is circular and double-stranded.

By "expression construct" or "expression cassette" is meant a nucleic acid molecule that is capable of directing transcription. An expression construct includes, at the least, a promoter or a structure functionally equivalent to a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "cell" is herein used in its broadest sense in the art and refers to a living body which is a structural unit of tissue of a multicellular organism, is surrounded by a membrane structure which isolates it from the outside, has the capability of self replicating, and has genetic information and a mechanism for expressing it. Cells used herein may be naturally-occurring cells or artificially modified cells (e.g., fusion cells, genetically modified cells, etc.).

As used herein, the term "stem cell" refers to a cell capable of self replication and pluripotency. Typically, stem cells can regenerate an injured tissue. Stem cells herein may be, but are not limited to, embryonic stem (ES) cells or tissue stem cells (also called tissue-specific stem cell, or somatic stem cell). Any artificially produced cell which can have the above-described abilities (e.g., fusion cells, reprogrammed cells, or the like used herein) may be a stem cell.

"Embryonic stem (ES) cells" are pluripotent stem cells derived from early embryos. An ES cell was first established in 1981, which has also been applied to production of knock-out mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing certain factors, referred to as reprogramming factors.

"Pluripotency" refers to a stem cell that has the potential to differentiate into all cells constituting one or more tissues or organs, or particularly, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, direct descendants of totipotent cells or induced pluripotent cells.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is particularly chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, particularly at least about 90%, and most particularly at least about 95% of the nucleotides, or amino acids, respectively match over a defined length of the molecules, as determined using the methods above.

III. General Background for Stem Cells

In certain embodiments of the invention, there are disclosed methods of reprogramming somatic cells, especially T cell, by introducing reprogramming factors into somatic cells. The progeny of these cells could be identical to embryonic stem cells in various aspects as described below, but essentially free of exogenous genetic elements. Understanding of embryonic stem cell characteristics could help select induced pluripotent stem cells. Reprogramming factors known from stem cell reprogramming studies could be used for these novel methods. It is further contemplated that these induced pluripotent stem cells could be potentially used to replace embryonic stem cells for therapeutics and research applications due to the ethics hurdle to use the latter.

A. Stem Cells

Stem cells are cells found in most, if not all, multi-cellular organisms. They are characterized by the ability to renew themselves through mitotic cell division and differentiating into a diverse range of specialized cell types. The two broad types of mammalian stem cells are: embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues.

As stem cells can be grown and transformed into specialized cells with characteristics consistent with cells of various tissues such as muscles or nerves through cell culture, their use in medical therapies has been proposed. In particular, embryonic cell lines, autologous embryonic stem cells generated through therapeutic cloning, and highly plastic adult stem cells from the umbilical cord blood or bone marrow are touted as promising candidates. Most recently, the reprogramming of adult cells into induced pluripotent stem cells has enormous potential for replacing embryonic stem cells.

B. Embryonic Stem Cells

Embryonic stem cell lines (ES cell lines) are cultures of cells derived from the epiblast tissue of the inner cell mass (ICM) of a blastocyst or earlier morula stage embryos. A blastocyst is an early stage embryo—approximately four to five days old in humans and consisting of 50-150 cells. ES cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta.

Nearly all research to date has taken place using mouse embryonic stem cells (mES) or human embryonic stem cells (hES). Both have the essential stem cell characteristics, yet they require very different environments in order to maintain an undifferentiated state. Mouse ES cells may be grown on a layer of gelatin and require the presence of Leukemia Inhibitory Factor (LIF). Human ES cells could be grown on a feeder layer of mouse embryonic fibroblasts (MEFs) and often require the presence of basic Fibroblast Growth Factor (bFGF or FGF-2). Without optimal culture conditions or genetic manipulation (Chambers et al., 2003), embryonic stem cells will rapidly differentiate.

A human embryonic stem cell may be also defined by the presence of several transcription factors and cell surface proteins. The transcription factors Oct4, Nanog, and Sox2 form the core regulatory network that ensures the suppression of genes that lead to differentiation and the maintenance of pluripotency (Boyer et al., 2005). The cell surface antigens most commonly used to identify hES cells include the glycolipids SSEA3 and SSEA4 and the keratan sulfate antigens Tra-1-60 and Tra-1-81.

After twenty years of research, there are no approved treatments or human trials using embryonic stem cells. ES cells, being pluripotent cells, require specific signals for correct differentiation—if injected directly into the body, ES cells will differentiate into many different types of cells, causing a teratoma. Differentiating ES cells into usable cells while avoiding transplant rejection are just a few of the hurdles that embryonic stem cell researchers still face. Many nations currently have moratoria on either ES cell research or the production of new ES cell lines. Because of their combined abilities of unlimited expansion and pluripotency, embryonic stem cells remain a theoretically potential source for regenerative medicine and tissue replacement after injury or disease. However, one way to circumvent these issues is to induce pluripotent status in somatic cells by direct reprogramming.

IV. Reprogramming Factors

The generation of iPS cells is crucial on the reprogramming factors used for the induction. The following factors or combination thereof could be used in the methods disclosed in the present invention. In certain aspects, nucleic acids encoding Sox and Oct (particularly Oct3/4) will be included into the reprogramming vector. For example, one or more reprogramming vectors may comprise expression cassettes encoding Sox2, Oct4, Nanog and optionally Lin28, or expression cassettes encoding Sox2, Oct4, Klf4 and optionally c-Myc, or expression cassettes encoding Sox2, Oct4, and optionally Esrrb, or expression cassettes encoding Sox2, Oct4, Nanog, Lin28, Klf4, c-Myc, and optionally SV40 Large T antigen. Nucleic acids encoding these reprogramming factors may be comprised in the same expression cassette, different expression cassettes, the same reprogramming vector, or different reprogramming vectors.

Oct4 and certain members of the Sox gene family (Sox1, Sox2, Sox3, and Sox15) have been identified as crucial transcriptional regulators involved in the induction process whose absence makes induction impossible. Additional genes, however, including certain members of the Klf family (Klf1, Klf2, Klf4, and Klf5), the Myc family (c-Myc, L-Myc, and N-Myc), Nanog, and Lin28, have been identified to increase the induction efficiency.

Oct4 (Pou5f1) is one of the family of octamer ("Oct") transcription factors, and plays a crucial role in maintaining pluripotency. The absence of Oct4 in Oct4⁻ cells, such as blastomeres and embryonic stem cells, leads to spontaneous trophoblast differentiation, and presence of Oct4 thus gives rise to the pluripotency and differentiation potential of embryonic stem cells. Various other genes in the "Oct" family, including Oct4's close relatives, Oct1 and Oct6, fail to elicit induction, thus demonstrating the exclusiveness of Oct-4 to the induction process.

The Sox family of genes is associated with maintaining pluripotency similar to Oct4, although it is associated with multipotent and unipotent stem cells in contrast with Oct4, which is exclusively expressed in pluripotent stem cells. While Sox2 was the initial gene used for reprogramming induction, other genes in the Sox family have been found to work as well in the induction process. Sox1 yields iPS cells with a similar efficiency as Sox2, and genes Sox3, Sox15, and Sox18 also generate iPS cells, although with decreased efficiency.

In embryonic stem cells, Nanog, along with Oct4 and Sox2, is necessary in promoting pluripotency. Therefore, it was surprising when Yamanaka et al. reported that Nanog was unnecessary for induction although Thomson et al. has reported it is possible to generate iPS cells with Nanog as one of the factors.

Lin28 is an mRNA binding protein expressed in embryonic stem cells and embryonic carcinoma cells associated with differentiation and proliferation. Thomson et al. demonstrated it is a factor in iPS generation, although it is unnecessary.

Klf4 of the Klf family of genes was initially identified by Yamanaka et al. and confirmed by Jaenisch et al. as a factor for the generation of mouse iPS cells and was demonstrated by Yamanaka et al. as a factor for generation of human iPS cells. However, Thompson et al. reported that Klf4 was unnecessary for generation of human iPS cells and in fact failed to generate human iPS cells. Klf2 and Klf4 were found to be factors capable of generating iPS cells, and related genes Klf1 and Klf5 did as well, although with reduced efficiency.

The Myc family of genes are proto-oncogenes implicated in cancer. Yamanaka et al. and Jaenisch et al. demonstrated that c-Myc is a factor implicated in the generation of mouse iPS cells and Yamanaka et al. demonstrated it was a factor implicated in the generation of human iPS cells. However, Thomson et al. and Yamanaka et al. reported that c-Myc was unnecessary for generation of human iPS cells. Usage of the "Myc" family of genes in induction of iPS cells is troubling for the eventuality of iPS cells as clinical therapies, as 25% of mice transplanted with c-Myc-induced iPS cells developed lethal teratomas. N-Myc and L-Myc have been identified to induce in the stead of c-myc with similar efficiency. SV40 large antigen may be used to reduce or prevent the cytotoxcity which may occur when c-Myc is expressed.

The reprogramming proteins used in the present invention can be substituted by protein homologs with about the same reprogramming functions. Nucleic acids encoding those homologs could also be used for reprogramming. Conservative amino acid substitutions are preferred—that is, for example, aspartic-glutamic as polar acidic amino acids; lysine/arginine/histidine as polar basic amino acids; leucine/isoleucine/methionine/valine/alanine/glycine/proline as nonpolar or hydrophobic amino acids; serine/threonine as polar or uncharged hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide.

V. Reprogramming of T Cells and/or Hematopoietic Precursor Cells

To provide iPS cells from alternative sources in addition to dermal fibroblasts commonly used in the current art, methods for reprogramming a cell population comprising T cells are provided. In certain embodiments, T cells are activated and expanded to provide a significant number of T cells for reprogramming.

A. T Cells

The term "T cell" refers to T lymphocytes as defined in the art and is intended to include thymocytes, immature T lymphocytes, mature T lymphocytes, resting T lymphocytes, or activated T lymphocytes. The T cells can be CD4⁺ T cells, CD8⁺ T cells, CD4⁺CD8⁺ T cells, or CD4⁻CD8⁻ cells. The T cells can also be T helper cells, such as T helper 1 (TH1), or T helper 2 (TH2) cells, or TH17 cells, as well as cytotoxic T cells, regulatory T cells, natural killer T cells, naïve T cells, memory T cells, or gamma delta T cells (Wilson et al., 2009; Wynn, 2005; Ladi et al., 2006). T cells that differ from each other by at least one marker, such as CD4, are referred to herein as "subsets" of T cells.

Helper T cells (effector T cells or Th cells) are the "middlemen" of the adaptive immune system. Once activated, they divide rapidly and secrete small proteins called cytokines that regulate or assist in the immune response. Depending on the size, cytokine signals received, these cells differentiate into TH1, TH2, TH3, TH17,THF, or one of other subsets, which secrete different cytokines CD4⁺ cells are associated with MHC class II.

Cytotoxic T cells (TC cells, or CTLs) destroy virally infected cells and tumor cells, and are also implicated in transplant rejection. These cells are also known as CD8⁺ T cells (associated with MHC class I), since they express the CD8 glycoprotein at their surface. Through SLOB interaction with T regulatory CD4⁺CD25⁺FoxP3⁺ cells, these cells can be inactivated to a anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise two subtypes: central memory T cells (TCM cells) and effector memory T cells (TEM cells). Memory cells may be either CD4$^+$ or CD8$^+$.

Regulatory T cells (Treg cells), formerly known as suppressor T cells, are crucial for the maintenance of immunological tolerance. They resemble the conventional alpha beta TCR expressing CD4 positive cells. They can be further characterized by the co expression of CD25 and Foxp3 proteins. Their major role is to shut down T cell-mediated immunity toward the end of an immune reaction and to suppress autoreactive T cells that escaped the process of negative selection in the thymus. Two major classes of CD4$^+$ regulatory T cells have been described, including the naturally occurring Treg cells and the adaptive Treg cells. Naturally occurring Treg cells (also known as CD4$^+$CD25$^-$FoxP3$^+$ Treg cells) arise in the thymus, whereas the adaptive Treg cells (also known as Tr1 cells or Th3 cells) may originate during a normal immune response. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Natural killer T cells (NK T cells) are a heterogeneous T cell population characterized by the co-expression of αβ or γδ TCRs and various NK receptors, including CD16, CD56, CD161, CD94, CD158a and CD158b NK T cells have the ability to rapidly secrete large amounts of cytokines following activation. NK T cell clones secrete type 1, type 2 or both types of cytokines, which could influence the differentiation of Th0 cells towards Th1 or Th2 cells. NK T cells were described as cells that express an invariant TCR Valpha14 in mouse and Valpha24 in humans. Recently NK T cells expressing diverse TCRs have been also recognized CD3$^+$ CD56$^+$ cells represent one of the NK T cell populations NK T cells can be CD4$^+$CD8$^+$, CD4$^-$CD8$^-$, CD4$^-$CD8$^+$, or CD4$^-$CD8$^-$.

γδ T cells (gamma delta T cells) represent a small subset of T cells that possess a distinct T cell receptor (TCR) on their surface. A majority of T cells have a TCR composed of two glycoprotein chains called α- and β-TCR chains. However, in γδ T cells, the TCR is made up of one γ-chain and one δ-chain. This group of T cells is much less common (5% of total T cells) than the αβ T cells, but are found at their highest abundance in the gut mucosa, within a population of lymphocytes known as intraepithelial lymphocytes (IELs). The antigenic molecules that activate γδ T cells are still widely unknown. However, γδ T cells are not MHC restricted and seem to be able to recognize whole proteins rather than requiring peptides to be presented by MHC molecules on antigen presenting cells. Some recognize MHC class IB molecules though. Human Vγ9/Vδ2 T cells, which constitute the major γδ T cell population in peripheral blood, are unique in that they specifically and rapidly respond to a small non-peptidic microbial metabolite, HMB-PP, an isopentenyl pyrophosphate precursor. Estimates of the percentages of T cells that may be found in peripheral blood from healthy donors are as follows: CD3$^+$=70.78%±4.71; CD3$^+$CD4=38.97%±5.66; CD3$^+$CD8=28.955%±7.43; CD3$^+$CD56$^+$=5.22%±1.74; CD3$^-$CD56$^+$=10.305%±4.7; CD3$^+$CD45RA=45.00%±7.19; CD3$^+$CD45RO$^+$=27.21%±7.34.

The T cells can be a purified population of T cells, or alternatively the T cells can be in a population with cells of a different type, such as B cells and/or other peripheral blood cells. The T cells can be a purified population of a subset of T cells, such as CD4$^+$ T cells, or they can be a population of T cells comprising different subsets of T cells. In another embodiment of the invention, the T cells are T cell clones that have been maintained in culture for extended periods of time. T cell clones can be transformed to different degrees. In a specific embodiment, the T cells are a T cell clone that proliferates indefinitely in culture.

In a preferred embodiment of the invention, the T cells are primary T cells. The term "primary T cells" is intended to include T cells obtained from an individual, as opposed to T cells that have been maintained in culture for extended periods of time. Thus, primary T cells are particularly peripheral blood T cells obtained from a subject. A population of primary T cells can be composed of mostly one subset of T cells. Alternatively, the population of primary T cells can be composed of different subsets of T cells.

The T cells can be from previously stored blood samples, from a healthy individual, or alternatively from an individual affected with a condition. The condition can be an infectious disease, such as a condition resulting from a viral infection, a bacterial infection or an infection by any other microorganism, or a hyperproliferative disease, such as cancer like melanoma. In a specific embodiment, the T cells are from an individual infected with a human immunodeficiency virus (HIV). In yet another embodiment of the invention, the T cells are from a subject suffering from or susceptible to an autoimmune disease or T-cell pathologies. The T cells can be of human origin, murine origin or any other mammalian species.

B. Hematopoietic Progenitor Cells

Due to the significant medical potential of hematopoietic stem and progenitor cells, substantial work has been done to try to improve methods for the differentiation of hematopoietic progenitor cells from embryonic stem cells. In the human adult, hematopoietic stem cells present primarily in bone marrow produce heterogeneous populations of actively dividing hematopoietic (CD34$^+$) progenitor cells that differentiate into all the cells of the blood system. While it is anticipated that CD34$^+$ endothelial cells may be converted to iPS cells, in certain embodiments it may be desirable to use hematopoietic cells which are not endothelial cells; for example, in some instances it may be desirable to use hematopoietic progenitor cells or hematopoietic precursor cells which do not express CD31 or VE-cadherin. Other markers, such as the CD43 and/or CD45 marker, may also be used to help identify hematopoietic progenitor cells (e.g., Kadaja-Saarepuu et al., 2008; Vodyanik et al., 2006). Hematopoietic cells include various subsets of primitive hematopoietic cells including: CD43 (+)CD235a(+)CD41a(+/−) (erythro-megakaryopoietic), lin(−)CD34(+)CD43(+)CD45(−) (multipotent), and lin(−)CD34(+)CD43(+)CD45(+) (myeloid-skewed) cells. In an adult human, hematopoietic progenitors proliferate and differentiate resulting in the generation of hundreds of billions of mature blood cells daily. Hematopoietic progenitor cells are also present in cord blood. In vitro, human embryonic stem cells may be differentiated into hematopoietic progenitor cells. Hematopoietic progenitor cells may also be expanded or enriched from a sample of peripheral blood. The hematopoietic cells can be of human origin, murine origin or any other mammalian species.

C. Sources of Populations of Cells

Hematopoietic stem cells (HSCs) normally reside in the bone marrow but can be forced into the blood, a process termed mobilization used clinically to harvest large numbers of HSCs in peripheral blood. One mobilizing agent of choice is granulocyte colony-stimulating factor (G-CSF).

CD34+ hematopoietic stem cells or progenitors that circulate in the peripheral blood can be collected by apheresis techniques either in the unperturbed state, or after mobilization following the external administration of hematopoietic growth factors like G-CSF. The number of the stem or progenitor cells collected following mobilization is greater than that obtained after apheresis in the unperturbed state. In a particular aspect of the present invention, the source of the cell population is a subject whose cells have not been mobilized by extrinsically applied factors because there is no need to enrich hematopoietic stem cells or progenitor cells.

Populations of cells for use in the methods described herein may be mammalian cells, such as human cells, non-human primate cells, rodent cells (e.g., mouse or rat), bovine cells, ovine cells, porcine cells, equine cells, sheep cell, canine cells, and feline cells or a mixture thereof. Non-human primate cells include rhesus macaque cells. The cells may be obtained from an animal, e.g., a human patient, or they may be from cell lines. If the cells are obtained from an animal, they may be used as such, e.g., as unseparated cells (i.e., a mixed population); they may have been established in culture first, e.g., by transformation; or they may have been subjected to preliminary purification methods. For example, a cell population may be manipulated by positive or negative selection based on expression of cell surface markers; stimulated with one or more antigens in vitro or in vivo; treated with one or more biological modifiers in vitro or in vivo; or a combination of any or all of these. In an illustrative embodiment, a cell population is subjected to negative selection for depletion of non-T cells and/or particular T cell subsets. Negative selection can be performed on the basis of cell surface expression of a variety of molecules, including B cell markers such as CD19, and CD20; monocyte marker CD14; the NK cell marker CD56. Alternately, a cell population may be subjected to negative selection for depletion of non-CD34+ hematopoietic cells and/or particular hematopoietic cell subsets. Negative selection can be performed on the basis of cell surface expression of a variety of molecules, such as a cocktail of antibodies (e.g., CD2, CD3, CD11b, CD14, CD15, CD16, CD19, CD56, CD123, and CD235a) which may be used for separation of other cell types, e.g., via MACS or column separation.

Populations of cells include peripheral blood mononuclear cells (PBMC), whole blood or fractions thereof containing mixed populations, spleen cells, bone marrow cells, tumor infiltrating lymphocytes, cells obtained by leukapheresis, biopsy tissue, lymph nodes, e.g., lymph nodes draining from a tumor. Suitable donors include immunized donors, non-immunized (naive) donors, treated or untreated donors. A "treated" donor is one that has been exposed to one or more biological modifiers. An "untreated" donor has not been exposed to one or more biological modifiers.

Methods of obtaining populations of cells comprising a T cell are well known in the art. For example, peripheral blood mononuclear cells (PBMC) can be obtained as described according to methods known in the art. Examples of such methods are set forth in the Examples and is discussed by Kim et al. (1992); Biswas et al. (1990); Biswas et al. (1991).

Methods of obtaining hematopoietic precursor cells from populations of cells are also well known in the art. Hematopoietic precursor cells may be expanded using various cytokines, such as hSCF, hFLT3, and/or IL-3 (Akkina et al., 1996), or CD34+ cells may be enriched using MACS or FACS. As mentioned above, negative selection techniques may also be used to enrich CD34+ cells.

It is also possible to obtain a cell sample from a subject, and then to enrich it for a desired cell type. For example, PBMCs and/or CD34+ hematopoietic cells can be isolated from blood as described herein. Counter-flow centrifugation (elutriation) can be used to enrich for T cells from PBMCs. Cells can also be isolated from other cells using a variety of techniques, such as isolation and/or activation with an antibody binding to an epitope on the cell surface of the desired cell type, for example, some T-cell isolation kits use antibody conjugated beads to both activate the cells and then allow column separation with the same beads. Another method that can be used includes negative selection using antibodies to cell surface markers to selectively enrich for a specific cell type without activating the cell by receptor engagement.

Bone marrow cells may be obtained from iliac crest, femora, tibiae, spine, rib or other medullary spaces. Bone marrow may be taken out of the patient and isolated through various separations and washing procedures. A known procedure for isolation of bone marrow cells comprises the following steps: a) centrifugal separation of bone marrow suspension in three fractions and collecting the intermediate fraction, or buffycoat; b) the buffycoat fraction from step (a) is centrifuged one more time in a separation fluid, commonly Ficoll (a trademark of Pharmacia Fine Chemicals AB), and an intermediate fraction which contains the bone marrow cells is collected; and c) washing of the collected fraction from step (b) for recovery of re-transfusable bone marrow cells.

If one desires to use a population of cells enriched in T cells, such populations of cells can be obtained from a mixed population of cells by leukapheresis and mechanical apheresis using a continuous flow cell separator. For example, T cells can be isolated from the buffy coat by any known method, including separation over Ficoll-Hypaque™ gradient, separation over a Percoll gradient, or elutriation.

D. T Cell Activation

In certain aspects, T cells are activated by agents that bind to T cell receptors to trigger a signaling cascade for T cell activation. For example, a CD3 antibody may be used. For T cell expansion to a significant number and a proliferating state for reprogramming, a cytokine may also be used, such as IL-2.

Naive T cells can live for many years without dividing. These small resting cells have condensed chromatin and a scanty cytoplasm and synthesize little RNA or protein. On activation, they must reenter the cell cycle and divide rapidly to produce the large numbers of progeny that will differentiate into armed effector T cells. Their proliferation and differentiation are driven by a cytokine called interleukin-2 (IL-2), which is produced by the activated T cell itself.

The initial encounter with specific antigen in the presence of the required co-stimulatory signal triggers entry of the T cell into the $G_1$ phase of the cell cycle; at the same time, it also induces the synthesis of IL-2 along with the a chain of the IL-2 receptor. The IL-2 receptor has three chains: $\alpha$, $\beta$, and $\gamma$. Resting T cells express a form of this receptor composed of $\beta$ and $\gamma$ chains which binds IL-2 with moderate affinity, allowing resting T cells to respond to very high concentrations of IL-2. Association of the a chain with the $\beta$ and $\gamma$ chains creates a receptor with a much higher affinity for IL-2, allowing the cell to respond to very low concentrations of IL-2. Binding of IL-2 to the high-affinity receptor then triggers progression through the rest of the cell cycle. T cells activated in this way can divide two to three times a day for several days, allowing one cell to give rise to a clone composed of thousands of progeny that all bear the same receptor for antigen. IL-2 also promotes the differentiation of these cells into armed effector T cells.

Although the specific mechanisms of activation vary slightly between different types of T cells, the "two-signal model" in CD4+ T cells holds true for most. Activation of CD4+ T cells occurs through the engagement of both the T cell receptor and CD28 on the T cell by the Major histocompatibility complex peptide and B7 family members on the APC, respectively. Both are required for production of an effective immune response; in the absence of CD28 co-stimulation, T cell receptor signalling alone results in anergy. The signalling pathways downstream from both CD28 and the T cell receptor involve many proteins.

The first signal is provided by binding of the T cell receptor to a short peptide presented by the major histocompatibility complex (MHC) on another cell. This ensures that only a T cell with a TCR specific to that peptide is activated. The partner cell is usually a professional antigen presenting cell (APC), usually a dendritic cell in the case of naïve responses, although B cells and macrophages can be important APCs. The peptides presented to CD8+ T cells by MHC class I molecules are 8-9 amino acids in length; the peptides presented to CD4+ cells by MHC class II molecules are longer, as the ends of the binding cleft of the MHC class II molecule are open.

The second signal comes from co-stimulation, in which surface receptors on the APC are induced by a relatively small number of stimuli, usually products of pathogens, but sometimes breakdown products of cells, such as necrotic-bodies or heat-shock proteins. The only co-stimulatory receptor expressed constitutively by naïve T cells is CD28, so co-stimulation for these cells comes from the CD80 and CD86 proteins on the APC. Other receptors are expressed upon activation of the T cell, such as OX40 and ICOS, but these largely depend upon CD28 for their expression. The second signal licenses the T cell to respond to an antigen. Without it, the T cell becomes anergic, and it becomes more difficult for it to activate in future. This mechanism prevents inappropriate responses to self, as self-peptides will not usually be presented with suitable co-stimulation.

In a certain aspect, both anti-CD3 and anti-CD28 may be used for T cell activation where co-stimulation is involved. In an alternative aspect, cross-linking of the anti-CD3 may be applied, such as plate bound anti-CD3. If soluble anti-CD3 is used to activate T cells in PBMC, the soluble anti-CD3 antibody may bind to APCs in the PBMC, which then presents the antibody to the T cells. If the soluble anti-CD3 antibody alone is used in a population of purified T-cells, anergy would result for the reasons mentioned above. A certain embodiment of the present invention comprises culturing T cells in the presence of the anti-CD3 (OKT3) and IL2, which is advantageous and convenient because there is no need to use costly and cumbersome beads or plate-bound antibody; after adding OKT3 and IL2, the cellular milieu of PBMCs would help activate the T cells. The T cells then overcrowd the other cell types in the PBMC culture due to preferential expansion.

The T cell receptor exists as a complex of several proteins. The actual T cell receptor is composed of two separate peptide chains, which are produced from the independent T cell receptor alpha and beta (TCRα and TCRβ) genes. The other proteins in the complex are the CD3 proteins: CD3εγ and CD3εδ heterodimers and, most important, a CD3ζ homodimer, which has a total of six ITAM motifs. The ITAM motifs on the CD3ζ can be phosphorylated by Lck and in turn recruit ZAP-70. Lck and/or ZAP-70 can also phosphorylate the tyrosines on many other molecules, not least CD28, LAT and SLP-76, which allows the aggregation of signalling complexes around these proteins.

Phosphorylated LAT recruits SLP-76 to the membrane, where it can then bring in PLCγ, VAV1, Itk and potentially PI3K. Both PLCγ and PI3K act on PI(4,5)P2 on the inner leaflet of the membrane to create the active intermediaries diacylglycerol (DAG), inositol-1,4,5-trisphosphate (IP3), and phosphatidlyinositol-3,4,5-trisphosphate (PIP3). DAG binds and activates some PKCs in T cells, e.g., PKCθ, a process important for activating the transcription factors NF-κB and AP-1. IP3 is released from the membrane by PLCγ and diffuses rapidly to activate receptors on the ER, which induce the release of calcium. The released calcium then activates calcineurin, and calcineurin activates NFAT, which then translocates to the nucleus. NFAT is a transcription factor, which activates the transcription of a pleiotropic set of genes, most notable, IL-2, a cytokine that promotes long term proliferation of activated T cells.

According to the method of the invention, the nucleic acid molecule is introduced into T cells that are actively proliferating (i.e., expanding). T cells can be stimulated to expand by contacting the T cells with a variety of agents, such as a combination of agents providing a primary activation signal and a costimulatory signal to T cells. Agents that can be used to stimulate T cells to expand are well known in the art and are described below. T cells that are stimulated to proliferate are characterized by cellular enlargement, clumping, and acidification of the culture medium. Thus, T cell proliferation can be evidenced by, for example, examining the size or measuring the volume of the T cells, such as with a Coulter Counter. A resting T cell has a mean diameter of about 6.8 microns. Following the initial activation and stimulation the T cell mean diameter will increase to over 12 microns by day 4 and begin to decrease by about day 6. Moreover, T cell proliferation can be assessed by standard techniques known in the art, such as tritiated thymidine uptake.

The method of the invention involves contacting proliferating T cells with at least one stimulatory agent prior to introducing the nucleic acid molecule into the proliferating T cell. The term "stimulatory agent" is intended to include agents which provide a signal to the T cell, such that the level of expression of the gene comprised in the nucleic acid molecule transfected into the T cell is higher when the T cell is contacted with the stimulatory agent prior to introducing the nucleic acid molecule into the T cell, than in T cells not contacted with the stimulatory agent prior to introducing the nucleic acid molecule.

In a specific embodiment of the invention, the stimulatory agent is an agent which provides a primary activation signal to a T cell. The language "primary activation signal" is intended to include signals, typically triggered through the TCR/CD3 complex, that induce activation of T cells. Activation of a T cell is intended to include modifications of a T cell, such that the T cell is induced to proliferate and differentiate upon receiving a second signal, such as a costimulatory signal. In a specific embodiment, the primary activation signal is provided by an agent which contacts the T cell receptor or the CD3 complex associated with the T cell receptor. In a preferred embodiment, the agent is an antibody reactive against CD3, such as the monoclonal antibody OKT3 (available from the American Type Culture Collection, Rockville, Md.; No. CRL 8001). In another embodiment of the invention, the stimulating agent is an agent that stimulates the CD2 complex on T cells, such as a combination of antibodies, e.g. T11.3+T11.1 or T11.3+T11.2 (see e.g., Meuer et al., 1984).

In another embodiment of the method, the stimulatory agent is a lymphokine, such as IL-2. The lymphokine is particularly used in combination with another agent, such as an agent which provides a primary activation signal to the T cell, for stimulating T cells. Thus, in a preferred embodiment of the invention, T cells are contacted with a combination of an agent which provides a primary activation signal to the T cells (e.g., an anti-CD3 antibody) and an effective amount of IL-2, prior to transfecting the T cells with a nucleic acid molecule, such that the nucleic acid molecule is expressed in the T cells.

In a preferred embodiment of the invention, the T cells are activated with a combination of agents that stimulate both a primary activation signal and a costimlulatory signal in the T cell. The term "costimulatory agent" is intended to include agents which provide a costimulatory signal in T cells, such that a T cell that has received a primary activation signal (e.g. an activated T cell) is stimulated to proliferate or to secrete cytokines, such as IL-2, IL-4, or interferon-γ. In a specific embodiment, the costimulatory agent interacts with CD28 or CTLA4 molecules on the surface of the T cells. In an even more specific embodiment, the costimulatory signal is a ligand of CD28 or CTLA4, such as a B-lymphocyte antigen B7-1 or B7-2. The language "stimulatory form of a natural ligand of CD28" is intended to include B7-1 and B7-2 molecules, fragments thereof, or modifications thereof, which are capable of providing costimulatory signals to the T cells. Stimulatory forms of natural ligands of CD28 can be identified by, for example, contacting activated peripheral blood lymphocytes with a form of a natural ligand of CD28 and performing a standard T cell proliferation assay. Thus, a stimulatory form of a natural ligand of CD28 is capable of stimulating proliferation of the T cells. Stimulatory forms of natural ligands of CD28/CTLA4 are described, for example, in PCT Publication No. WO 95/03408.

Other agents that can be used to activate T cells prior to introducing a nucleic acid molecule into the T cell include agents that stimulate one or more intracellular signal transduction pathways involved in T cell activation and/or costimulation. In a specific embodiment of the invention, the stimulatory agent is a calcium ionophore, such as ionomycin or A23187. Alternatively, the stimulatory agent can be an agent which stimulates protein kinase C, such as a phorbol ester. A preferred phorbol ester is phorbol-12,13-dibutyrate. In an even more preferred embodiment of the invention, T cells are contacted with a combination of a calcium ionophore and a phorbol ester prior to transfection with a nucleic acid molecule. The stimulatory agent can also be an agent which activates protein tyrosine kinases. A preferred agent that stimulates protein tyrosine kinases is pervanadate (O'Shea et al., 1992).

In yet another embodiment of the invention, the stimulatory agent is a polyclonal activator. Polyclonal activators include agents that bind to glycoproteins expressed on the plasma membrane of T cells and include lectins, such as phytohemaglutinin (PHA), concanavalin (Con A) and pokeweed mitogen (PWM).

By providing a clone a specific activation signal, it is possible to selectively transfect only a certain clone of T cells in a population of T cells. Specific activation of a T cell clone can be accomplished, for example, using a specific antigen presented by an antigen-presenting cell.

Other stimulating agents that can be used include super-antigens. The term "super-antigen" as defined herein is intended to include bacterial enterotoxins, or other bacterial proteins capable of stimulating proliferation of T cells. Super-antigens include *staphylococcal* enterotoxins (SE), such as SEA, SEB, SEC, SED, and SEE. Super-antigens can also be of viral origin, such as retroviral super-antigens.

Additional agents that are capable of stimulating T cells, either alone or in combination with other agents, that may be identified using T cell stimulation assays as known in the art or described herein are also within the scope of the invention.

For stimulating T cells prior to introduction of a nucleic acid molecule into the T cells, any combination of the above described agents can be used.

The stimulating agents can be used in solution, or attached to a solid surface. The solid surface can be, for example, the surface of a tissue culture dish or a bead. Depending on the nature of the stimulatory agent, linkage to the solid surface can be performed by methods well known in the art. For example, proteins can be chemically crosslinked to the cell surface using commercially available crosslinking reagents (Pierce, Rockford Ill.) or immobilized on plastic by overnight incubation at 4° C. If several agents are used for stimulation of the T cells, some agents may be in solution and some agents may be attached to a solid support. In a preferred embodiment, the T cells are stimulated with a combination of solid phase coupled anti-CD3 antibody and soluble anti-CD28 antibody.

The specific doses of stimulatory agent(s) to be added to the T cells will vary with the type of stimulating agent. Typically, the stimulating agents are used at the same doses at which they are used for stimulating T cells to proliferate and secrete cytokines, as described in the art.

In a preferred embodiment of the invention, the method of the invention further comprises stimulating the T cells to expand in vitro after transfection of the T cells. T cells can be stimulated to expand in vitro as described in the Examples section in the presence of IL-2. In a specific embodiment, T cells may also be incubated with an agent which provides a primary activating signal, such as anti-CD3 and an agent which provides a costimulatory signal, such as an anti-CD28 antibody.

In an even more preferred embodiment, the T cells are primary T cells. Thus, T cells can be obtained from a subject, transfected according to the method of the invention, and expanded in vitro. In another embodiment of the invention, the transfected and expanded T cells are re-administered to the subject. It may be preferable to further purify the T cells prior to administering into the subject, such as by gradient centrifugation.

E. V(D)J Recombination

The inventors discovered that V(D)J recombination in the T cell receptors did not inhibit T cell reprogramming. The specific rearragements of iPS cells derived from T cells may serve as a unique "bar code" to track iPS cells and identify different populations of iPS cells in certain aspects. In a further aspect, there may also be provided iPS cells with an incomplete set of V, D, J gene segments, as compared with embryonic stem cells which have the original set of V, D, J gene segments. The arrangement of the V, D, J gene segments of thse iPS cells may be the same within a clonal population, but may be different among different clonal populations. In particular aspects, gamma/delta TCR$^+$ T-cells may be also reprogrammed with the present methods. An iPS clone originating from one of this population of T-cells could be advantageous because they may have a genome that more closely resembles the germ line configuration and thus may be able to re-differentiate into a more robust repertoire of T-cells or other differentiated cells, for example.

V(D)J recombination is a mechanism of genetic recombination that occurs in vertebrates, which randomly selects and assembles segments of genes encoding specific proteins with important roles in the immune system. This site-specific recombination reaction generates a diverse repertoire of T cell receptor (TCR) and immunoglobulin (Ig) molecules that are necessary for the recognition of diverse antigens from bacterial, viral, and parasitic invaders, and from dysfunctional cells such as tumor cells.

Most T cell receptors are composed of an alpha chain and a beta chain. The T cell receptor genes are similar to immunoglobulin genes in that they too contain multiple V, D and J genes in their beta chains (and V and J genes in their alpha chains) that are rearranged during the development of the lymphocyte to provide that cell with a unique antigen receptor.

During T cell development, the T cell receptor (TCR) chains undergo essentially the same sequence of ordered recombination events as that described for immunoglobulins. D-to-J recombination occurs first in the β chain of the TCR. This process can involve either the joining of the $D_\beta 1$ gene segment to one of six $J_\beta 1$ segments or the joining of the $D_\beta 2$ gene segment to one of six $J_\beta 2$ segments. DJ recombination is followed (as above) with $V_\beta$-to-$D_\beta J_\beta$ rearrangements. All genes between the $V_\beta$-$D_\beta$-$J_\beta$ genes in the newly formed complex are deleted and the primary transcript is synthesized that incorporates the constant domain gene ($V_\beta$-$D_\beta$-$J_\beta$-$C_\beta$). mRNA transcription splices out any intervening sequence and allows translation of the full length protein for the TCR $C_\beta$ chain.

The rearrangement of the alpha (α) chain of the TCR follows β chain rearrangement, and resembles V-to-J rearrangement described for Ig light chains (see above). The assembly of the β- and α-chains results in formation of the αβ-TCR that is expressed on a majority of T cells.

VI. Reprogramming Factors Expression and Transduction

In certain aspects of the present invention, reprogramming factors are expressed from expression cassettes comprised in one or more vectors, such as an integrating vector or an episomal vector. In a further aspect, reprogramming proteins could be introduced directly into somatic cells by protein transduction (see U.S. Application No. 61/172,079, incorporated herein by reference).

A. Integrating Vectors

IPS cells may be derived by transfection of certain nucleic acids or genes encoding reprogramming proteins into non-pluripotent cells, such as T cells or hematopoietic precursor cells, in the present invention. Transfection is typically achieved through integrating viral vectors in the current practice, such as retroviruses. Transfected genes may include the master transcriptional regulators Oct4 (Pouf51) and Sox2, although it is suggested that other genes enhance the efficiency of induction. After a critical period, small numbers of transfected cells may begin to become morphologically and biochemically similar to pluripotent stem cells, and could be isolated through morphological selection, doubling time, or through a reporter gene and antibiotic infection.

In November 2007, a milestone was achieved by creating iPS from adult human fibroblasts from two independent research teams' studies (Yu et al., 2007; Yamanaka et al., 2007). With the same principle used earlier in mouse models, Yamanaka had successfully transformed human fibroblasts into pluripotent stem cells using the same four pivotal genes: Oct4, Sox2, Klf4, and c-Myc with a retroviral system but c-Myc is oncogenic. Thomson and colleagues used Oct4, Sox2, NANOG, and a different gene LIN28 using a lentiviral system avoiding the use of c-Myc. More recently, fertile mice have been generated from iPS cells, thus demonstrating the potential of these cells to form essentially any or all differentiated cell types (Boland et al., 2009).

As described above, induction of pluripotent stem cells from human dermal fibroblasts has been achieved using retroviruses or lentiviral vectors for ectopic expression of reprogramming genes. Recombinant retroviruses such as the Moloney murine leukemia virus have the ability to integrate into the host genome in a stable fashion. They contain a reverse transcriptase which allows integration into the host genome. Lentiviruses are a subclass of Retroviruses. They are widely adapted as vectors thanks to their ability to integrate into the genome of non-dividing as well as dividing cells. The viral genome in the form of RNA is reverse-transcribed when the virus enters the cell to produce DNA, which is then inserted into the genome at a random position by the viral integrase enzyme. Therefore, successful reprogramming of T cells may use integration-based viral approaches as shown in the Examples section.

B. Episomal Vectors

These reprogramming methods may also make use of extra-chromosomally replicating vectors (i.e., episomal vectors), which are vectors capable of replicating episomally to make iPS cells essentially free of exogenous vector or viral elements (see U.S. Application No. 61/058,858, incorporated herein by reference; Yu et al., 2009). A number of DNA viruses, such as adenoviruses, Simian vacuolating virus 40 (SV40) or bovine papilloma virus (BPV), or budding yeast ARS (Autonomously Replicating Sequences)-containing plasmids replicate extra-chromosomally or episomally in mammalian cells. These episomal plasmids are intrinsically free from all these disadvantages (Bode et al., 2001) associated with integrating vectors. For example, a lymphotrophic herpes virus-based including or Epstein Barr Virus (EBV) as defined above may replicate extra-chromosomally and help deliver reprogramming genes to somatic cells.

For example, the plasmid-based approach used in the invention may extract robust elements necessary for the successful replication and maintenance of an EBV element-based system without compromising the system's tractability in a clinical setting as described in detail below. The essential EBV elements are OriP and EBNA-1 or their variants or functional equivalents. An additional advantage of this system is that these exogenous elements will be lost with time after being introduced into cells, leading to self-sustained iPS cells essentially free of exogenous elements.

The use of plasmid- or liposome-based extra-chromosomal vectors, e.g., oriP-based vectors, and/or vectors encoding a derivative of EBNA-1 permit large fragments of DNA to be introduced to a cell and maintained extra-chromosomally, replicated once per cell cycle, partitioned to daughter cells efficiently, and elicit substantially no immune response. In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Also other sources of episome-base vectors are contemplated, such as yeast ARS, adenovirus, SV40, or BPV.

To circumvent potential problems from viral gene delivery, two groups this year reported on a collaboration that has succeeded in transposon-based approaches for producing pluripotency in human cells without using viral vectors (Woltjen et al., 2009; Kaji et al., 2009). Stable iPS cells were produced in both human and mouse fibroblasts using virus-derived 2A peptide sequences to create a multicistronic vector incorporating the reprogramming factors, delivered to the cell by the piggyBac transposon vector. The 2A-linked reprogramming factors, not required in the established iPS cell lines, were then removed. These strategies could be similarly applied to reprogram T cells or hematopoietic precursor cells in certain aspects of the present invention.

C. Protein Transduction

One possible way to avoid introducing exogenous genetic modifications to target cells would be to deliver the reprogramming proteins directly into cells, rather than relying on the transcription from delivered genes. Previous studies have demonstrated that various proteins can be delivered into cells in vitro and in vivo by conjugating them with a short peptide that mediates protein transduction, such as HIV tat and polyarginine. A recent study demonstrated that murine fibroblasts can be fully reprogrammed into pluripotent stem cells by direct delivery of recombinant reprogramming proteins (Zhou et al., 2009). More details of the methods for reprogramming cells with protein transduction have been disclosed in U.S. Application No. 61/172,079 incorporated herein by reference.

In certain aspects of the present invention, protein transduction domains could been used to introduce reprogramming proteins directly into T cells. Protein transduction may be used to enhance the delivery of reprogramming proteins into cells. For example, a region of the TAT protein which is derived from the HIV Tat protein can be fused to a target protein allowing the entry of the target protein into the cell. The advantages of using fusions of these transduction domains is that protein entry is rapid, concentration-dependent and appears to work with different cell types.

In a further aspect of the present invention, a nuclear localization sequence may also be used to facilitate nuclear entry of reprogramming proteins. Nuclear localization signals (NLS) have been described for various proteins. The mechanism of protein transport to the nucleus is through the binding of a target protein containing a nuclear localization signal to alpha subunit of karyopherin. This is followed by transport of the target protein:karyopherin complex through the nuclear pore and into the nucleus. However, reprogramming proteins are often transcription factors which may have endogenous nuclear localization sequences. Therefore, nuclear localization sequences may not be necessary.

The direct introduction of reprogramming proteins into somatic cells may be used in the present invention, with reprogramming proteins operatively linked to a protein transduction domain (PTD), either by creating a fusion protein comprising such a domain or by chemically cross-linking the reprogramming protein and PTD via functional groups on each molecule.

Standard recombinant nucleic acid methods can be used to express one or more transducible reprogramming proteins used herein. In one embodiment, a nucleic acid sequence encoding the transducible protein is cloned into a nucleic acid expression vector, e.g., with appropriate signal and processing sequences and regulatory sequences for transcription and translation. In another embodiment, the protein can be synthesized using automated organic synthetic methods.

In addition, there have been several methods that may also help the transport of proteins into cells, one ore more of which can be used alone or in combination with the methods using the protein transduction domains, including, but not limited to, microinjection, electroporation, and the use of liposomes. Most of these methods may need a purified preparation of protein. Purification of recombinant proteins is often facilitated by the incorporation of an affinity tag into the expression construct, making the purification step fast and efficient.

VII. Vector Construction and Delivery

In certain embodiments, reprogramming vectors could be constructed to comprise additional elements in addition to nucleic acid sequences encoding reprogramming factors as described above in cells. Details of components of these vectors and delivery methods are disclosed below.

A. Vector

One of skill in the art would be well equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also might include markers, such as detectable and/or selection markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

B. Regulatory Elements

Eukaryotic expression cassettes included in the vectors particularly contain (in a 5'-to-3' direction) a eukaryotic transcriptional promoter operably linked to a protein-coding sequence, splice signals including intervening sequences, and a transcriptional termination/polyadenylation sequence.

i. Promoter/Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

Promoters suitable for use in EBNA 1-encoding vector of the invention are those that direct the expression of the expression cassettes encoding the EBNA 1 protein to result in sufficient steady-state levels of EBNA 1 protein to stably maintain EBV oriP-containing vectors. Promoters are also used for efficient expression of expression cassettes encoding reprogramming factors.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/ or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). A specific example could be a phosphoglycerate kinase (PGK) promoter.

ii. Protease Cleavage Sites/Self-Cleaving Peptides and Internal Ribosome Binding Sites In certain aspects, according to the present invention, the genes encoding markers or reprogramming proteins may be connected to one another by a sequence (there may be more than one) coding for a protease cleavage site (i.e. a sequence comprising the recognition site of a protease) or at least one self-cleaving peptide.

According to a certain embodiment of the present invention the protease(s) capable of cleaving the cleavage sites encoded by the sequence(s) connecting the genes constituting the polycistronic message is/are encoded by the polynucleotide of the present invention. More particularly, the gene(s) encoding the protease(s) is/are part of at least one of the polycistronic meassage.

Suitable protease cleavages sites and self-cleaving peptides are known to the skilled person (see, e.g., in Ryan et al., 1997; Scymczak et al., 2004). Preferred examples of protease cleavage sites are the cleavage sites of potyvirus NIa proteases (e.g. tobacco etch virus protease), potyvirus HC proteases, potyvirus P1 (P35) proteases, byovirus N1a proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3Ciike protease, PY\IF (parsnip yellow fleck virus) 3C-like protease, thrombin, factor Xa and enterokinase. Due to its high cleavage stringency, TEV (tobacco etch virus) protease cleavage sites may be used.

Exemplary self-cleaving peptides (also called "cis-acting hydrolytic elements", CHYSEL; see deFelipe (2002) are derived from potyvirus and cardiovirus 2A peptides. Particular self-cleaving peptides may be selected from 2A peptides derived from FMDV (foot-and-mouth disease virus), equine rhinitis A virus, Thoseà asigna virus and porcine teschovirus.

A specific initiation signal also may be used for efficient translation of coding sequences in a polycistronic message. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

iii. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

iv. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

v. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

vi. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

vii. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in differentiation programming, which is a specific nucleic acid sequence at which replication is initiated. Alternatively a replication origin of other extra-chromosomally replicating virus as described above or an autonomously replicating sequence (ARS) can be employed.

viii. Selection and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art. One feature of the present invention includes using selection and screenable markers to select vector-free cells after the differentiation programming factors have effected a desired altered differentiation status in those cells.

C. Vector Delivery

Introduction of a reprogramming vector into somatic cells with the current invention may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

i. Liposome-Mediated Transfection

In a certain embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen). The amount of liposomes used may vary upon the nature of the liposome as well as the, cell used, for example, about 5 to about 20 μg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

ii. Electroporation

In certain embodiments of the present invention, a nucleic acid is introduced into a cell via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 μg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

iii. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

iv. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

v. Sonication Loading

Additional embodiments of the present invention include the introduction of a nucleic acid by direct sonic loading. LTK⁻ fibroblasts have been transfected with the thymidine kinase gene by sonication loading (Fechheimer et al., 1987).

vi. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will particularly comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

vii Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and particularly, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

VIII. Selection of iPS Cells

In certain aspects of the invention, after one or more reprogramming factors are introduced into somatic cells, cells will be cultured for expansion (optionally selected for the presence of vector elements like positive selection or screenable marker to concentrate transfected cells). Reprogramming vectors may express reprogramming factors in these cells and replicate and partition along with cell division. Alternatively, reprogramming proteins could enter these cells and their progeny by replenishing medium containing the reprogramming proteins. These reprogramming factors will reprogram somatic cell genome to establish a self-sustaining pluripotent state, and in the meantime or after removal of positive selection of the presence of vectors, exogenous genetic elements will be lost gradually, or there is no need to add reprogramming proteins.

These induced pluripotent stem cells could be selected from progeny derived from these T cells or hematopoietic precursor cells based on embryonic stem cell characteristics because they are expected to be substantially identical to pluripotent embryonic stem cells. An additional negative selection step could be also employed to accelerate or help selection of iPS cells essentially free of exogenous genetic elements by testing the absence of reprogramming vector DNA or using selection markers, such as reporters.

A. Selection for Embryonic Stem Cell Characteristics

The successfully generated iPSCs from previous studies were remarkably similar to naturally-isolated pluripotent stem cells (such as mouse and human embryonic stem cells, mESCs and hESCs, respectively) in the following respects, thus confirming the identity, authenticity, and pluripotency of iPSCs to naturally-isolated pluripotent stem cells. Thus, induced pluripotent stem cells generated from the methods disclosed in this invention could be selected based on one or more of following embryonic stem cell characteristics.

i. Cellular Biological Properties

Morphology:

iPSCs are morphologically similar to ESCs. Each cell may have round shape, dual nucleoli or large nucleolus and scant cytoplasm. Colonies of iPSCs could be also similar to that of ESCs. Human iPSCs form sharp-edged, flat, tightly-packed colonies similar to hESCs and mouse iPSCs form the colonies similar to mESCs, less flat and more aggregated colonies than that of hESCs.

Growth Properties:

Doubling time and mitotic activity are cornerstones of ESCs, as stem cells must self-renew as part of their definition. iPSCs could be mitotically active, actively self-renewing, proliferating, and dividing at a rate equal to ESCs.

Stem Cell Markers:

iPSCs may express cell surface antigenic markers expressed on ESCs. Human iPSCs expressed the markers specific to hESC, including, but not limited to, SSEA-3, SSEA-4, TRA-1-60, TRA-1-81, TRA-2-49/6E, and Nanog. Mouse iPSCs expressed SSEA-1 but not SSEA-3 nor SSEA-4, similarly to mESCs.

Stem Cell Genes:

iPSCs may express genes expressed in undifferentiated ESCs, including Oct4, Sox2, Nanog, GDF3, REX1, FGF4, ESG1, DPPA2, DPPA4, and hTERT.

Telomerase Activity:

Telomerases are necessary to sustain cell division unrestricted by the Hayflick limit of ~50 cell divisions. hESCs express high telomerase activity to sustain self-renewal and proliferation, and iPSCs also demonstrate high telomerase activity and express hTERT (human telomerase reverse transcriptase), a necessary component in the telomerase protein complex.

Pluripotency:

iPSCs will be capable of differentiation in a fashion similar to ESCs into fully differentiated tissues.

Neural Differentiation:

iPSCs could be differentiated into neurons, expressing βIII-tubulin, tyrosine hydroxylase, AADC, DAT, ChAT, LMX1B, and MAP2. The presence of catecholamine-associated enzymes may indicate that iPSCs, like hESCs, may be differentiable into dopaminergic neurons. Stem cell-associated genes will be downregulated after differentiation.

Cardiac Differentiation:

iPSCs could be differentiated into cardiomyocytes that spontaneously begin beating. Cardiomyocytes express cTnT, MEF2C, MYL2A, MYHCβ, and NKX2.5. Stem cell-associated genes will be downregulated after differentiation.

Teratoma Formation:

iPSCs injected into immunodeficient mice may spontaneously forme teratomas after certain time, such as nine weeks. Teratomas are tumors of multiple lineages containing tissue derived from the three germ layers endoderm, mesoderm and ectoderm; this is unlike other tumors, which typically are of only one cell type. Teratoma formation is a landmark test for pluripotency.

Embryoid Body:

hESCs in culture spontaneously form ball-like embryo-like structures termed "embryoid bodies," which consist of a core of mitotically active and differentiating hESCs and a periphery of fully differentiated cells from all three germ layers. iPSCs may also form embryoid bodies and have peripheral differentiated cells.

Blastocyst Injection:

hESCs naturally reside within the inner cell mass (embryoblast) of blastocysts, and in the embryoblast, differentiate into the embryo while the blastocyst's shell (trophoblast) differentiates into extraembryonic tissues. The hollow trophoblast is unable to form a living embryo, and thus it is necessary for the embryonic stem cells within the embryoblast to differentiate and form the embryo. iPSCs injected by micropipette into a trophoblast to generate a blastocyst transferred to recipient females, may result in chimeric living mouse pups: mice with iPSC derivatives incorporated all across their bodies with 10%-90 and chimerism.

ii. Epigenetic Reprogramming

Promoter Demethylation:

Methylation is the transfer of a methyl group to a DNA base, typically the transfer of a methyl group to a cytosine molecule in a CpG site (adjacent cytosine/guanine sequence). Widespread methylation of a gene interferes with expression by preventing the activity of expression proteins or recruiting enzymes that interfere with expression. Thus, methylation of a gene effectively silences it by preventing transcription. Promoters of pluripotency-associated genes, including Oct4, Rex1, and Nanog, may be demethylated in iPSCs, showing their promoter activity and the active promotion and expression of pluripotency-associated genes in iPSCs.

Histone Demethylation:

Histones are compacting proteins that are structurally localized to DNA sequences that can effect their activity through various chromatin-related modifications. H3 histones associated with Oct/4, Sox2, and Nanog may be demethylated to activate the expression of Oct4, Sox2, and Nanog.

IX. Culturing and Differentiation of iPS Cells

After somatic cells are introduced with reprogramming factors using the disclosed methods, these cells may be cultured in a medium sufficient to maintain the pluripotency. Culturing of induced pluripotent stem (iPS) cells generated in this invention can use various medium and techniques developed to culture primate pluripotent stem cells, more specially, embryonic stem cells, as described in U.S. Pat. App. 20070238170 and U.S. Pat. App. 20030211603. It is appreciated that additional methods for the culture and maintenance of human pluripotent stem cells, as would be known to one of skill, may be used with the present invention.

In certain embodiments, undefined conditions may be used; for example, pluripotent cells may be cultured on fibroblast feeder cells or a medium which has been exposed to fibroblast feeder cells in order to maintain the stem cells in an undifferentiated state. Alternately, pluripotent cells may be cultured and maintained in an essentially undifferentiated state using defined, feeder-independent culture system, such as a TeSR medium (Ludwig et al., 2006; Ludwig et al., 2006). Feeder-independent culture systems and media may be used to culture and maintain pluripotent cells. These approaches allow human embryonic stem cells to remain in an essentially undifferentiated state without the need for mouse fibroblast "feeder layers." As described herein, various modifications may be made to these methods in order to reduce costs as desired.

For example, like human embryonic stem (hES) cells, iPS cells can be maintained in 80% DMEM (Gibco #10829-018 or #11965-092), 20% defined fetal bovine serum (FBS) not heat inactivated (or human AB serum), 1% non-essential amino acids, 1 mM L-glutamine, and 0.1 mM β-mercaptoethanol. Alternatively, iPS cells can be maintained in serum-free medium, made with 80% Knock-Out DMEM (Gibco #10829-018), 20% serum replacement (Gibco #10828-028), 1% non-essential amino acids, 1 mM L-glutamine, and 0.1 mM β-mercaptoethanol. Just before use, human bFGF may be added to a final concentration of about 4 ng/mL (WO 99/20741) or zebrafish bFGF may be used instead as in the Examples.

Various matrix components may be used in culturing and maintaining human pluripotent stem cells. For example, collagen IV, fibronectin, laminin, and vitronectin in combination may be used to coat a culturing surface as a means of providing a solid support for pluripotent cell growth, as described in Ludwig et al. (2006a; 2006b), which are incorporated by reference in its entirety.

Matrigel™ may also be used to provide a substrate for cell culture and maintenance of human pluripotent stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture.

IPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5\text{-}10 \times 10^6$ cells into the rear leg muscles of 8-12 week old male SCID mice. Teratomas develop that demonstrate at least one cell type of each of the three germ layers.

Various approaches may be used with the present invention to differentiate iPS cells into cell lineages including, but not limited to, hematopoietic cells, myocytes (e.g., cardiomyocytes), neurons, fibroblasts and epidermal cells, and tissues or organs derived therefrom. Exemplary methods of hematopoietic differentiation of iPS cells may include, for example, methods disclosed by U.S. Application No. 61/088,054 and No. 61/156,304, both incorporated herein by reference in their entirety, or embryoid body (EB) based methods (Chadwick et al., 2003; Ng et al., 2005). Fibronectin differentiation methods may also be used for blood lineage differentiation, as exemplified in Wang et al., 2007. Exemplary methods of cardiac differentiation of iPS cells may include embryoid body (EB) methods (Zhang, et al., 2009), OP9 stroma cell methods (Narazaki, et al., 2008), or growth factor/chemical methods (see U.S. Patent Publn. 20080038820, 20080226558, 20080254003 and 20090047739, all incorporated herein by reference in their entirety).

X. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Processing Leukophoresis into Aliquots of PBMCs

The leukophoresis sample (leukopak) was derived from a process in which 8 liters of peripheral blood was circulated through a centrifugal field in order to concentrate mononuclear cells and limit the amount of red blood cells in a resulting volume of approximately 125 ml. The leukopak was further processed as follows: One end of a leukopak bag was swabbed with alcohol swab and cut with razor blade to drain into a flask. The volume was diluted to between approximately 500 ml with Hank's solution and then aliquoted into 16-29 tubes with 50 ml capacity, 30 ml per tube. The tubes were spun at 400 g for 30 minutes with no brake and no acceleration. White liquid was aspirated and new 50 ml tubes were filled up halfway and topped off with 25 ml PBS. This procedure was repeated 2 additional times for a total of 3 washes. Cells were counted before the last wash using a hemacytometer. The yield was between 30-60 tubes of $1 \times 10^8$ cells/tube.

To process whole blood the blood draws were collected in a tube containing an anticoagulant or a CPT tube. A brief outline for processing blood samples obtained by the CPT tube is provided, Briefly transfer approximately 7-8 ml from the upper (plasma) phase into a 50 ml sterile tube. Dilute to 50 ml with calcium-free PBS. Invert to mix. Centrifuge for 15 minutes at 300 RCF. Remove approximately 95% of the supernatant without disturbing the pellet. Transfer the supernatant into a separate 50 ml tube. Gently resuspend the pellet by tapping the tube. Add 20 ml of calcium-free PBS. Invert to mix. Transfer half (approximately 10 ml) to a 15 ml tube. Centrifuge both tubes for 15 minutes at 300 RCF. Remove as much of the supernatant as possible without disturbing the pellet. Resuspend the pellet in the 50 ml tube with 2 ml of medium suitable for T cells (AIM-V based Medium) or CD34 medium (Stem Pro based medium) as described below and take a viable cell count using the cedex cell counter.

If the blood sample is collected in tubes containing an anticoagulant like EDTA the processing step involves the lysis of red blood cells followed by a Ficoll gradient separation of PBMCs from the blood sample, The sample is initially diluted with equal volume of calcium-magnessium free PBS. The red blood cells are lyzed using the ACK buffer (Invitrogen) according to the manufacturer's' instructions. The cell suspension without the red cells is washed and layered on a Ficoll gradient as described before for the leukopak samples. The PBMCs are obtained from the buffy coat are washed again using calcium-magnesium free PBS and resuspended medium suitable for T cells (AIM-V based Medium) or CD34 medium (Stem Pro based medium).

Example 2

T-Cell Activation and Expansion

Peripheral Blood Mononuclear Cells (PBMCs) were obtained from Biological Specialty Corp (Colmar, Pa.) donor #33231 ("Donor A"). A leukocyte pack was processed with Lymphocyte Separation Medium (Cellgro) to yield PBMCs as described above, which were in turn frozen into aliquots and stored in liquid Nitrogen. Aliquots were thawed and expanded in freshly prepared AIM-V Medium+pen/strep/glutamine (AIV-V/ps/s/g media) (Invitrogen) plus 300 IU/ml rhIL2 (Peprotech) and 10 ng/ml soluble anti-CD3 antibody (OKT3 clone, eBiosciences). Several days after activation exponential growth was verified by CEDEX cell count. After 3 days in culture cells were assayed for T-cell phenotype and then transduced with the reprogramming factors. In one experiment T-cell phenotype was not verified before plating or after transduction. This T-cell activation experiment was repeated multiple times and consistently provided the same result—T-cells made up 90% or more of the culture post activation and post transduction. It was confirmed that it was the T-cells that were transduced with the reprogramming factor(s).

Details of the T-cell activation and expansion procedure (Table 1). PBMC vials were thawed to collect $75 \times 10^6$ cells (approximately 3 vials). The contents of each PBMC vial were added to 7 ml AIM-V/p/s/g media. The cell suspension was centrifuged at 1200 rpm for 4 min. The pellet was resuspended in 10 ml AIM-V +p/s/g. The cell concentration was adjusted to $1 \times 10^6$ cells/ml in a total of 28 ml and $2 \times 10^6$ cells/ml in a total of 25 ml. IL2 (300 IU/ml) and OKT3 (10 ng/ml) were added to cell suspensions and mixed. The cells from each concentration were plated at 1.5 ml per well in a 24-well tissue culture plate and incubated at 37° C. A total of 18 wells of $1 \times 10^6$ cells/ml (1.5 ml/well) and 16 wells of $2 \times 10^6$ cells/ml (1.5 ml/well) were used. Cell counts were verified and recorded as day 0. Day 0 cell counts were compared with day 3 and day 4 counts to verify exponential expansion.

TABLE 1

T-cell Activation and Expansion

| PBMC (T-cell) | Cell Number | Media | Cytokines | Antibody |
|---|---|---|---|---|
| 24 well plate | 1-2 × 10$^6$ cells/well | AIM-V + 1X pen/strep/ glutamine | 300 IU/ml IL2 | 10 ng/ml OKT3 (anti-CD3) - make fresh 10 ng/ ul tube from 1 ug/ul stock in PBS-/- |

Example 3

Retrovirus Production

Retroviral vectors Nanog RFP, Lin28 RFP, Oct4 eGFP, and Sox2 eGFP were constructed as described previously (see U.S. Application No. 61/088,054, incorporated herein by reference). Retroviral vectors c-Myc RFP, Klf4 RFP, Oct4 eGFP, and Sox2 eGFP were constructed similarly. To counteract the possible toxic effects of c-Myc expression, retroviral vector SV40 large T gene (SV40LT)-RFP may be constructed and used in some of the combinations (Yu et al., 2009).

Details of 293T cell preparation procedure (Table 2): cells were seeded approximately 24 hours prior to transfection. The number of cells necessary to yield adequate volumes of viral supernatant for the experiment being performed was calculated. Media were aspirated and 293T plates were washed with 5 ml PBS and then aspirated. 1 ml of 0.05% Trypsin/EDTA per 10 cm plate was added and distributed evenly. The plates were incubated at room temperature for 2-5 minutes, firmly tapped against hand or wall of hood to dislodge cells, and added 4 ml of D10F. 293T cells were triturated (pipet 3-4 times) to ensure single cell suspension and transferred to 15 ml conical tube. 300 ul of 293T cells were removed for counting on CEDEX cell counter. Cell concentration was adjusted to 5×10$^5$ cells/ml in D10F media. Ten ml of cell suspension was plated for each 10 cm plate needed for the experiment (5×10$^6$ cells per plate).

TABLE 2

293T Cell Preparation

| 293T | Cell Number | Viral Supernatant Yield | Media |
|---|---|---|---|
| 10 cm plate | 5 × 10$^6$ | 5 ml | D10F |

Transient Transfection for Retrovirus Production: 293T cells were seeded at 5×10$^6$ cells per 10 cm dish and incubated overnight. The next day the cells were transfected with 10 ug of MMLV retroviral vector, 3 ug of Gag/pol, 1 ug of NFkB, and 1 ug of VSVg using PEI (Sigma) lipophilic reagent and OptiMEM (Invitrogen). 500 ul of OptiMEM was incubated with 40 ul of PEI for 5 minutes. In a separate tube, 10 ug of retroviral vector+3 ug of Gag/pol+1 ug of NFkB+1 ug of VSVg were added to 500 ul of OptiMEM. PEI/OptiMEM mixture was added to DNA/OptiMEM mixture for a total of approximately 1 ml and incubated for 25 minutes. During the incubation, recipient 293T plates were washed with 10 ml PBS-/- and 4 ml DMEM without FBS was added. The DNA/ PEI mixture was added drop-wise directly onto the 293T cells After four hours, the media was exchanged with 5 ml of DMEM/10% FBS/50 mM HEPES and incubated. Forty eight hours after transfection, fluorescence of 293T cells was visualized to confirm high efficiency transfections. The media (5 ml/plate) was collected as virus containing supernatant. Supernatant was filtered through 0.8 um pore size filter and collected for subsequent transduction.

Details of verifying expansion and phenotype of T-cells (about 1 day before reprogramming): T-cells should represent most of the cell population due to the cytokine and antibody addition. Verification was performed by surface staining with anti-CD3, anti-CD4 and anti-CD8 flow cytometry antibody. In addition, cell counts were performed. A lag after thawing was noticed but the cells increased in number from d0; this cell count was recorded and compared with the count next day to verify doubling.

Example 4

Retroviral Transduction of T-cells (Day 0)

Following 3 days of IL2 and OKT3 activation and expansion, the cell population consisted of 97-99% T-cells. These T-cells were resuspended at 1e6 cells/well in a volume of 2 ml DMEM (Invitrogen)+10% FBS (Hyclone) with retrovirus containing media, 300 IU/ml rhIL2 (recombinant human IL-2) and 4 ug/ml polybrene. Retrovirus containing media was prepared by transfection of 293T cells with MMLV packaging elements in combination with one of several transcription factors known to be involved in reprogramming. After preparing the viruses individually, the media were combined in two different cocktails and exposed to T-cells; set one included viruses that express the transcription factors Sox2, Oct4, c-Myc, and Klf-4) and set two used viruses that express Sox2, Oct4, Nanog, and Lin28. Separately, cells were exposed to one of the six viruses to serve as control transductions. The cell culture media was replaced with the virus containing media and the cells were subjected to centrifugation at 1000 g for 1.5 h at 32° C. (spinfection). Subsequently, the cells were incubated for 4 hours at 37° C. Following incubation, 1 ml of media was carefully aspirated and replaced with fresh DMEM+10% FBS Cells were gently triturated to mix and ensure even resuspension. Following trituration the cultures were incubated for 18 h, timed from the beginning of the spinfection. After 18 h the cells were harvested, resuspended in fresh viral supernatant+DMEM with 10% FBS+IL2+polybrene, replated in fresh 24 well plates and spinfected a second time as described above.

Details of the procedure for harvesting retrovirus and transduction of T-cells (DAY 0): In addition to the reprogramming factor, each retrovirus carried a fluorescent protein tag. Thus to confirm a high efficiency of transfection 293T cells were visualized by fluorescence microscopy 48 hours after transfection. 293T media (~5 ml per plate) were collected, centrifuged to remove debris, and the virus-containing supernatants were filtered through 0.8 um syringe filter and placed in separate 15 or 50 ml conical tubes. The virus was stored for 0 to 5 days at 4° C. T-cells were activated and counted on successive days to verify that they were growing exponentially at the time of infection (on day 3). The cells were harvested, centrifuged, resuspended in virus containing supernatant, and seeded to 24-well plates at 1e10$^6$ cells per well. The volume used per well for each virus stock is described in Table 3 (total volume=2 ml)). Six separate control transductions were carried out to verify the infectivity of each individual viral stock. For the latter transductions, 1e10$^6$ cells was resuspended in 500 μl of one of the virus stocks and the total volume was adjusted to 2.0 ml using D10F and 300 IU/ml IL2+4 ug/ml polybrene. All reprogramming trials were performed in duplicate or triplicate. Non-transduced cells were used as a negative control.

TABLE 3

Viral Supernatants for Reprogramming of T-cells

|  | Reprogramming Gene | Volume of Viral |
|---|---|---|
| Set 1 | OCT4 | 500 µl |
|  | SOX2 | 500 µl |
|  | NANOG | 500 µl |
|  | LIN28 | 500 µl |
|  | or |  |
| Set 2 | OCT4 | 500 µl |
|  | SOX2 | 500 µl |
|  | C-MYC | 500 µl |
|  | KLF-4 | 500 µl |

Plates were spinfected at 1000 g for 1.5 hours at 32 degrees with acceleration set to ~4 and brake to ~4. After spin, plates were transferred to an incubator to incubate for 4 hours. After 4 hour incubation, plates were carefully transferred to a hood while making sure not to jostle plates (keep cells settle on bottom of wells). The plates sat in hood for 5 minutes. One ml of media/virus was carefully aspirated from the top of the well using a P1000 pipettor. After adding 1 ml fresh D10F and 300 IU IL2, the plates were incubated 18 hours at 37 degrees. Any unused viral supernatants were stored at 4° C. for second round of infection.

Details of the procedure for second transduction of T-cells (DAY 1): After 24 hours from initial spinfection start (DAY 0), cells in all wells were collected individually in sterile capped FACS tubes and centrifuged at 1200 rpm for 4 minutes. Supernatant was aspirated using fresh 10 ul non-filtered tip on a glass aspirator for each tube/well. Cells were resuspended in appropriate virus(es), IL2, and polybrene as described above. Cells were plated in unused wells of same plate or in a new 24 well plate (wells from first transduction were not reused). Spinfection was followed and steps as described above were repeated.

Details of the procedure for verifying expansion of T-cells (DAY 1): A Cedex cell count was performed on left over well of untransduced sample. At this point the cells were increasing exponentially in number from d0. This cell count was recorded and compared with previous day's counts to verify doubling. This well was retained as a negative control as well as for any further testing. Cells in this well were fed with half-media exchanges plus 300 IU IL2/ml as needed.

Example 5

Plating Transduced T-Cells on MEFs

MEF Plating: MEFs were plated on gelatin coated 6 well plates or 10 cm dishes 1-3 days prior to introducing the transduced cells or iPS colonies (plating MEFs one day prior to transduction may be optimal).

Verification of T-cell Expansion and Transduction Efficiency: T-cell identity was verified 2-3 days after activation by flow cytometry surface staining with anti-CD3, anti-CD4, and anti-CD8, as well as post-transduction to verify the cell populations that were transduced successfully. CEDEX cell counts were conducted on days 0, 2, 3 and 4 to confirm exponential expansion and thus amenability to MMLV retroviral infection.

Plating Transduced T-cells on MEFs: At day 3 post initial transduction success and efficiency estimates were verified by fluorescent microscopy and flow cytometry as listed above. Transduced cells were added in two cell concentrations ($5 \times 10^6$ and $2 \times 10^6$) to 10 cm dish MEF plates in a 50:50 media combination of D10F:hES w/o FGF (no added IL2 or other cytokines). Cells were incubated and fed every other day.

Details of the procedure for plating irradiated MEFs: MEFs were plated 1-3 days prior to introducing the transduced cells. The number of 10 cm plates needed was calculated (500 k transduced cells per 10 cm plate; transcription factors (set 1 or set 2), untransduced control, c-Myc only control, MEF only control—5 plates+). 0.1% gelatin was used to coat 10 cm plates for at least 1 hour and then aspirated. 15 ml of irradiated MEF cell suspension (~$7.5 \times 10^4$ cells/ml) was added onto each 10 cm plate. Cells were checked the following day to ensure MEFs had attached.

Details of the procedure for transfer of transduced T-cells to irradiated MEFs (DAY 3): A fluorescent microscope was used to verify transductions. A Flow cytometer was used to verify transduction and determine transduction efficiency. A minimum 20% efficiency is considered to be the requirement to proceed with reprogramming (plating onto MEFs, etc). GFP/RFP analysis and surface staining were performed to verify transduction of T-cells was independent from other cell populations. 100 ul of cells were collected in FACS tubes and spun at 1200 rpm for 4 min. The supernatant was aspirated, and cells were resuspended in 5 ml FACS Buffer and centrifuged again. The pellet was resuspended in 150 ul FACS buffer, and stained with anti-CD3, anti-CD4 or anti-CD8 flow cytometry antibodies. Cells were analyzed on flow cytometer, to verify CD3$^+$ cells (T-cells) were transduced what the transduced subsets were. Media were aspirated from irradiated MEF plates and 7.5 ml DMEM+10% FBS was added. $5 \times 10^5$ transduced T-cells were collected, centrifuged at 1200 rpm for 4 minutes, and resuspended in 7.5 ml hES medium without bFGF. T-cells were added dropwise to irradiated MEF plates. No IL2 or other cytokines was added. Then the MEF plates were incubated at 37 degrees.

Example 6

Maintenance and Feeding of MEF-Plated Transduced Cells

Days 5-9: Half-media exchanges were performed for each reprogramming 10 cm plate with hES media (CM) supplemented with 100 ng/ml of zebrafish FGF. A novel feeding strategy was developed to minimize suspension cell loss while maximizing the positive effects of replenishing of media. Briefly, five 10 cm dish lids were used (and reused for all subsequent feedings) as props to angle dishes. Dishes were carefully removed from the incubator so as to not disturb any loosely adherent cells. Plates were set on reserved lids at an angle but with no MEFs/cells exposed. Cells were allowed to settle for 10 minutes. After settle period each lid was removed and 7.5 ml was carefully/slowly aspirated from the very top of the media horizon on the bottom of the plate. Less than 1% cell loss was verified by collecting this removed media, centrifuging at 1200 rpm×4 min, resuspending in 1 ml media and counting on CEDEX. 7.5 ml of fresh media was then added dropwise in a circular motion being careful not to disturb cells, and dishes were placed back in incubator. This method served the purpose of minimizing cell loss while allowing regular media changes. Days 9-30: Half-media exchanges were performed for each reprogramming 10 cm plate with MEF-conditioned hES media (MEF-CM) supplemented with 100 ng/ml of zebrafish bFGF.

Details of the procedure for maintenance and feeding schedule (DAY 5-30): Days 5-9: Half-media exchanges were performed for each reprogramming 10 cm plate with hES media (CM) supplemented with 100 ng/ml of zebrafish FGF. Five 10 cm dish lids were gathered to be used for all subsequent feedings as props to angle dishes. 10 cm reprogramming dishes were removed from incubator and set on reserved lids so that plates were at an angle but with no MEFs/cells exposed (media should still be covering the entire surface, pooling at the bottom, and not spilling). Dishes were settled for 10 minutes. After settle period each lid was removed, and 7.5 ml supernatant was carefully/slowly aspirated from very top of the media horizon on the bottom of the plate. The supernatant or aspirated medium was collected, centrifuged 1200 rpm×4 min, resuspended in 1 ml media and counted on CEDEX. It was verified that less than 1% of the cells were lost. 7.5 ml of fresh media were added dropwise in a circular motion being careful not to disturb cells, place back in incubator. Feeding regimen began every other day for reprogramming plates. Days 9-30: Half-media exchanges were performed for each reprogramming 10 cm plate with MEF conditioned hES Media (MEF-CM) supplemented with 100 ng/ml of zebrafish FGF. Feeding was proceeded with this medium as in Days 5-9.

Example 7

Identifying and Picking iPS Colonies

Activated and expanding T cells displayed characteristic cell morphology and clustering behavior. Detection of retroviral transduction efficiency was determined by GFP and RFP expression 72 h post initial transduction, over the course of ~3 weeks the transgenes were silenced and display an hES cell phenotype. Well defined iPS cell colonies began to appear on day 23. GFP and RFP silencing was verified by fluorescent microscopy and colonies were picked in a dissecting hood using a pipette tip. Colony pieces were then transferred to fresh 6 well plates of irradiated MEFs. The number of colonies were counted to estimate reprogramming efficiency given the number of input plated cells. From this point clonal colonies were fed daily and manually passaged one more time and then expanded as described in detail below.

Details of the procedure: Morphologically, iPS cell colonies were dense and comprised of small, compact cells with enlarged nuclei and 2 distinct nucleoli. Borders of colony were usually defined. iPS colonies had the GFP and RFP expressed from the integrated viral DNA silenced. Some bona fide colonies lost fluorescence by ~20 days post transduction and some lost fluorescence after they had been picked and transferred ~35-40 days post-infection. All colonies were lacking GFP and RFP expression (though some expression was noted in single cells near by) in the colonies observed here. This may vary among cell type, particularly as compared to fibroblasts. To pick manually, a pipet tip was drawn in a "tic tac toe board" fashion directly on the colony to break it up into 3-6 pieces to increase the probability of freeing stem cells from the surrounding MEF and T-cells. Picking was avoided until multiple colonies have formed so as to avoid confounding counts of total colonies, i.e., if a small chunk of a colony was left, it might resettle and was falsely counted as a new clone. Cells were then transferred directly into a recipient well of a 6 well plate containing MEFs with hES media and 100 ng/ml zebrafish bFGF. Proliferation, morphology, and loss of fluorescence were then monitored for 1-2 weeks to be confident that clones were indeed fully reprogrammed. The cells were fed daily after one day of no feeding following picking After the picked and plated colonies adhered and displayed characteristic ES-like morphology, these ES-like colonies were manually picked as described above again onto a new set of 6 well irradiated MEF plates and fed daily. As wells became confluent, the cells were passaged as normal iPS cell lines with 1 mg/ml collagenase (Yu, et. al., 2007). iPS cells were frozen down at various passages, and test thaws performed on each set.

Clonal iPS colonies formed d23-30=21 colonies (all from set 1 factors as of d30), 7 from high transduced-cell seeding density ($2 \times 10^6$ per 10 cm dish) and 14 from low density ($5 \times 10^5$ per 10 cm dish). Dishes were fed until it was determined that no additional colonies would grow out. A total of iPS lines were obtained, frozen and expanded.

Example 8

Figure 2A:
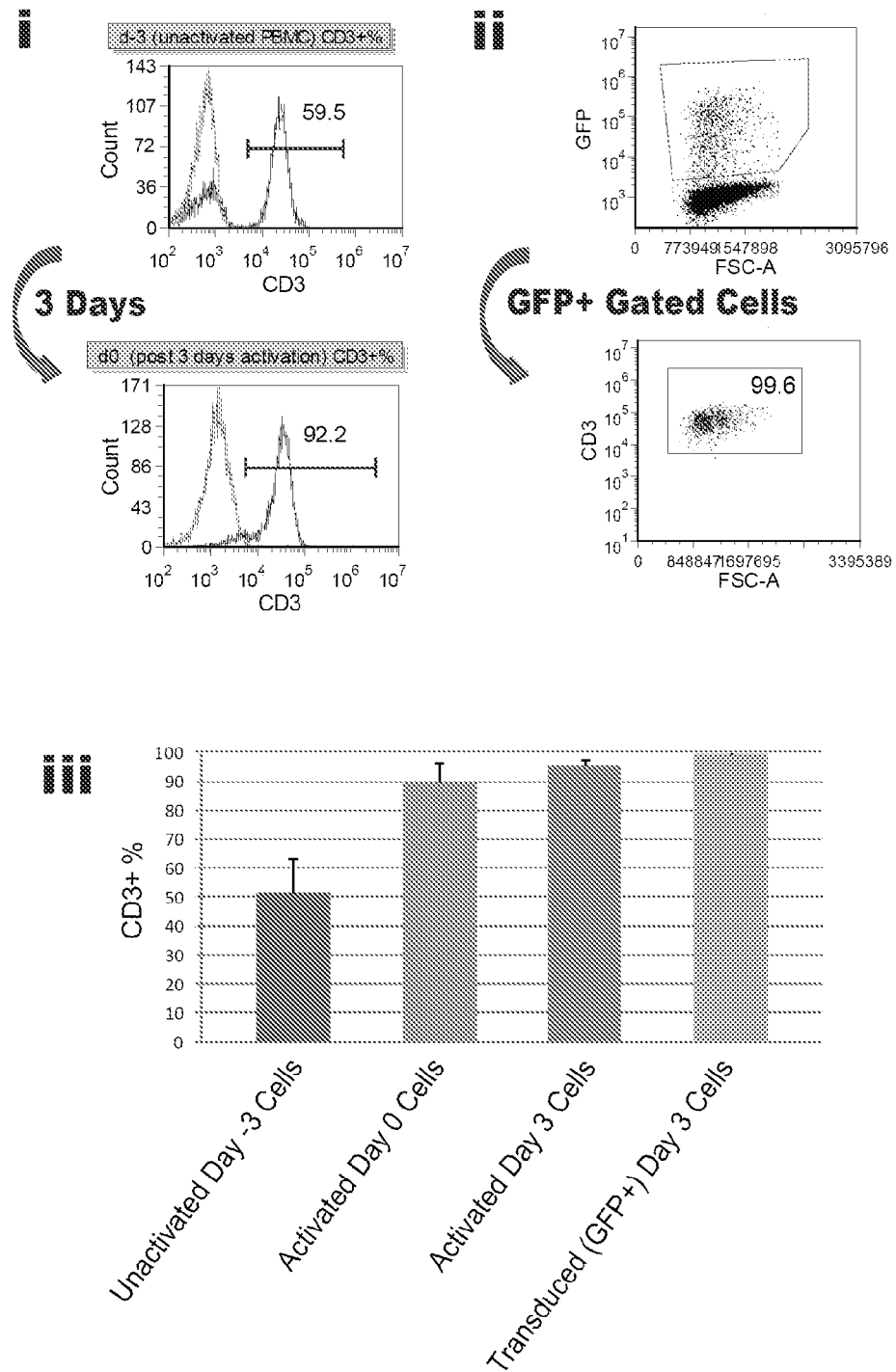
FIGS. 2A-2C: Derivation and characterization of induced pluripotent stem cells from human T-cells.

Derivation of Induced Pluripotent Stem Cells from Human Peripheral Blood T Llymphocytes Activated T-cell enriched populations containing $1 \times 10^6$ cells were subjected to two rounds (at day 0 and 1) of retroviral transduction with four separate vectors, each encoding one of the reprogramming factors (SOX2, OCT4, c-Myc, or KLF4) linked to a fluorescent marker gene (a representative vector map is shown in FIG. 10). Transduction efficiency was assessed at day 3 by fluorescence microscopy and flow cytometry. Staining for CD3 showed the transduced population to be 99%+/−1% $CD3^+$ (FIG. 2A).

T-cells are well suited as a starting material for reprogramming due to their abundance in whole blood (~$6.5 \times 10^5$-$3.1 \times 10^6$/ml in healthy adults) (Lichtman and Williams, 2006) and ease of culture using well-established protocols (Johnson et al., 2009; Morgan et al., 2006). To facilitate T-cell proliferation and efficient retroviral transduction, peripheral blood mononuclear cells (PBMCs) were isolated from a leukapheresis or a standard venipuncture (Vacutainer© CPT tube) to be reprogrammed into iPS cells (FIG. 1). PBMCs from a non-mobilized donor were activated with anti-CD3 antibody and expanded in the presence of IL-2 in serum-free media (FIG. 2A). This led to preferential expansion of mature $CD3^+$ T-cells consisting of an average day 3 $CD3^+$ purity of 90%+/−7% (FIG. 2A).

The population which was skewed predominantly towards T cells was then transduced with the reprogramming factors. The population of cells containing the transduced T-cells was placed on irradiated mouse embryonic fibroblasts (MEFs) in hESC medium supplemented with 100 ng/ml basic fibroblast growth factor (bFGF). iPSC colonies were observed beginning at day 23. Reprogramming efficiencies of T-cells were estimated by dividing the number of colonies with hESC-like morphology by the input number of transduced cells and determined to be approximately 0.01%, similar to published fibroblast and $CD34^+$ cell reprogramming efficiencies (Yu et al., 2007; Loh et al., 2009).

TiPS were generated from both leukapheresis samples (from a male Hispanic adult, lines denoted "TiPS-L") and whole blood Vacutainer© samples (from a male Caucasian adult, lines denoted "TiPS-V"). In each case, reprogramming was achieved using an input cell number equivalent to the amount of T-cells in 1 ml whole blood. Colonies displaying hESC morphology were expanded on MEFs and the clones were successfully maintained under feeder-free conditions using mTeSR media and Matrigel coated plates.

Figure 2B:
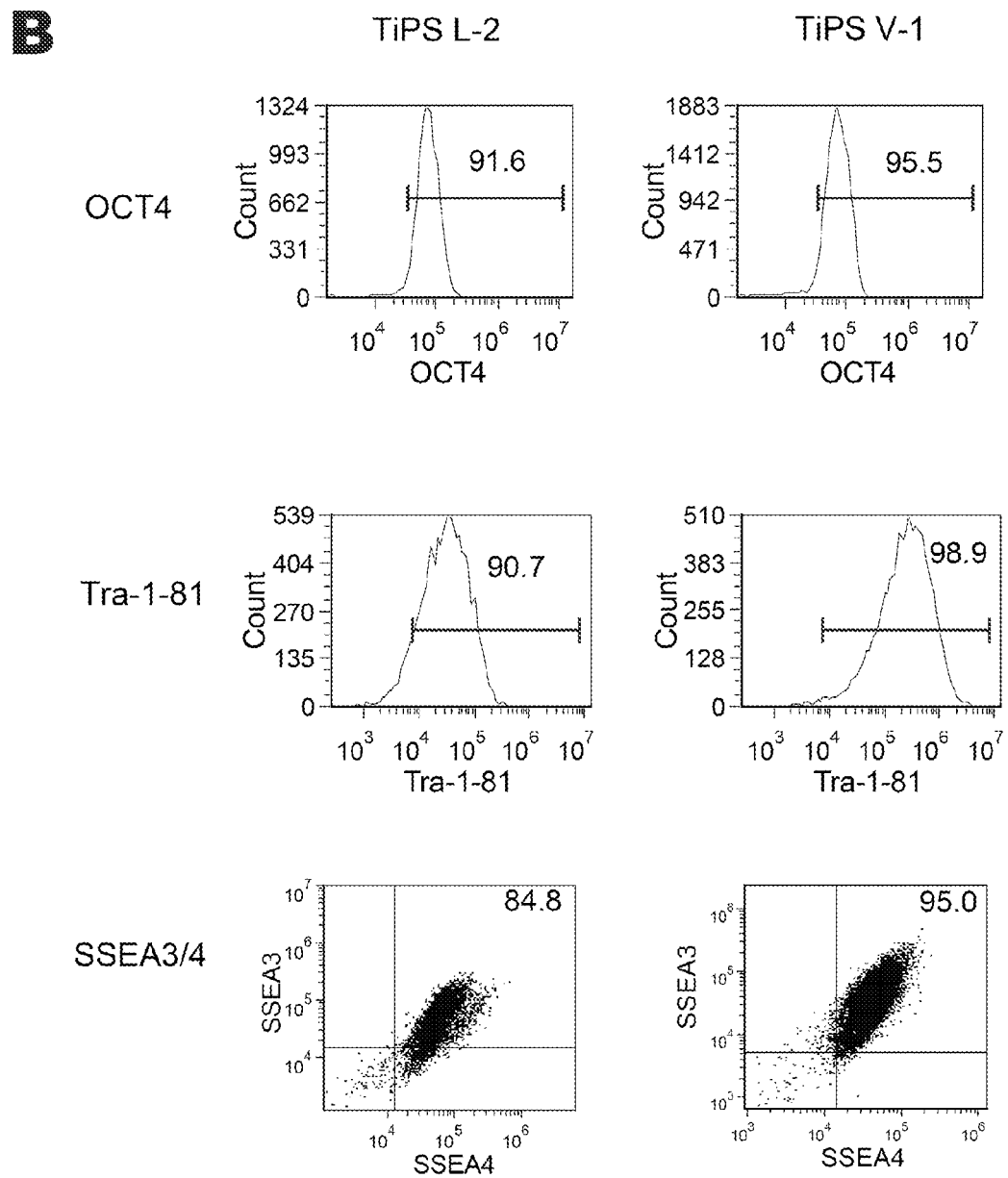

Pluripotency was verified by expression of hESC pluripotency markers SSEA-3, SSEA-4, Tra-1-81, and OCT4 using flow cytometry (FIG. 2B) and alkaline phosphatase staining (FIG. 8).

DNA fingerprinting was also performed to verify that TiPS shared a genetic background with the starting donor T-cell population and to rule out cell line cross-contamination (FIG. 7). STR (short tandem repeats) analysis showed that the iPS colonies were derived from the donor's genetic material. The donor PBMC and the iPS line were male gender specific and are identical to each other for 15 allelic polymorphisms across the 8 STR loci analyzed (Table 4, below).

TABLE 4

Confirmation of Cell Identity via Polymorphisms

| Locus | Repeat # | TiPS1ee | PBMC Donor A | Fib-iPS |
|---|---|---|---|---|
| D16S539 | 5, 8-15 | 11, 12 | 11, 12 | 10, 13 |
| D7S820 | 6-14 | 8, 10 | 8, 10 | 9, 12 |
| D13S317 | 7-15 | 8, 12 | 8, 12 | 11, 13 |
| D5S818 | 7-15 | 12, 13 | 12, 13 | 12, 13 |
| CSF1PO | 6-15 | 12, 12 | 12, 12 | 11, 13 |
| TPOX | 6-13 | 9, 11 | 9, 11 | 8, 9 |
| Amelogenin | NA | X, Y | X, Y | X, X |
| TH01 | 5-11 | 7, 9 | 7, 9 | 8, 9.3 |
| vWA | 11, 13-21 | 16, 18 | 16, 18 | 16, 19 |

Figure 2C:
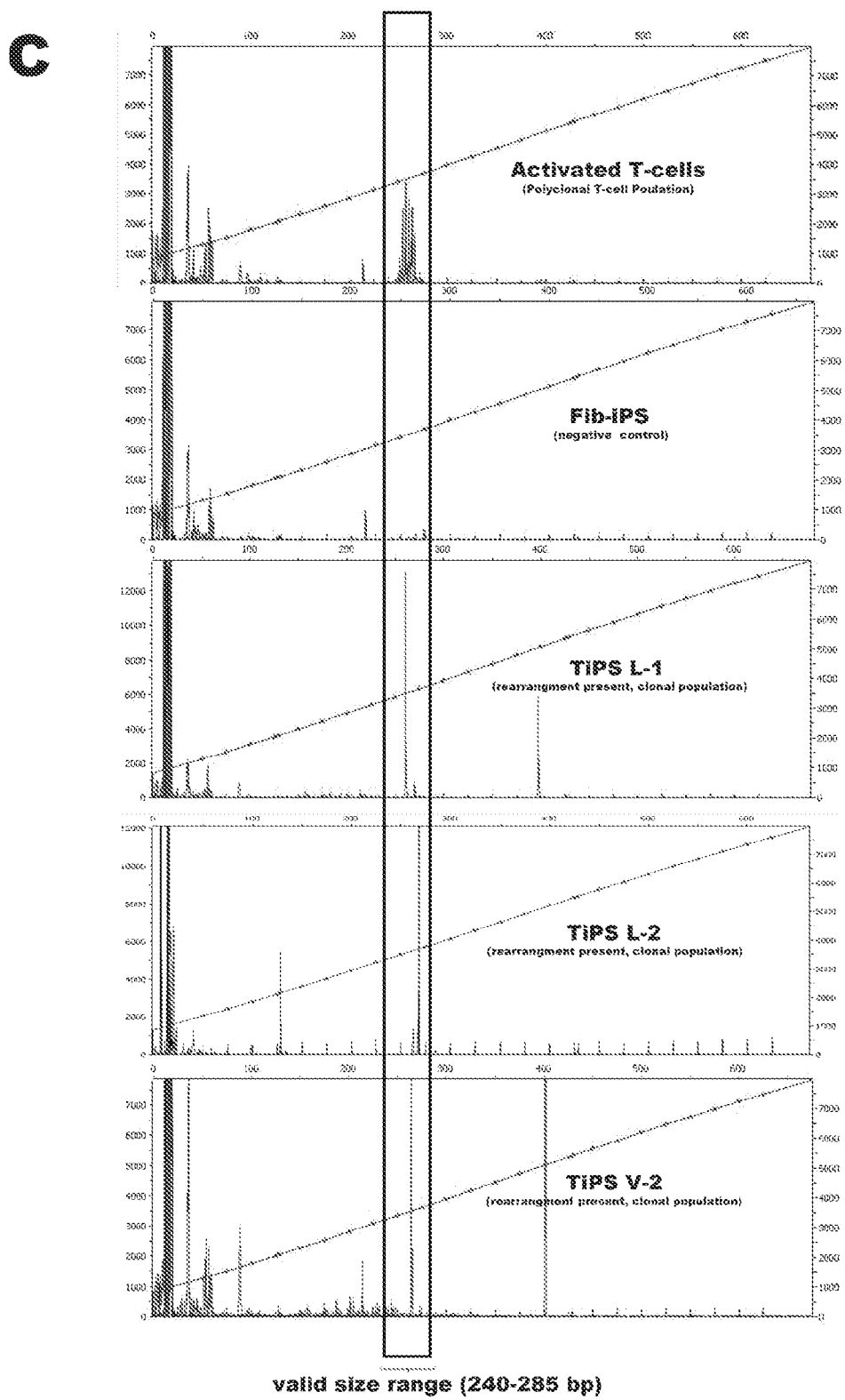

The TiPS lines' T-cell origin via multiplex PCR detection of TCR 0 chain rearrangements was confirmed (FIG. 2C). T cells have a single productive V-J rearrangement in the TCR beta chain and should retain this characteristic gene sequence after becoming TiPS cells; using a master mix combining various primers for the most common beta chain rearrangements PCR amplification showed one band of unique size and sequence as determined by fragment analysis electropherogram on an ABI 3730 DNA analyzer. iPS cells derived from fibroblasts, "Fib-iPS" were used as a negative control.

Figures 3A, 3B:
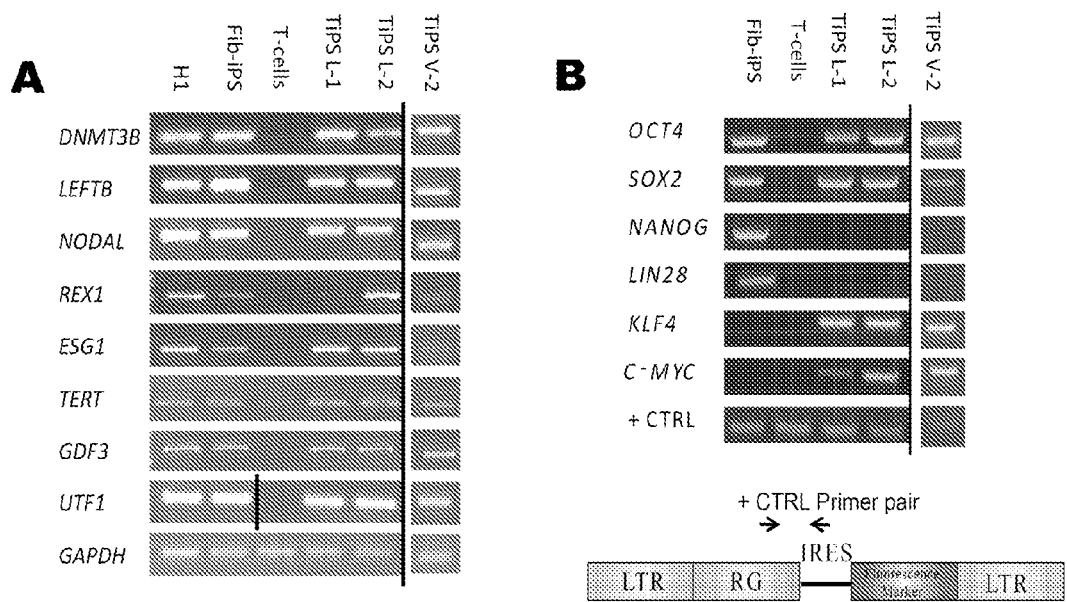
FIGS. 3A-3D: Characterization of induced pluripotent stem cells from human T-cells.
Figure 3C:
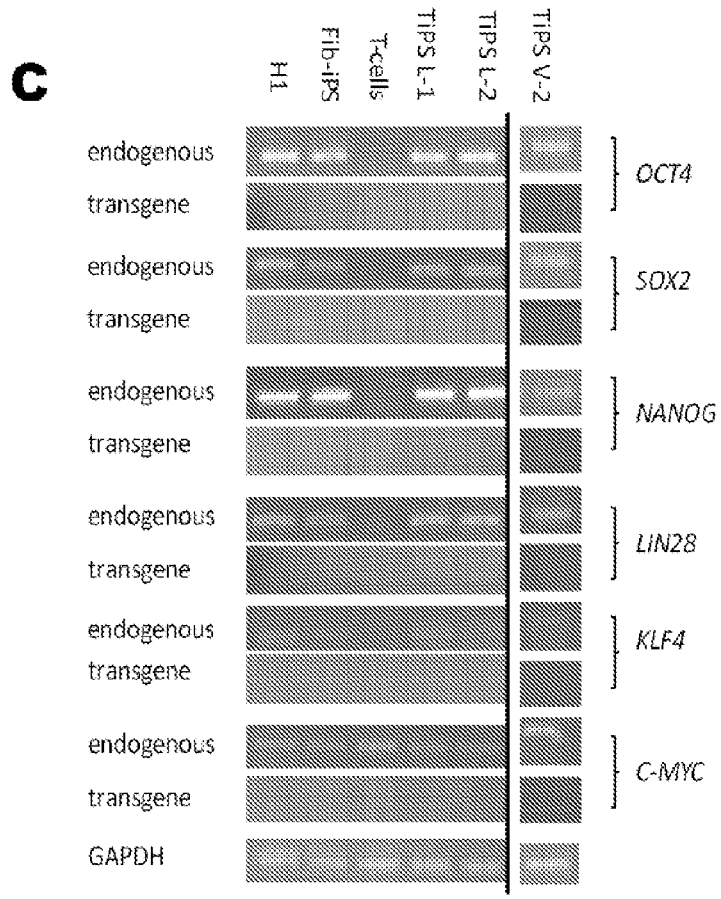

TiPS clones expressed human embryonic stem cell marker genes DNMT38, LEFT8, NODAL, REX1, ESG1, TERT, GDF3, and UTF1 (FIG. 3A). Total RNA was isolated from H1 hES cells, Fib-iPS (derived from fibroblasts), T-cells from the primary donor, and TiPS clones TiPS1ee and TiPS1b were analyzed using RT-PCR. Further characterization demonstrated integration of the transgenes into the host genome as well as their silencing following successful reprogramming (FIGS. 3B-3C). TiPS were similar to both the hESC line H1 and to fibroblast-derived iPSC line controls in all of the above assays. Endogenous and exogenous (transgene) expression of reprogramming genes showed complete reprogramming as evidenced by silencing of transgene expression (FIG. 3C). GAPDH was used as amplification control in both A+B. Genomoic DNA was isolated and analyzed by PCR to confirm integration of reprogramming genes by using forward primers for the gene of interest and reverse primers for the IRES (FIG. 3B). OCT4 forward and reverse primers were used as a PCR reaction control.

Figure 3D:
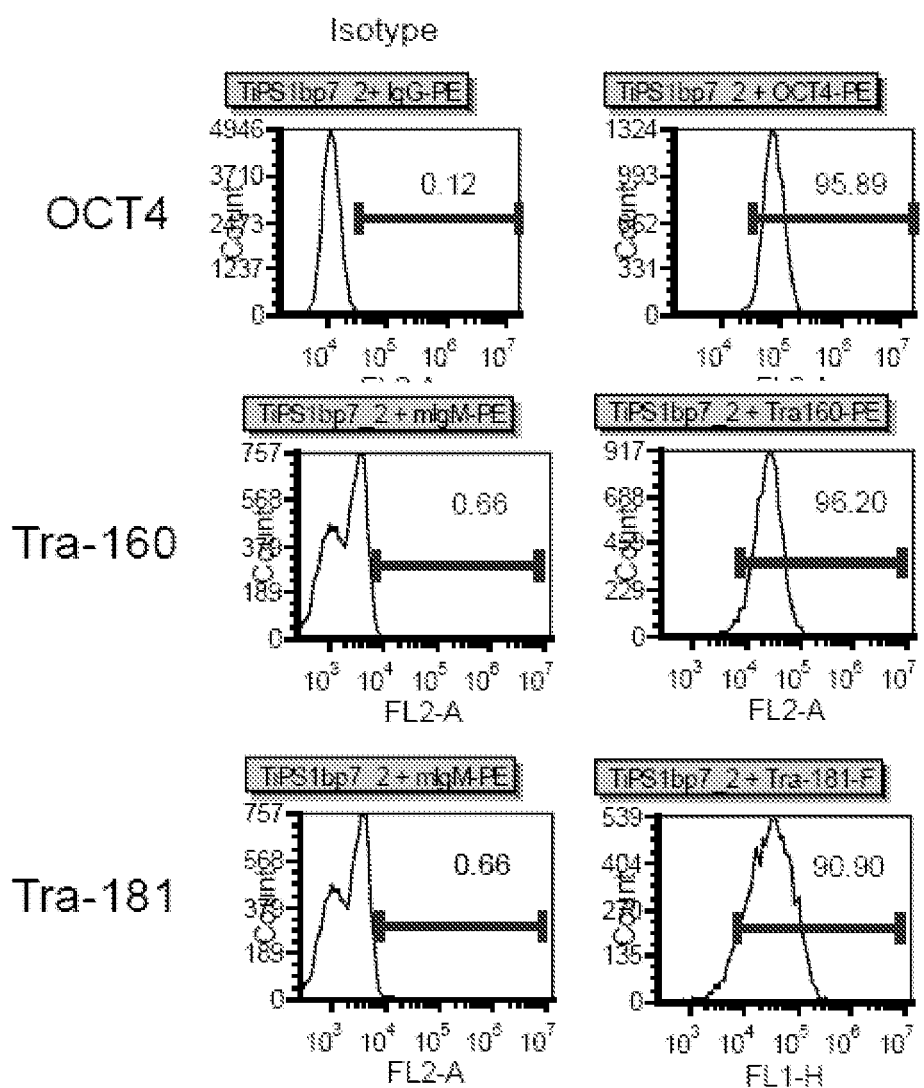

TiPS clones expressed human embryonic stem cell-specific pluripotency markers as shown by flow cytometry analysis (FIG. 3D), Alkaline Phosphatase staining, and karyotipic analysis by Gbanding chromosome analysis. Lines were karyotypically normal after multiple passages and have been propagated for over 30 passages in culture while retaining a normal karyotype (FIG. 9).

Figures 4A, 4B:
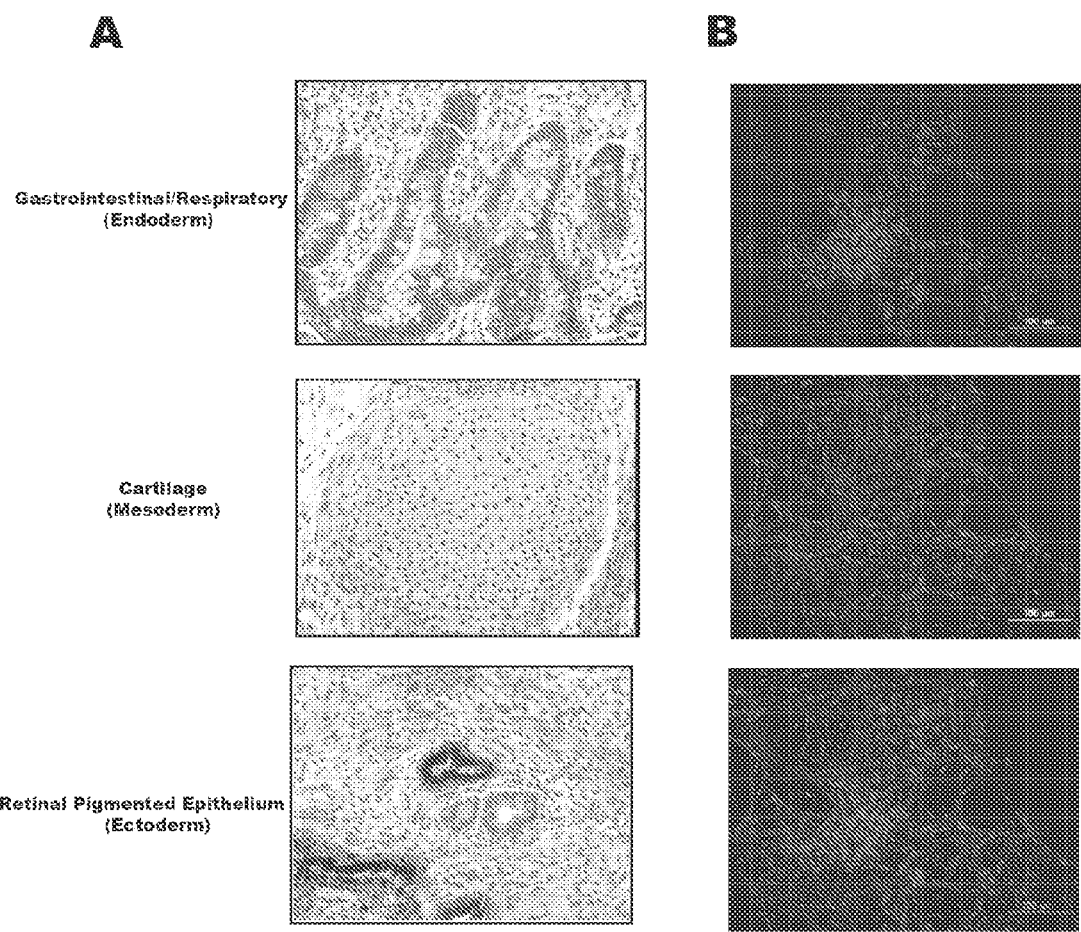
FIGS. 4A-4E. in vivo and in vitro differentiation potential of TiPS cell lines.

Finally, the TiPS cell lines were evaluated to determine their in vivo and in vitro differentiation potential. TiPS clones formed teratomas containing tissue consistent with derivation from all three primary germ layers (FIG. 4A). The cell lines were also assessed for their capability to differentiate in vitro into ectodermal and mesodermal lineages in various directed differentiation protocols. The clones were able to generate neurons, beating cardiac troponin T-positive cardiomyocytes and multipotent granulocyte-erythroid-macrophage-megakaryocyte (GEMM) hematopoietic cells (FIGS. 4B-4E).

Figure 4C:
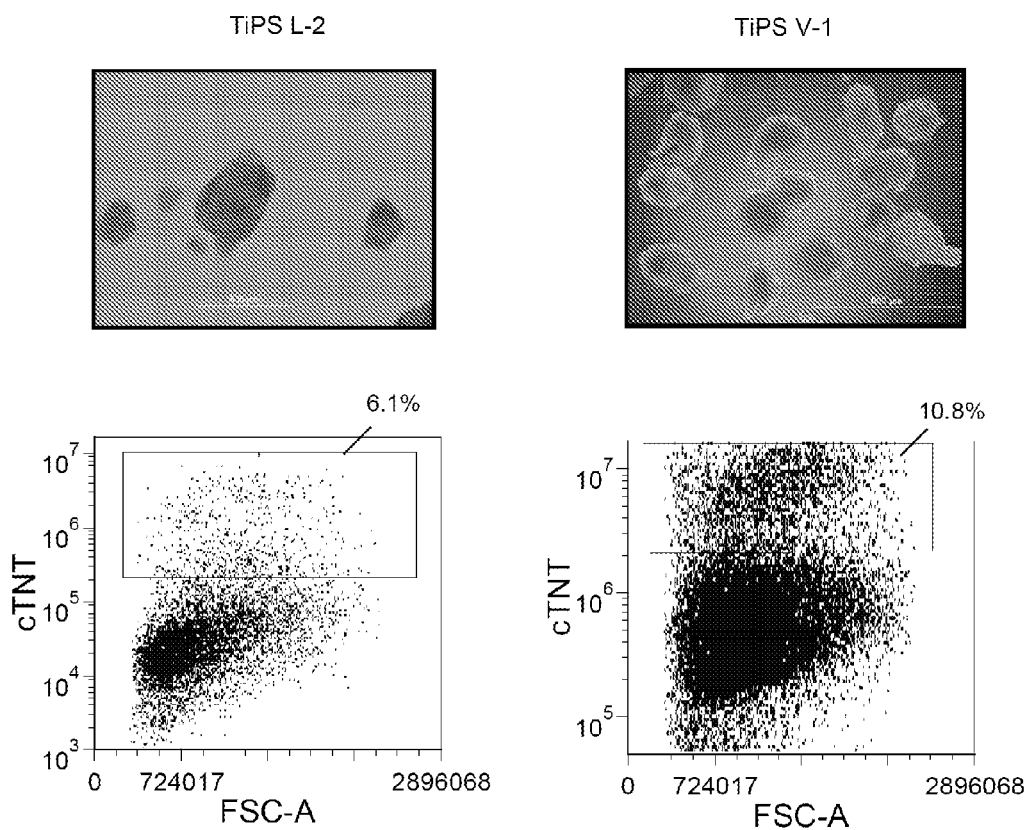

TiPS were differentiated into multiple cell types. TiPS were differentiated into cardiomyocytes by the following method. TiPS clones formed embryoid bodies (EBs) and were differentiated into cardiomyocytes via HGF/bFGF mediated cardiac induction (FIG. 4C). Beating cardiomyocyte aggregates were observed on day 14. TiPS were also differentiated into blood (FIG. 4E). Hematopoietic progenitor cells (HPCs) were derived from EBs using a combination of BMP-4, VEGF, Flt-3 ligand, IL-3, GM-CSF and FGF-2. Functional capability of TiPS1ee-derived HPCs was determined using the colony-forming unit (CFU) assay. CFU-GM, BFU-E, and CFU-GEMM colonies were observed at day 12.

In summary, iPS cells were successfully generated from T cells derived from the peripheral blood of a non-mobilized donor. The amount of starting material was adaptable to 1 ml of starting material from a standard vacutainer. TiPS reflected the identity of the host material. TiPS also harbored hallmark characteristics of normal human ES cells and iPS cells derived from other cell sources. TiPS were further differentiated into multiple cell types, including beating cardiomyocyte aggregates and blood cells.

Figure 4D:
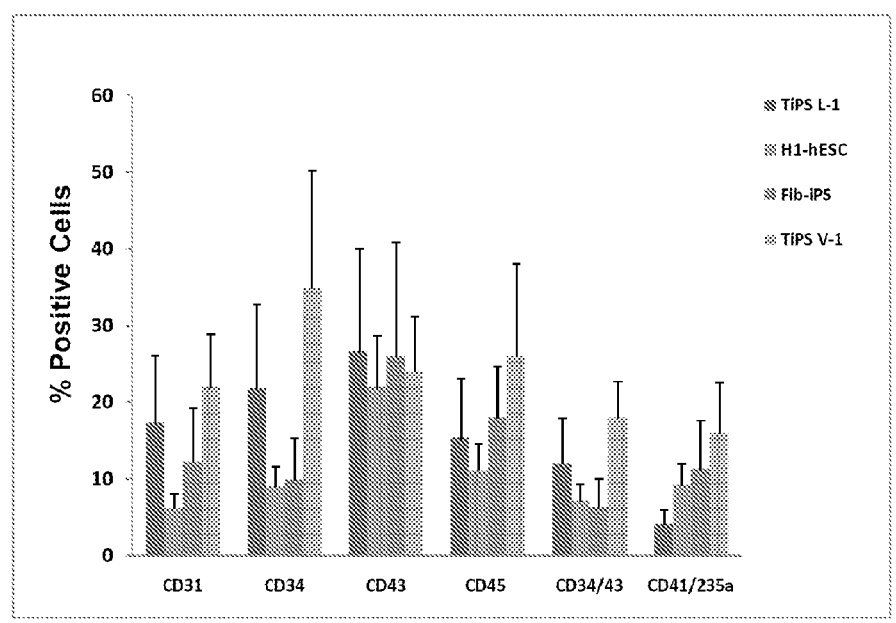
Figure 4E:
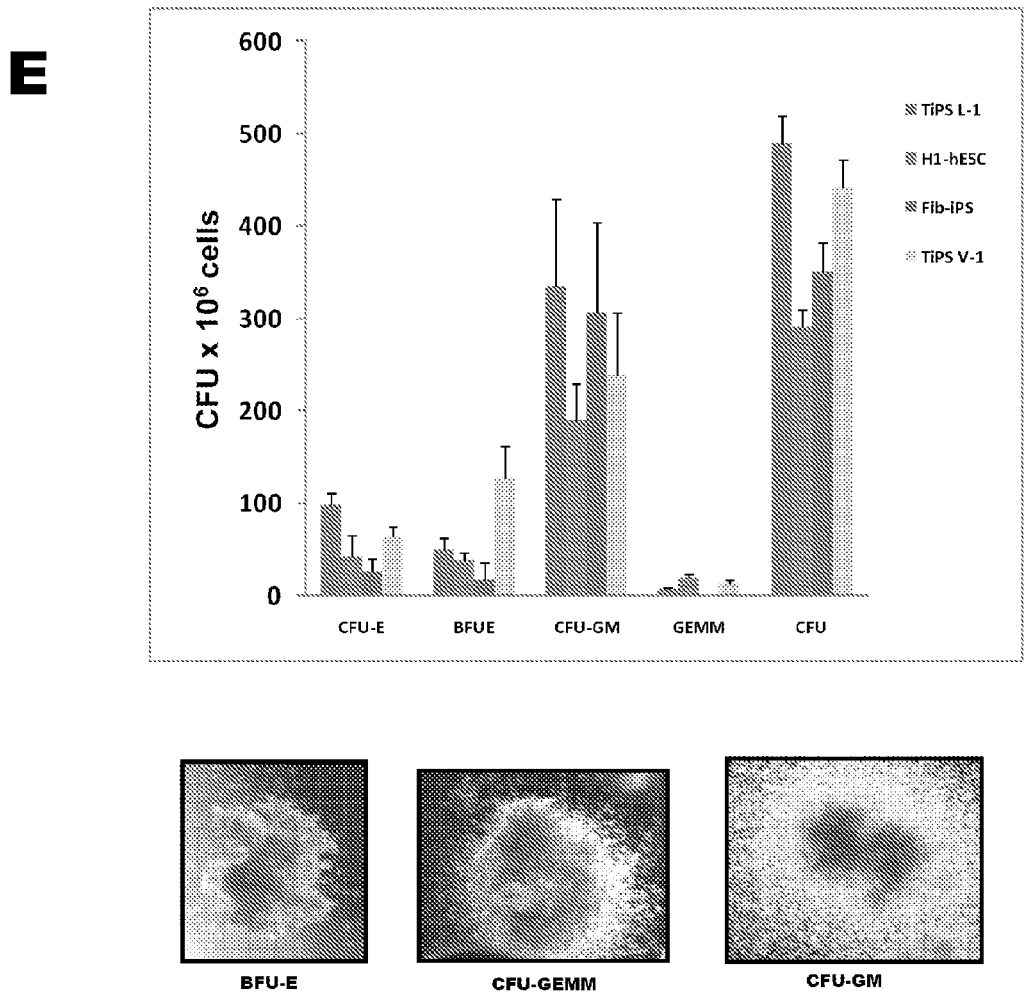

No significant differences in differentiation potential between TiPS clones and hESC lines or fibroblast-derived iPSC lines were observed (FIGS. 4D-4E). The potential effect of the persistence of TCR gene rearrangements in the iPSC genome on subsequent differentiation may be tested.

Figure 5:
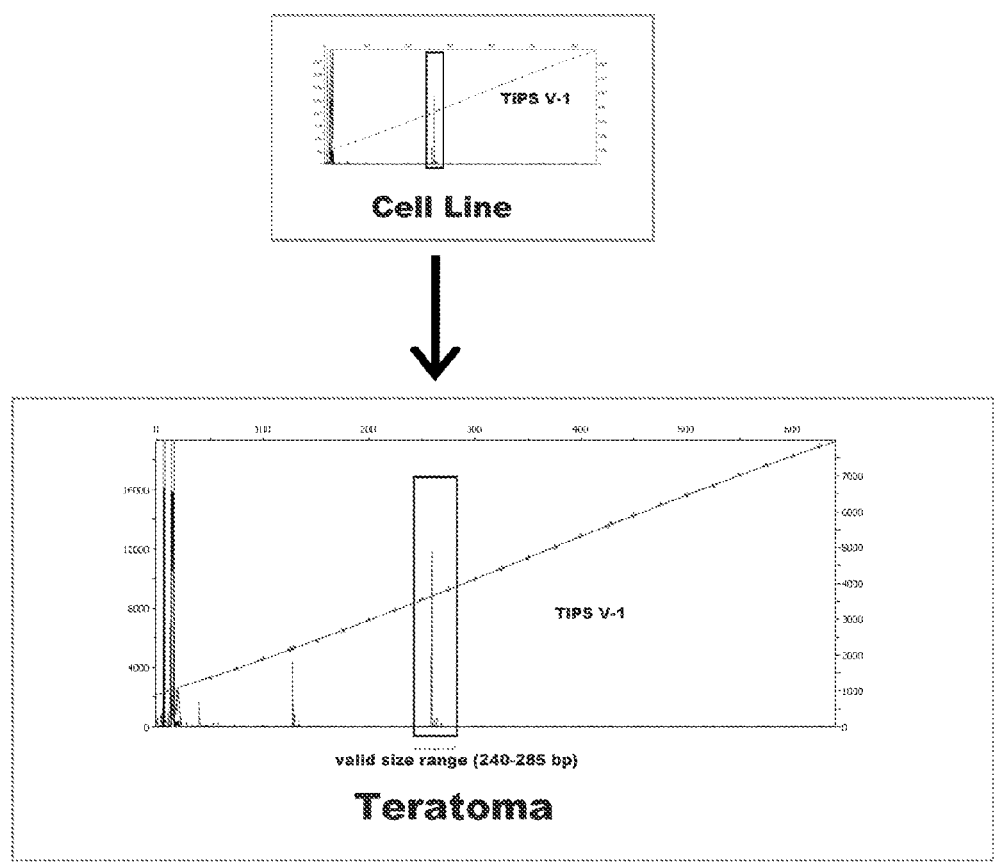
FIG. 5. iPSC Clone Tracking. Genomic DNA was isolated from teratoma samples and compared with their parent cell lines for TCR β chain rearrangements. Representative data is shown from cell line TiPS V-1. The derivative teratoma harbors the clonal rearrangement of the parent cell line. PCR analysis was conducted using multiplexed primers targeted to conserved regions within the V-J region of the TCR β locus. DNA fragment analysis was performed on an ABI 3730 DNA analyzer. Background≤1000 RFU.

TCR rearrangements may in fact prove advantageous in certain contexts, such as for iPSC clone tracking, as demonstrated by the detection of parent line clonal TCR β chain rearrangements in derivative teratomas. (FIG. 5). Further, upon re-differentiation into T-cells TiPS cells may bypass key steps in the canonical thymic development sequence due to the mechanism of TCR allelic exclusion caused by the expression of their pre-rearranged TCR genes. This phenomenon could be explored in T-cell development studies.

It should be noted that insertional mutagenesis and other potential disruptions of cellular function are possible when using a retroviral reprogramming protocol (Mirxhwll et al., 2004). Recent advances in using episomal reprogramming methods may address these issues and efforts are in progress to reprogram T-cells via these alternative methods (Yu et al., 2009; Zhou et al., 2009). Further, an interesting example of a potential therapeutic use for such episomally reprogrammed TiPS cells is as a source to differentiate integration-free hematopoietic stem cells bearing endogenous TCR genes specific for tumor-associated antigens (van Lent et al., 2007).

Previous reports of reprogramming terminally differentiated B lymphocytes in mice required the addition, or knock-down, of cellular identity-associated transcription factors and used a doxycycline-inducible expression system (Hanna et al., 2008). Recently, a description of reprogramming murine T-cells was published necessitating a p53 gene knock-out for successful iPSC generation (Hong et al., 2009). Experiments involving manipulation of anti-proliferative pathways (Li et al., 2009; Marion et al., 2009; Kawamura et al., 2009; Utikal et al., 2009) offer insights into the mechanisms of reprogramming and may significantly augment reprogramming efficiencies. However, none of the above mentioned manipulations appear to be a requirement for successful viral reprogramming of human T-cells. Additionally, our data, coupled with methodologies used in reprogramming adult CD34+ hematopoietic progenitor cells (Loh et al., 2009; Ye et al., 2009), now afford a primary, human system to examine recent observations in the mouse system correlating differentiation stage of input cells with reprogramming efficiency (Eminli et al., 2009).

The derivation of iPSCs from small, clinically advantageous volumes of non-mobilized human peripheral blood was discovered. T-cells represent an abundant cell source for reprogramming which can be harvested from large numbers of donors in a minimally invasive manner and cultured via well-established protocols. In the experiments TiPS were found to have similar characteristics and differentiation potential as hESC lines and fibroblast-derived iPSC lines. Additionally, TiPS provide a novel model with which to explore iPSC clone tracking, T-cell development and therapeutic applications of iPSC technology.

Materials and Methods

Cell Growth Media and Basic Fibroblast Growth Factor— iPSC lines were maintained using previously described methods (Yu et al., 2007). Zebrafish bFGF was substituted for human bFGF in all experiments, as previously described (Ludwig et al., 2006a).

Fibroblast iPSC Lines—

Control fibroblast-derived iPSC lines, referred to as "Fib-iPS", were produced as previously described using IMR90 cells obtained from ATCC (Manassas, Va.) (Yu et al., 2007).

T-cell Activation and Expansion—

Peripheral Blood Mononuclear Cells (PBMCs) were obtained from an HLA-A2 positive male Hispanic adult donor ("Donor L") leukocyte pack (Biological Specialty Corp, Colmar, Pa.) processed with Lymphocyte Separation Medium (Cellgro, Manassas, Va.). Additionally, whole blood samples were collected from a male Caucasian donor of unknown serotype ("Donor V") via standard venipuncture in a Vacutainer© CPT™ tube (BD Biosciences, San Jose, Calif.) and PBMCs collected by centrifugation according to the manufacturer's recommendations. Blood samples were obtained with written informed consent in accordance with the Declaration of Helsinki and Institutional Review Board approval from the Biological Specialty Corporation (Colmar, Pa., USA). T-cells were expanded in freshly prepared AIM-V Medium (Invitrogen, Carlsbad, Calif.) supplemented with pen/strep/glutamine (Invitrogen) plus 300 IU/ml rhIL2 (Peprotech, Rocky Hill, N.J.) and 10 ng/ml soluble anti-CD3 antibody (eBioscience, OKT3 clone, San Diego, Calif.) (Chatenoud, 2005; Berger et al., 2003). Proliferation was verified by CEDEX (Roche Innovatis, Bielefeld, Germany) cell count after 3 days in culture at which point cells were assayed for T-cell phenotype and then transduced with reprogramming factors.

Transient Transfection for Retrovirus Production—

Retrovirus was generated by transfecting 293T cells in a 10 cm plate at 70-80% confluence with 10 ug of retroviral vector (Moloney Murine Leukemia Virus) backbone encoding each of 4 reprogramming genes and a fluorescent marker gene (GFP or RFP), 3 ug of Gag-Pol, 1 ug of plasmid encoding a derivative of NFkB, and 1 ug of Vesicular Stomatitis Virus G protein using polyethylene imine ("PEI") lipophilic reagent (40 ug/10 cm plate). After four hours, the medium was exchanged with 5 ml of DMEM (Invitrogen) plus 10% FBS (Hyclone, Waltham, Mass.) and 50 mM HEPES (Invitrogen). Viral supernatant was collected 48 hours post-transfection, centrifuged, and passed through a 0.8 um pore size filter.

Retroviral Transductions via Spinfection—

One million activated donor cells per well were "spinfected" via centrifugation for 1.5 h×1000 g at 32° C. in a mixture of the four retroviral supernatants plus 4 ug/ml polybrene (Sigma-Aldrich, St. Louis, Mo.), and 300 IU/ml rhIL-2 After spinfection the plates received a half-media exchange, and were incubated overnight. The next day the cells were harvested by centrifugation and spinfected a second time.

Verification of T-cell Expansion and Transduction Efficiency—

T-cell identity was verified 3 days after activation by flow cytometry surface staining with anti-CD3 antibodies (BD, clone HIT3a), as well as post-transduction to verify which cell population was transduced successfully. Samples were run on an Accuri (Ann Arbor, Mich.) flow cytometer. CEDEX cell counts were conducted on days 0, 3 and 4 to confirm expansion and thus amenability to MMLV retroviral infection (data not shown).

Plating Transduced T-cells on MEFs—

Seventy two hours post initial transduction, transduction success and efficiency estimates were verified by fluorescent microscopy and flow cytometry as listed above. $5 \times 10^5$ transduced cells were added to 10 cm plate seeded with MEFs 1 to 3 days prior in a 50/50 media combination D10F:hESC without zbFGF (or additional cytokines). Cells were incubated and fed hESC media+100 ng/ml zbFGF (first week) or MEF-conditioned media+100 ng/ml zbFGF (thereafter) by half media exchange every other day. To avoid cell loss during feedings the plates were angled slightly for 10 minutes to allow the cells to settle and media was removed slowly from the media horizon.

iPSC Colony Identification and Picking—

Colonies with well-defined borders and typical hESC morphology began to appear around day 23. GFP and RFP silencing was verified by fluorescent microscopy and the number of colonies were counted to estimate reprogramming efficiency given the number of input plated cells. Colonies were manually harvested, transferred to MEFs, and expanded according to established protocols (Maherali and Hochedlinger, 2008; Thomson et al., 1998). Estimates of reprogramming efficiency were obtained by dividing total number of putative iPSC colonies by the input number of transduced cells. Counts were ceased after colony harvest (day 25-30) to avoid the inclusion of false positive re-seeded colonies left behind from the harvest.

DNA Fingerprinting—

TiPS cell lines and donor PBMCs were sent to the University of Wisconsin Histocompatibility/Molecular Diagnostics Laboratory (Madison, Wis.) for short tandem repeat (STR) analysis. Genotypes for 8 STR loci were determined from TiPS cell sample DNA.

Karyotyping—

G banding analysis was conducted by WiCell Research Institute (Madison, Wis.).

T-cell Receptor β Chain Rearrangement Analysis—

Genomic DNA was isolated per manufacturer's protocol (using the Qiagen DNeasy Blood and Tissue kit) from donor T-cells, the TiPS cell lines, and a fibroblast (non-T-cell) derived iPSC line used as a negative control. Additionally, DNA was isolated from frozen teratoma samples and parent cell lines by first dissolving tissue and cell samples in a buffer containing Tris, NaCl, EDTA, SDS and Proteinase K (Invitrogen). DNA was then precipitated with saturated NaCl and ethanol, and resuspended in water for PCR analysis. PCR was performed using a multiplex primer kit (Invivoscribe Technologies, San Diego, Calif.) specific for a majority of clonal TCR β chain rearrangements (van Dongen et al., 2003). Capillary electrophoresis and PCR product fragment analysis was performed at the University of Wisconsin Biotechnology Center DNA Sequencing Core Facility (Madison, Wis.) using an ABI 3730 DNA analyzer. Data was analyzed using Peak Scanner software (ABI, Foster City, Calif.).

Alkaline Phosphatase (AP) Staining—

Confluent cells grown on MEFs were AP stained with Vector Blue Alkaline Phosphatase Substrate Kit III (Vector Laboratories, SK-5300, Burlingame, Calif.) according to the manufacturer's protocol.

RT-PCR for Transgene and hESC Marker Gene Expression—

Total RNA was isolated using the RNeasy Mini Kit (Qiagen, Germantown, Md.) according to the manufacturer's protocol. First strand cDNA synthesis was carried out with oligo-dT primers (as described previously (Yu et al., 2009; Takahashi et al., 2007)) using SuperScript III First Strand Synthesis kit (Invitrogen) according to the product protocol. cDNA was diluted 1:2 and PCR reactions were performed with GoTaq Green Master Mix (Promega, Madison, Wis.) using a Mastercyler (Eppendorf, Hauppauge, N.Y.).

PCR Analysis of Viral Integration—

Genomic DNA was isolated from $1\text{-}5 \times 10^6$ iPSCs using DNeasy Blood and Tissue kit (Qiagen) according to the manufacturer's protocol for cultured cells. Genomic DNA (5 ul) was used for PCR reactions to check for viral integration using GoTaq Green Master Mix (Promega). Specific primer sets were used that detect only the transgene and not the endogenous gene. Primers for endogenous OCT4 served as a positive control for the reaction. Reactions were performed with primers as described previously (Yu et al., 2009; Takahashi et al., 2007).

Flow Cytometry: iPSC Line Intracellular and Surface Pluripotency Marker Characterization—

TiPS maintained on Matrigel were harvested and stained for the presence of Tra-1-81(BD Pharmingen or Stemgent, San Diego, Calif., both clone Tra-1-81), SSEA-3 (BD Pharmingen, clone MC631) and SSEA-4 (BD Pharmingen, clone MC813-70). Intracellular OCT4 (BD, clone 40/Oct-3) staining was performed on cells fixed with 2% paraformaldehyde and permeablized with PBS+0.1% saponin. Cells were stained overnight and analyzed the next day on an Accuri flow cytometer.

Hematopoietic Differentiation and Colony-Forming Unit Assays—

Undifferentiated TiPS were adapted to feeder-free conditions on Matrigel coated plates and maintained using mTeSR medium (Stem Cell Technologies, Vancouver BC, Canada). The colonies were harvested using TrypLE (Invitrogen) and placed in serum-free embryoid body (EB) basal media [containing IMDM, NEAA, Glutamine (Invitrogen) and 20% BIT-9500 (Stem Cell Technologies) and ROCK inhibitor H1152 in low-attachment plates to facilitate aggregate formation. Following aggregate formation, the cells were placed in EB basal media supplemented with growth factors and cytokines: rhBMP-4 (R&D Systems, Minneapolis, Minn.), rhVEGF, zbFGF, rhFlt-3 ligand, rhIL-3, and rhGM-CSF (Invitrogen) for 12 days. The cells were harvested and the phenotype generated by each iPSC clone was assessed by surface staining for CD31, CD34, CD43, CD45, CD41 and CD235a by flow cytometry. The individualized cells were placed in MethoCult (Stem Cell Techonologies) media for assaying colony-forming units per the manufacturer's instructions.

Assay for Teratoma Formation—

Characterized iPSCs cultured on MEFs were injected intramuscularly into the hind limb of SCID/beige mice (Harlan Laboratories, Madison, Wis.). Three mice were injected per cell line, each with one 6-well plate of cells. Matrigel (BD Biosciences) was added at ⅓ total volume to the cell suspension prior to injection. Tumors formed at 5 to 12 weeks and were processed for hematoxylin and eosin staining and histological analysis by the McArdle Laboratory for Cancer Research (University of WI-Madison). All animal work was conducted according to relevant national and international guidelines under the approval of the Cellular Dynamics International Animal Care and Use Committee.

Cardiac Differentiation—

Cardiogenesis was induced via a cell aggregate method. Briefly, TiPS cells grown on MEFs were harvested with Collagenase IV (Invitrogren) and cells grown on Matrigel were dissociated into single cell suspension using Sodium Citrate. The cell suspension was allowed to form aggregates in ultra-low attachment flasks in the presence of recombinant human hepatocyte growth factor (HGF) and/or zbFGF. Additionally, ROCK inhibitor H1152 was added to Matrigel-sourced cell suspensions. Beating aggregates were dissociated and stained for Cardiac Troponin T (cTnT) (Abcam, Cambridge, Mass., clone 1C11) on day 14 to 15.

Neuronal Differentiation—

The neural differentiation of TiPS cells was performed as previously described (Ebert et al., 2009). Briefly, TiPS grown on MEFs were partially dissociated with Collagenase IV and cultured in suspension as aggregates in Stemline Neural Stem Cell Expansion Medium (Sigma-Aldrich) supplemented with B27 supplement (Invitrogen), bFGF (100 ng/ml) and epidermal growth factor (100 ng/ml, Chemicon, Billerica, Mass.). Cultures were passaged weekly using a McIlwain tissue chopper. To induce neural differentiation, spheres were grown in neural induction medium (DMEM/F12 plus N2 supplement, Invitrogen) for one week and then plated onto poly-ornithine/laminin (Sigma-Aldrich)-coated coverslips in the same neural induction medium supplemented with cAMP (1 uM, Sigma-Aldrich), ascorbic acid (200 ng/ml, Sigma-Aldrich), brain-derived neurotrophic factor and glial cell line-derived neurotrophic factor (both 10 ng/ml, R&D Systems) for a further 3 weeks. The expression of neuronal maker beta III-tubulin was analyzed by immunofluorescence staining as previously described (Zhang et al., 2001).

Example 9

Figure 6A:
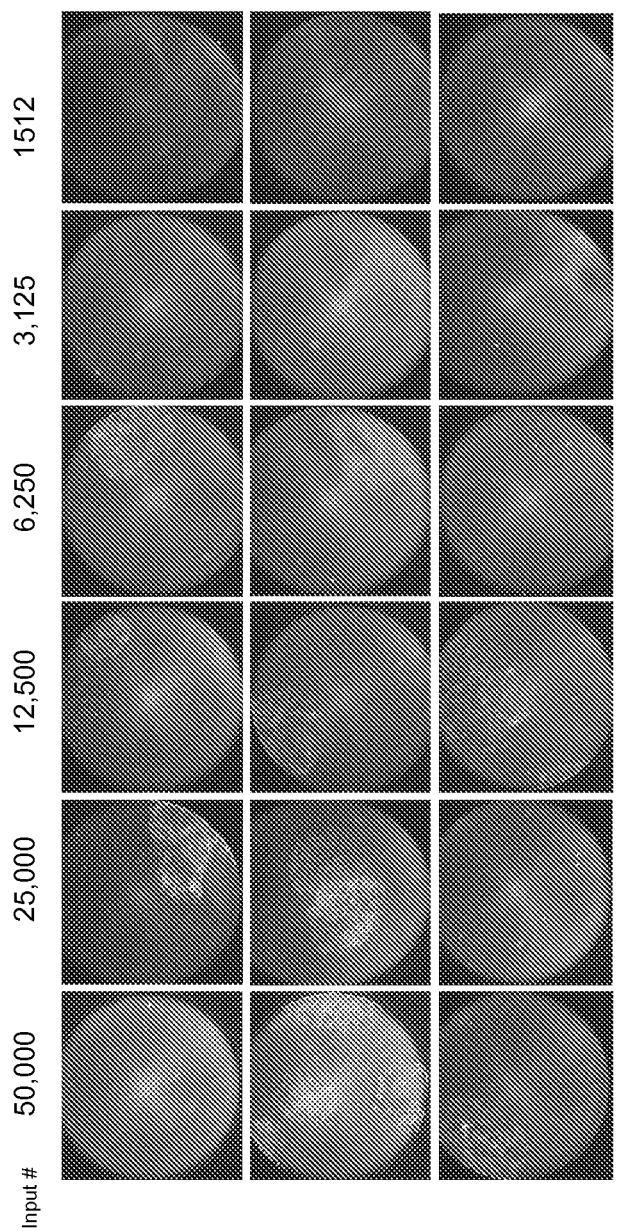
FIGS. 6A-6B. Reprogramming T cells in 96-cell format.
Figure 6B:
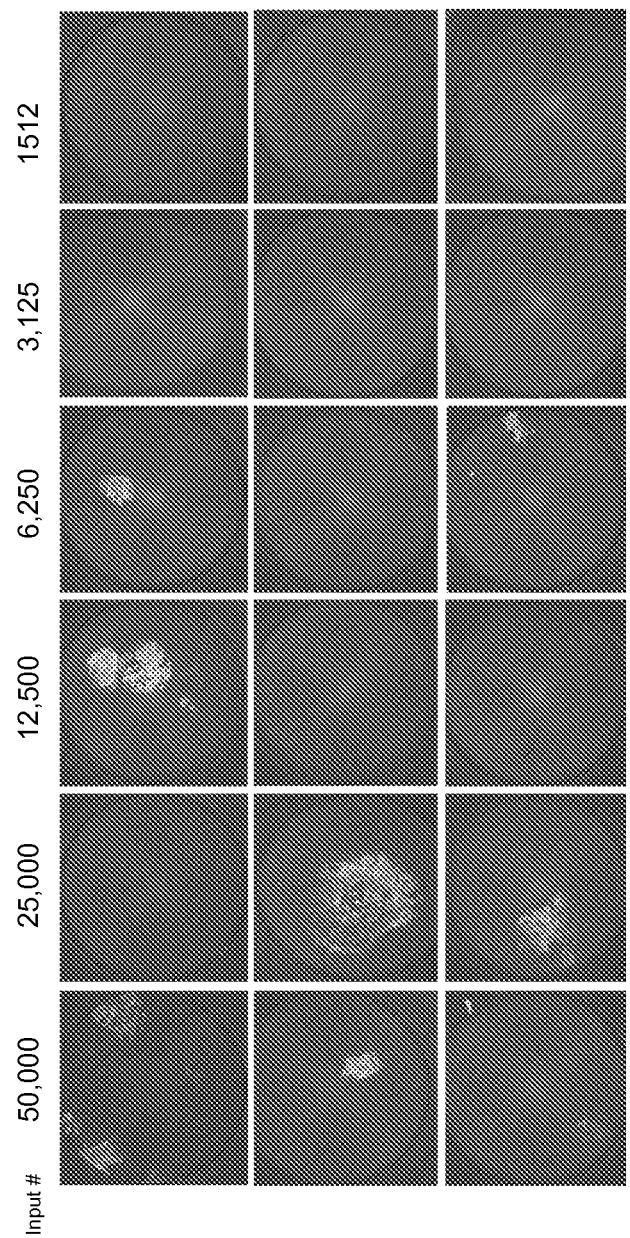

Retroviral Reprogramming of T-Cells from Cryopreserved Human Peripheral Blood Patient Samples This Examples presents the protocol used in the "10 donor" experiment. In that experiment, reprogramming was done as a trial on ten patient samples and each of the ten patient samples successfully reprogrammed. As shown in FIGS. 6A-6B, Tra-1-60 staining of IPS colonies on MEFs in a 96-well format with low number of input T cells. This demonstrates the efficiency of the T-cell approach.

This Example describes a set of procedures (Procedures 1-11 in detail below) for efficient retroviral reprogramming of human peripheral blood T-lymphocytes, particularly the multiple steps and the timing necessary to achieve Moloney murine leukemia virus (MMLV)-based reprogramming of human peripheral blood T-lymphocytes. The Example focuses on the use of cryopreserved cells and freshly prepared virus supernatants that comprise dual-gene MMLV vectors Oct4-Sox2 and c-Myc-Klf4, or Nanog-Lin28. The procedures in the Example may be adapted for use with other vector systems and may also be used for non-cryopreserved sample.

1. Preparatory Procedures:

Prior to ordering and/or receiving peripheral blood samples, establish and maintain an actively growing culture of adherent 293T cells and a separate culture of non-adherent Jurkat cells. 293T cells are propagated to meet the demand for virus production. Virus production requires the use of several vectors and helper plasmids described in "Prepare MMLV reprogramming virus vectors" below. It is necessary to prepare these DNA samples before proceeding to this step. Finally, it is also recommended that an excess supply of MEF-conditioned media is prepared prior to "Prepare MMLV reprogramming virus vectors."

2. Prepare and Cryopreserve Peripheral Blood Mononuclear Cells (PBMCs):

The following describes a procedure for isolating human peripheral blood mononuclear cells (PBMCs) from Vacutainers® CPT™ tubes of human peripheral blood and cryopreservation of PBMCs. The procedure is intended to facilitate derivation of iPS cells, Blood was drawn into a separate (SST) tube and the tube was sent to an appropriate service laboratory for infectious disease testing. The blood sample was collected in CPT Vacutainer© and sent to the inventors. Upon receipt of the samples, they were stored at 4° C. in the proper biocontainment device. The donor information was recorded in a database and an identifying letter or number was assigned to this donor. The receipt of infection disease testing data that demonstrates negativity was also documented as defined by a Safety Committee.

After receipt of blood samples, PBMCs were isolated from CPT Vacutainer© by Sorvall Legend RT centrifuge (using biocontainment adapters if available) at 600×g for 25 minutes at 4° C. and the pellet was resuspended in 10 ml of cold PBS (for cryopreservation) or RPMI+P/S (for live cell culture). Cells were counted by using a Cedex instrument. Alternatively, perform replicate counts using trypan blue and a hemacytometer. Count the samples and record the number of viable cells per ml, and also the percent viability. Centrifuge at 400×g for 15 minutes at 4° C. and aspirate the supernatant to eliminate residual clotting factors.

After isolation, PBMCs were prepared for crypreservation by resuspending the pellet in cold CryoStor10 at approx $10\times10^6$ cells/ml and transferring to pre-cooled cryovials. Typically the yield from one 8 ml CPT Vacutainer© is 15-20 million cells and is divided to two cryovials. Place the cryovials in a pre-cooled Mr.Frosty canister, then transfer the canister into a −80° C. freezer overnight. The following day, transfer the cryovials to a liquid nitrogen storage tank for long term storage.

Figure 11A:
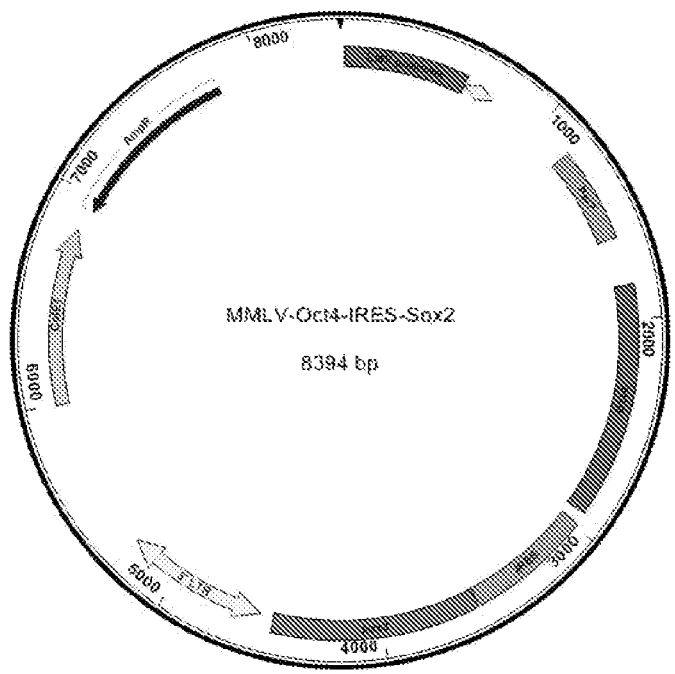
FIGS. 11A-11C. Vector maps of the bicistronic MMLV retroviral constructs used for reprogramming experiments with improved reprogramming.
Figure 11B:
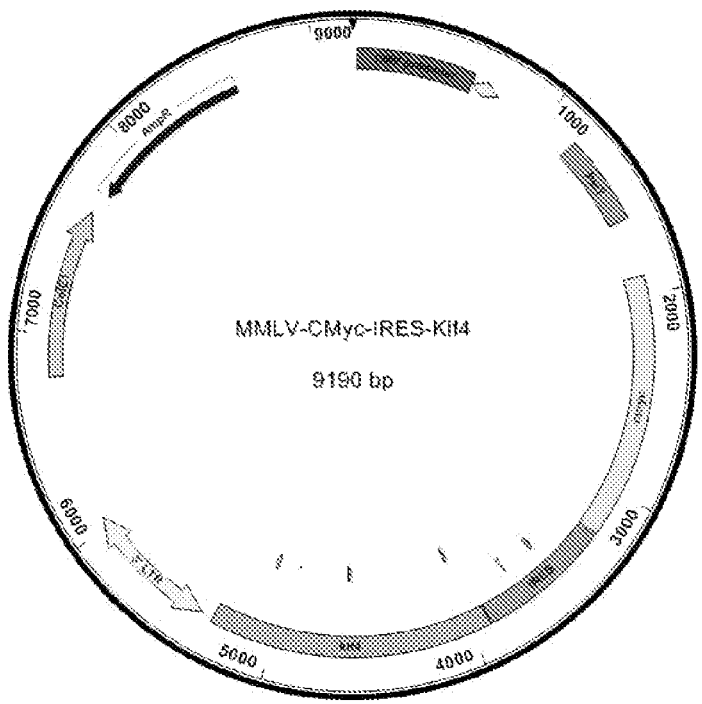
Figure 11C:
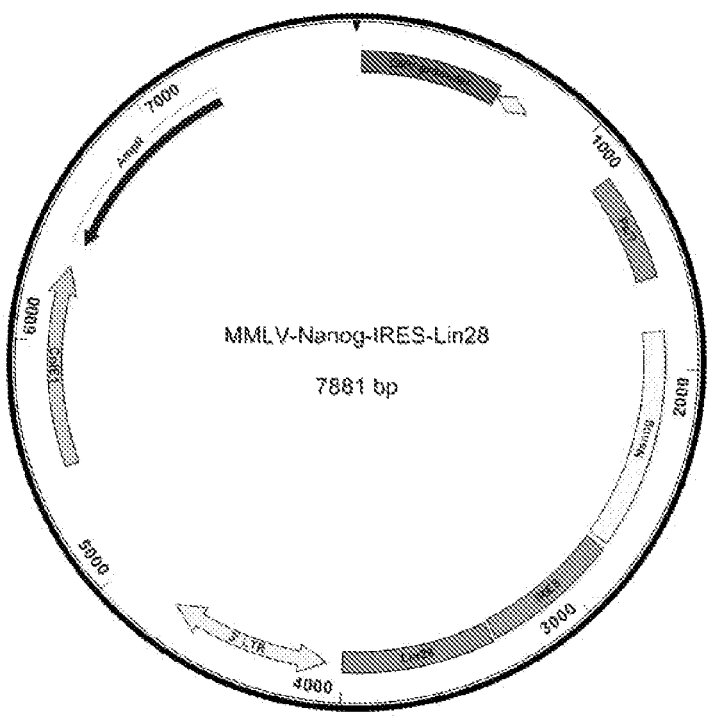

3. Prepare MMLV Reprogramming Virus Vectors:

To maintain optimal virus activity, it is recommended that the virus supernatant is stored at 4° C. for less than 4 days prior to use. This protocol describes the production of retrovirus-containing media by transient transfection of MMLV-based reprogramming bicistronic vectors Oct4-Sox2, cMyc-Klf4, and Nanog-Lin28 (vector maps are represented in FIGS. 11A-11C). It is intended to facilitate derivation of iPS cells by retroviral transduction of human T-cells in 96-well format using a combination of two or three of these vectors.

Propagate and Expand 293T Cells Over the Course of Several Days (or Weeks).

The extent of the scale up will depend upon the number of cells needed for the transient transfection method described below, and the corresponding volumes of virus containing supernatant generated. Formulas are provided below to calculate these values.

Preparation for Virus Production.

MMLV reprogramming vectors are designated Oct4-Sox2, cMyc-Klf4, or Nanog-Lin28 corresponding to the names of the vector plasmids (as represented in FIGS. 11A-11C), and referred to here as OS, CK, and NL, respectively. Reprogramming may be achieved through the use of OS+CK, OS+NL, or a combination of all three vectors (OS+CK+NL). An excess of each vector plasmid DNA, as well as the helper plasmids described below, must be prepared prior to initiating this protocol. It is also recommended that a control MMLV plasmid (Sox2-GFP) be prepared.

Determine the number of wells (n) containing target cells that will receive virus, and which combination of viruses each well will receive. For example, ten (10) different donor T-cell samples were seeded to 7 wells each in 96-well format and activated as described below; they occupy a total of 70 wells: Two wells from each donor will receive OS+CK reprogramming viruses ($n_{OS+CK}=20$); Two wells will receive OS+NL reprogramming viruses ($n_{OS+NL}=20$); Two wells will receive a control Sox2-GFP virus ($n_{GFP}=20$); The one remaining well will represent a non-transduced control.

Calculate the volume of supernatant media (V) from each vector required by use the following equation: $V=(n)\times(dose)\times F$; where dose=ml of virus applied to each well (typically 0.05 ml), and F represents the concentration factor (typically 50-fold) achieved after precipitation of the supernatant (in the step Concentrating the virus below). Following the example above, the total number of wells receiving the OS virus $n_{OS+CK}+n_{OS+NL}=40$. Assuming dose=0.05 ml, and F=50, calculate $V_{OS}=(n_{OS+CK}+n_{OS+NL})\times(dose)\times F=40\times(0.05)\times 50=100$ ml. Calculate $V_{CK}=(n_{OS+CK})\times(dose)\times F=20\times(0.05)\times 50=50$ ml. Calculate $V_{NL}=(n_{OS+NL})\times(dose)\times F=20\times(0.05)\times 50=50$ ml. Calculate $V_{GFP}=(n_{GFP})\times(dose)\times F=20\times(0.05)\times 50=50$ ml.

Calculate the number of plates (P) of 293T cells needed for each virus using the equation: $(P)\times(Y)=V$, where V is $V_{OS}$, $V_{CK}$, $V_{NL}$ or $V_{GFP}$ (from calculation above) and Y is the yield of supernatant for a given plate format. See Table below for Y-values. If the calculation for P is a non-integer, round up to the nearest integer. Prepare an excess number of 293T plates if necessary.

Solve the equation $P_{OS}=V_{OS}\div(Y)$ For the example above: $V_{OS}=100$ ml, choose the 15 cm format for larger yields per plate, thus Y=14.5. $P_{OS}=100\div14.5=6.8$ plates. Round up to $P_{OS}=7$ plates. $V_{CK}=V_{NL}=V_{GFP}=50$ ml, thus solving the equation for $P_{CK}$, $P_{NL}$, or $P_{GFP}$: $50\div14.5=3.4$ plates. Round up to 4 plates each. $P_{CK}=P_{NL}=P_{GFP}=4$ plates.

| 293T | Seeding density | Viral Supernatant Yield (Y) | Media |
|---|---|---|---|
| 10 cm plate | $5\times10^6$ | 4.5 ml | D10F |
| 15 cm plate | $13.5\times10^6$ | 14.5 ml | D10F |

Wash the 293T cells with PBS, and add enough trypsin to cover the monolayer. Incubate at room temperature for 10 minutes, then dislodge the cells by rapping the side of the dish. Collect the cells in a 50 ml tube(s). Wash each plate with a small volume of D10F. Collect and combine the wash media and cells. Mix thoroughly and transfer a 300 ul aliquot to a Cedex cup and count the cells. Alternatively use Trypan Blue and a hemacytometer. Centrifuge at 350×g for 10 minutes. Aspirate the supernatant and resuspend the pellet in fresh D10F. Calculate ($P_{OS}+P_{CK}+P_{NL}+P_{GFP}$), the total number of plates from the step of calculation of the number of plates (P) of 293T cells needed for each virus. Using the seeding densities in the table (below), seed the required number of 293T cells to each plate. Incubate in D10F for approximately 24 hours at 37° C./5% $CO_2$. Transfection efficiency and thus virus production is reduced if the cultures are over- or underconfluent. Visualize the cells under the microscope to ensure that confluency is optimal (approximately 90-95%).

Calculations are made to assess how much of each MMLV or control plasmid ($\mu g_{OS}$, $\mu g_{CK}$, $\mu g_{NL}$, or $\mu g_{GFP}$) is needed for transfection of each set of 293T cell plates. To simplify the calculations, it is recommended that the concentration of each plasmid DNA sample be adjusted to 1.0 or 2.0 mg/ml. Choose the appropriate value from the chart below (see column labeled "Vector"), and multiply by $P_{OS}$, $P_{CK}$, $P_{NL}$ or $P_{GFP}$. Then divide by the plasmid DNA concentration ($C_{OS}$, $C_{CK}$, $C_{NL}$, or $C_{GFP}$) to determine the required volumes ($\mu l_{OS}$, $\mu l_{CK}$, $\mu l_{NL}$, or $\mu l_{GFP}$).

|  | PEI (1 µg/µl) | Vector or control plasmid | 2843 (Gag/Pol) | 1238 (NFkB) | 2842 (VSVG) |
| --- | --- | --- | --- | --- | --- |
| 10 cm plate | 40 µl | 10 µg | 3 µg | 1 µg | 1 µg |
| 15 cm plate | 108 µl | 27 µg | 8.1 µg | 2.7 µg | 2.7 µg |

Optional: adjust each plasmid DNA concentration (C) to 1 µg/µl. Following the above example, and assuming C=1; $P_{OS}$=7, thus $\mu g_{OS}$=(27 µg)×7=189÷$C_{OS}$=189 $\mu l_{OS}$. Following the same example, $P_{CK}$=$P_{NL}$=$P_{GFP}$=4, thus $\mu g_{CK}$=(27 µg)×4=108÷$C_{CK}$=108 $\mu l_{CK}$, $\mu g_{NL}$=(27 µg)×4=108÷$C_{NL}$=108 $\mu l_{NL}$, $\mu g_{GFP}$=(27 µg)×4=108÷$C_{GFP}$=108 $\mu l_{GFP}$.

To determine the total amount of each helper plasmid ($\mu g_{GagPol}$, $\mu g_{NFkB}$, $\mu g_{VSV}$) or transfection reagent ($\mu l_{PEI}$) that is required for ALL plates, choose the appropriate value from the chart above (columns labeled Gag/Pol, NFkB, VSVG, or PEI) and multiply by the sum value ($P_{OS}$+$P_{CK}$+$P_{NL}$+$P_{GFP}$). Then divide by the plasmid DNA concentration ($C_{OS}$, $C_{CK}$, $C_{NL}$, or $C_{GFP}$) to determine the required volumes. Following the example, ($P_{OS}$+$P_{CK}$+$P_{NL}$+$P_{GFP}$)=7+4+4+4=19 and assuming C=1; then, $\mu g_{GagPol}$=(8.1 µg)×19=153.9÷$C_{GagPol}$=153.1 $\mu l_{GagPol}$, $\mu g_{NFkB}$=(2.7 µg)×19=51.3÷$C_{NFkB}$=51.3 $\mu l_{NFkB}$, $\mu g_{VSV}$=(2.7 µg)×19=51.3÷$C_{VSVG}$=51.3 $\mu l_{VSV}$, $\mu l_{PEI}$=108 µl×19=2.052 ml.

Transfection in 10 Cm Plate Format: Tube $1_{OS}$:

Aliuquot ($P_{OS}$×0.5) ml of OptiMEM, then add ($P_{OS}$×40) µl PEI drop-wise with mixing. Do not touch sides. Incubate 5 min at room temperature. Tube $2_{OS}$: Aliquot ($P_{OS}$×0.5) ml of OptiMEM to a second tube. Prepare a cocktail of the appropriate ratio (10:3:3:1) of plasmids. Choose the appropriate values ($\mu g_{OS}$, $\mu g_{GagPol}$, $\mu g_{NFkB}$, and $\mu g_{VSVG}$) from the chart above, and multiply by $P_{OS}$ to obtain the required plasmid amounts. Then divide by $C_{OS}$, $C_{GagPol}$, $C_{NFkB}$, or $C_{VSVG}$ to determine the required volumes ($\mu l_{OS}$, $\mu l_{GagPol}$, $\mu l_{NFkB}$, and $\mu l_{VSVG}$). Add these volumes to Tube $2_{OS}$: $\mu l_{OS}$+$\mu l_{GagPol}$+$\mu l_{NFkB}$+$\mu l_{VSVG}$ and mix. Repeat these steps by substituting the NL or CK or Sox2-GFP plasmid for the OS plasmid. Prepare a corresponding set of tubes: Tubes $1_{NL}$ and $2_{NL}$, or Tubes $1_{CK}$ and $2_{CK}$ or Tubes $1_{GFP}$ and $2_{GFP}$. Substitute the appropriate P and C values to calculate the appropriate volumes for the Tube 2 cocktail. To make DNA/PEI mixture, combine each Tube #1 with the corresponding Tube #2, mix, and incubate at RT for 20 min. Wash each plate of 293Ts twice with 5 ml PBS. Add 4 ml OptiMEM to each plate. Add 1 ml of the plasmid DNA/PEI mixture dropwise directly to each plate. Incubate 4-6 hours at 37° C./5% $CO_2$. Aspirate the media, then wash each plate with 5 ml PBS. Add 5 ml of D10F+50 mM HEPES media to each plate. Incubate at 37° C./5% $CO_2$ overnight. Transfer the Sox2-GFP-infected (control) cells to the fluorescent microscope. The fluorescence should be detectable. Incubate at 37° C./5% $CO_2$ for an additional 24 hours.

Transfection in 15 cm Plate format: Tube $1_{OS}$:

Aliquot ($P_{OS}$×1.0) ml of OptiMEM, then add ($P_{OS}$×108) µl PEI drop-wise with mixing. Do not touch sides. Incubate 5 min at room temperature. Following the example, $P_{OS}$=7: Aliquot 7 ml of OptiMEM to Tube $1_{OS}$ and add 1.96 ml PEI. Tube $2_{OS}$: Aliquot ($P_{OS}$×1.0) ml of OptiMEM to a second tube. Following the example, $P_{OS}$=7: Aliquot 7 ml of OptiMEM to Tube $2_{OS}$. Prepare a cocktail of the appropriate ratio (10:3:3:1) of plasmids. Choose the appropriate values ($\mu g_{OS}$, $\mu g_{GagPol}$, $\mu g_{NFkB}$, and $\mu g_{VSVG}$) from the chart above, and multiply by $P_{OS}$ to obtain the required plasmid amounts. Then divide by $C_{OS}$, $C_{GagPol}$, $C_{NFkB}$, or $C_{VSVG}$ to determine the required volumes ($\mu l_{OS}$, $\mu l_{GagPol}$, $\mu l_{NFkB}$, and $\mu l_{VSVG}$). Add these volumes to Tube $2_{OS}$: $\mu l_{OS}$+$\mu l_{GagPol}$+$\mu l_{NFkB}$+$\mu l_{VSVG}$ and mix.

Following the example, $P_{OS}$=7 and assuming C=1 for all plasmids: $\mu g_{OS}$=27 µg×7 plates=108÷$C_{OS}$=108 $\mu l_{OS}$, $\mu g_{GagPol}$=8.1×7=56.7÷$C_{GagPol}$=56.7 $\mu l_{GagPol}$, $\mu g_{NFkB}$=2.7×7=18.9÷$C_{NFkB}$=18.9 $\mu l_{NFkB}$, $\mu g_{VSVG}$=2.7×7=18.9÷$C_{NFkB}$=18.9 $\mu l_{VSVG}$. Add these volumes to Tube $2_{OS}$ and mix. Repeat Steps these steps by substituting the NL or CK or Sox2-GFP plasmid for the OS plasmid. Prepare a corresponding set of tubes: Tubes $1_{NL}$ and $2_{NL}$, or Tubes $1_{CK}$ and $2_{CK}$ or Tubes $1_{GFP}$ and $2_{GFP}$. Substitute the appropriate P and C values to calculate the appropriate volumes for the Tube 2 cocktail. To make DNA/PEI mixture, combine each Tube #1 with the corresponding Tube #2, mix, and incubate at room temperature (RT) for 20 min. Wash each plate twice with 10 ml PBS. Add 13 ml OptiMEM to each plate. Add 2 ml of the plasmid DNA/PEI mixture dropwise directly to each plate. Incubate 4-6 hours at 37° C./5% $CO_2$. Aspirate the media, then wash each plate with 15 ml PBS. Add 15 ml of D10F+50 mM HEPES media to each plate. Incubate 37° C./5% overnight. Transfer the Sox2-GFP-infected (control) cells to the fluorescent microscope. The fluorescence should be detectable. Incubate at 37° C. for an additional 24 hours.

Harvesting the Virus supernatant.

Transfer the Sox2-GFP-transduced cells to the fluorescent microscope again. The majority of cells should be emitting green fluorescence and the fluorescence should be uniform across the plate. Virus producing cells should also exhibit a noticeable change in cell morphology. Pool the virus containing supernatant media from each set of transfected cells. (Caution: supernatants contain infectious virus) Filter the virus supernatant through a 0.45 um or 0.8 um filter to remove cells and debris. (Note: use cellulose acetate or PES low protein binding filters. Do not use nitrocellulose filters.) MMLV has a limited shelf-life; store the viral supernatants at 4° C. for no more than 4 days. Optional: the supernatants may be stored at −80° C., however the freeze thaw cycle will cause a loss of functional activity. Proceed immediately to assess the virus titer using at least one of the following metrics: a) functional activity on proliferating Jurkat cells or T-cells and/or b) quantitation of viral RNA present per ml of supernatant. Quality control assay of MMLV vectors are described below.

To achieve high transduction efficiency of T-cells in 96-well format, it is important to concentrate the virus. However, the concentrated virus is also unstable. Furthermore the window of time in which the T-cell cultures are most highly proliferative (and thus most easily infected) is narrow. It is thus important to coordinate the preparation of the target cells and the concentration step. When QC assay(s) have been satisfied, proceed to activate the target PBMC's T-cells, and concentrate the virus supernatants for reprogramming 4. Perform Quality Control Assays for Virus Activity:

This protocol describes methods to assess transduction efficiency by transduction of cells with the following MMLV vectors: Oct4-Sox2 and c-Myc-Klf4, or Oct4-Sox2 and Nanog-Lin28, or a control Sox2-GFP vector. These assays are intended to be used to facilitate derivation of iPS cells.

Quality control assay for virus activity: Note: because of the relative instability of the virus it is important to be prepared to initiate one (or all) of the QC assays below on the day that the viral supernatant are collected. Virus may be stored at −70° C., however the freeze thaw cycle and/or storage of >3 weeks causes a loss of activity. After obtaining an acceptable QC assay result the PBMCs should be re-animated.

Perform quantitative real time RT-PCR using aliquots of each viral supernatant, according to manufacturer's protocol (Clontech). Alternatively, (or additionally), collect proliferating Jurkat cells and count using the Cedex. Resuspend the cells at $1 \times 10^6$/ml in R10F containing 4 ug/ml polybrene. Seed 100 ul of cells per well to a 96-well plate. Add 50 ul of virus to three wells and titrate the virus by serial dilution across several rows of the plate. Incubate 48 hours, then collect cells for FACS analysis. See procedure for intracellular immunolabeling of Oct4 and flow cytometry. Alternatively (or additionally) collect infected Jurkat cells for semi-quantitative PCR analysis. If the virus prep passes QC, proceed to the next step for transduction of T-cells.

5. Re-Animate Donor PBMCs and Activate T-Cells:

Efficient reprogramming of human T-cells can be achieved with MMLV vectors only if the production and delivery of the virus supernatants are carefully coordinated with the activation of the target cells. Here is disclosed successful activation as a cytokine-induced burst in the proliferation of $CD3^+$ cells from a mixed population of PBMCs yielding the formation of macroscopic "blast" colonies between 48 and 72 hours in culture. To utilize this activation protocol with MMLV-based reprogramming vectors, it is important to note that MMLV supernatants are unstable. Thus the virus should be prepared on a tightly controlled schedule so that fresh virus may be applied to the T-cell culture one day before blast colony formation. This protocol describes the re-animation of cells cryopreserved as described above, and the induction of blast colonies. Alternative sources of PBMCs may be utilized.

Prepare Media and Cytokines.

Prior to the addition of virus, the cells must be activated for 48 hours. Thus this step is designated as Day −2. Reprogramming begins on Day 0. Add a working concentration of Pen/Strep/glutamine to AIM-V media. Store at 4° C. for no more than two weeks. It is recommended that small volume aliquots of IL2 are prepared and stored at −20° C. Thaw one aliquot for use here. After thawing one aliquot, store it at 4° C. for no more than two weeks. OKT3 (1 mg/ml anti-CD3) should be stored at 4° C. Dilute 1 µl in 1 ml of AIMV media to a 1 µg/ml intermediate dilution.

Re-Animation of Donor PBMCs and Activation of T-Cells.

The day that the PBMCs are thawed is referred to as Day −2. Remove the PBMCs from storage and thaw rapidly in a 37° C. water bath. Dilute the cells (and freezing media) with an equal volume of warm RPMI media. Mix gently and transfer to a 15 ml tube. Slowly dilute with RPMI to a total volume of 10 ml. Mix thoroughly, remove a 300 µl aliquot, and count the cells using a Cedex algorithm with a size threshold of 1 micron. Alternatively, stain cells with Trypan Blue and count with a hemacytometer. Note: it is not unusual to lose 50% of the cells that were present in the primary PBMC sample (prior to cryopreservation). However, the remaining cells should be >90% viable. Centrifuge the cells at 350×g for 10 min, aspirate the supernatant and resuspend in warm AIM-V+Pen/Strep/glutamine at a density of $2 \times 10^6$ viable cells/ml. Add 300 IU/ml IL2 and 10 ng/ml OKT3 antibody. Mix the cells, and dispense 100 µl per well in a flat bottom 96-well tissue culture plate, incubate at 37° C., 5% $CO_2$. Avoid using the perimeter wells if possible, as evaporation is more noticeable in these wells. Forty eight hours later (Day 0), observe the cells by bright field microscopy using a 20× objective (or higher magnification). Note: evidence of cell division and clusters of cells (nascent blast colony formation) should be detectable.

6. Concentrate the Virus Supernatants:

This protocol describes two separate methods for increasing the titer of MMLV vectors by concentrating retroviral supernatants collected from 293T cells following transfection with a combination of reprogramming vectors (Oct4-Sox2 with cMyc-Klf4 or Nanog-Lin28; representative vector maps are shown in FIGS. 11A-11C). It is intended to facilitate derivation of iPS cells by retroviral transduction of T-cells. It is recommended that the titer of the virus supernatant be assayed according to Quality control assay of MMLV vectors as described above).

For large volumes of virus, the LentiX method is recommended. This method requires an overnight incubation, thus it should be initiated on Day −1. Alternatively, for virus prep's of 30 ml or less, the Amicon method may be used on Day 0.

Un-concentrated MMLV supernatants (prepared according to procedures described above) may be stored at 4° C. for 4 days without significant loss of activity. After concentrating the supernatant using either method (below), the virus should be kept cold (on ice) and used as soon as possible. If the target cells are NOT ready to be infected upon completion of this procedure, store the concentrated virus at −80° C.

Concentrating the Virus (on Day −1) by the LentiX method. Note: this method is recommended for large scale virus concentration, (supernatant volumes >30 ml). Transfer the supernatants into 50 ml tubes and add the Lenti-X concentrator according to the manufacturers recommendations. Combine 3 volumes of clarified viral supernatant with 1 volume of Lenti-X Concentrator. Mix by gentle inversion. Incubate overnight at 4° C. 18-24 hours later, on Day 0, centrifuge the samples at 1,500×g for 45 minutes at 4° C. After centrifugation, an off-white pellet will be visible. Carefully remove supernatant, taking care not to disturb the pellet. Residual supernatant can be removed with either a pipette tip or by brief centrifugation at 1,500×g. Gently resuspend the pellet in ⅕₀th of the original volume using cold D10F. The pellet may be somewhat sticky at first, but it should go into suspension quickly. Proceed immediately to apply the virus to the target cells.

Concentrating the Virus by Amicon Filtration Method (on Day 0). Use this method to concentrate virus supernatant prep's of 30 ml or less. Wash an AmiconY100,000 MW cassette by adding 10 ml of PBS and centrifuging the device at 1000×g for 3 minutes or until all the PBS has passed through the filter. Apply 15 ml of supernatant virus to the Amicon cassette and spin at 2000×g for 20 minutes. Typically this will result in an approximate 10-fold concentration (by volume). Spin the sample for an additional 5-10 minutes to concentrate the virus more. This process may be repeated to reduce the volume by as much as 50-fold (final volume approximately 300 µl). Repeat this process (in parallel) with each viral vector supernatant. Recommendation: Do not attempt to process more than four (4) Amicon cassettes at one time. During long delays the supernatant will passively drip through the cassette and result in an uneven distribution of weight across the opposing rotor arms. This may cause the centrifuge to be unbalanced. Collect the retentates. Proceed immediately to apply the virus to the target cells.

7. Transduce the Activated T-Cells (on Day 0):

This procedure is for transduction of human peripheral blood T-lymphocytes with concentrated MMLV-based reprogramming vectors. This protocol describes transduction of T-cells in a 96-well plate with the MMLV-based reprogramming vectors Oct4-Sox2, c-Myc-Klf4, or Nanog-Lin28, or Sox2-GFP, or combinations thereof. A quality control assay described above is recommended to assess viral activity prior to using this protocol.

The day of transduction represents the initiation of the reprogramming process (designated as Day 0). This time point occurred 48 hours after PBMCs were thawed and activated in 96-well format (as described in Procedure 5. Re-animate donor PBMCs and activate T-cells). Concentrated MMLV vectors should be prepared in advance according to Procedures 3, 4, and 6).

Observe the cells under phase microscopy. There should be evidence of nascent blast colony formation.

Optional: Collect cells and count. Typically, the number of PBMCs drops significantly within 24 hours of activation, (day −2 to day −1) to approximately 25-50,000 cells per well. Between 24 and 48 hours (day −1 to day 0), the cell number is typically unchanged. Between Day 0 and Day 1, the ATP content increases and nascent blast colony formation appears. The cell number on Day 0 is typically between 1 and $2 \times 10^5$ per well. Between Days 0 and 1, blast colonies should be apparent and cell numbers increase significantly.

Optional: collect cells for FACS analysis to characterize T-cells. Previous trials across multiple PBMC donors show >90% of cells display anti-CD3 surface labeling on Day 0. The distribution of CD4+ and CD8+ cells varies. Typically, there are twice as many CD4+ cells compared to CD8+ cells.

Combine equal volumes of each concentrated virus and add 8 μg/ml polybrene and 300 units/ml IL-2. Prepare enough of this mixture for the given number of wells to be infected.

Following the procedure described in Procedure 3: ten (10) different donor T-cell samples were seeded to 7 wells, each in 96-well format and activated; they occupy a total of 70 wells. Two wells from each donor will receive OS+CK reprogramming viruses ($n_{OS+CK}$=20). Two wells will receive OS+NL reprogramming viruses ($n_{OS+NL}$=20). Two wells will receive a control Sox2-GFP virus ($n_{GFP}$=20). The one remaining well will represent a non-transduced control. Combine (50 μl$_{OS}$+ 50 μl$_{CK}$)×$n_{OS+CK}$=2 ml; add 2 μl of polybrene and 1.2 μl of IL-2.

Combine (50 μl$_{OS}$+50 μl$_{NL}$)×$n_{OS+NL}$=2 ml; add 2 μl of polybrene and 1.2 μl IL-2. Combine (50 μl$_{GFP}$+50 D10F)× $n_{GFP}$=2 ml; add 2 μl of polybrene and 1.2 μl of IL-2. Combine 2 ml D10F, 2 μl of polybrene and 1.2 μl of IL-2 for mock-infections.

To undisturbed wells, add 100 μl of the virus cocktail to each well. Mix the cells gently with the pipettor. Perform a mock-infection by adding 100 μl of D10F+300 IU/ml IL2+8 μg/ml polybrene. Mix the cells gently with the pipettor. Centrifuge the 96-well plate for 90 minutes at 1000×g at 32° C. using the appropriate biocontainment adapters. Transfer the plate to the incubator at 37° C./5% CO$_2$ overnight.

Plate Irradiated MEFs (DAY 0, or DAY 1) in preparation for reprogramming by MEF-co-culture (according to Procedure 8).

On DAY 1—24 hours after the initial exposure to virus, inspect the cell morphology. Blast colonies should be plainly visible under the microscope. Optional: Collect cells, centrifuge, resuspend in (virus-free) D10F media and count on the Cedex. Alternatively use Trypan Blue and a hemacytometer.

Carefully remove 100 μl of media from each well without disturbing the cells. For multiple wells, use a multi-channel pipettor, being careful not to lower the tips too close to the bottom of each well. Discard this media in a beaker or tray containing 10% bleach. Replace the media with 100 ul of fresh D10F+HEPES+IL2 (300 u/ml). The following day, repeat the media removal steps (Day2).

Verify expansion of T-cells and assess transduction efficiency (DAY 2) according to Procedure 9 described below.

8. Plate Irradiated MEFs (on Day 0 or Day 1):

This section describes a method for plating mouse embryonic fibroblasts (MEFs) on gelatin coated wells, which is intended to facilitate derivation of iPS cells.

Plate Irradiated MEFs for the production of conditioned media (CM). Order MEFs 2-3 days before intended use. Following the example in Procedure 3 for T-cell reprogramming, calculate the amount of MEF-CM necessary to maintain reprogramming co-cultures for approximately 20 "feedings" in 6-well format. Each feeding requires removal and replacement of 1.25 ml per well.

10 donor samples (transduced T-cells)×two experimental conditions (SO+CK vs. SO+NL)×three wells per condition=60 wells was used. SO refers to a bicistronic vector having Sox2 and Oct4, CK refers to bicistronic vector having cMyc and Klf4, and NL refers to Nanog and Lin28, all without any fluorescent marker (vector maps are represented in FIGS. 11A-11C). Calculate the volume of MEF-CM needed. (60×20×1.25 ml=1.5 liters).

Calculate the number of T75 flask-MEF cultures required to generate a sufficient volume of MEF-CM. (Note: repeated collections from one flask will generate approximately 120 ml of MEF-CM.). Following the example above, to generate 1.5 liters of MEF-CM: 1500 ml÷120 ml/flask=12.5 flasks. Round up to 13 flasks.

Add 12 ml of sterile 0.1% gelatin per T75 flask. Incubate for at least 1 hour in the incubator (37° C./5% CO$_2$). Aspirate gelatin and add 20 ml of high density irradiated MEFs (~2.1× $10^5$ cells/ml). Incubate overnight (37° C./5% CO$_2$). Visualize cells to ensure that MEFs have become attached. 24 hours after plating, aspirate the media and replace with 20 ml of hES media per flask. 24 hours later, collect ~20 ml of MEF-CM from each flask. Repeat steps 6.8 and 6.9 for five additional days. Freeze MEF-CM at −20° C. (Add 4 ng/ml zbFGF and filter only before using for IPS culture then filter.

Plate Irradiated MEFs (DAY 0, or DAY 1) for reprogramming co-cultures. Order MEFs 2-3 days before intended use. MEFs should be plated 1 or 2 days prior to adding the transduced cells for reprogramming co-cultures. Following the example in Procedure 3 for T-cell reprogramming, calculate the number of wells of MEFs necessary to receive 10 donor samples×3 wells per donor×3 experimental conditions (SO+ CK versus SO+NL versus GFP controls)=90 wells. Calculate the number of 6-well plates needed. (90÷6=15 plates). Add 2 ml of sterile 0.1% gelatin per well (6-well format). Optional: Coat 96-well plates with 100 μl gelatin per well. Incubate for at least 1 hour in the incubator (37° C./5% CO$_2$). Aspirate gelatin and add 2.5 ml of irradiated MEF cell suspension onto each well (6-well format). Optional: For 96-well format, aspirate gelatin and add 200 μl of MEFs cell suspension onto each well. Incubate overnight (37° C./5% CO$_2$). Visualize cells to ensure that MEFs have become attached.

9. Perform Quality Control Assays to Assess Transduction Efficiency (on Day 2):

This procedure describes quality control assays to assess MMLV transduction of human peripheral blood T-cells. The assays are intended to detect the presence of transgenes or reprogramming factors present in targeted T-cell populations 48 hours after the cells are exposed to concentrated MMLV vectors comprising combinations of Oct4-Sox2, c-Myc-Klf4, Oct4-Sox2 and Nanog-Lin28.

Activate human T-cells according to procedures described above. 48 hours later, infect the activated T-cells according to Procedure 7. Count the cells using the Cedex, or a hemacytometer.

Following the example in procedure 3 (and continued in procedure 7), remove 100 µl of supernatant media from each well without disturbing the activated cells. All wells should have approximately 100 µl remaining Mix and collect the remaining 100 µl of cells from one of the two Sox2-GFP-infected wells and transfer the cells directly into a Cedex cup. Wash each well with 200 µl of PBS; collect and combine the wash into the Cedex cup. Adjust the final volume to 300 µl if necessary. Repeat mix and wash steps for each of the 10 donor T-cell samples.

Count the cells on the Cedex using the T-cell algorithm (size threshold=1 micron). Record the cell density (Note: there should be $2\text{-}4\times10^5$ per well). Alternatively, thoroughly mix the cells from one well and remove 10 µl and mix with 10 µl of trypan blue, then count cells on a hemacytometer. (Note: this counting method is less accurate than the Cedex; however, it uses less cells.)

Assess the Transduction Efficiency of the Transduced T-Cells.

Optional: use the fluorescent microscope to visualize the cells that were transduced with the Sox2-GFP virus. With a multi-channel pipetor, mix and collect the remaining 100 µl of cells from one well of Sox2-GFP-infected T-cells from each donor sample (10 wells). Transfer the cells into a corresponding set of wells in a 96-well V-bottom collection plate. Mix and collect the remaining 100 µl of cells from the control (non-infected) wells from each donor sample (10 wells). Wash each well with 75 µl of PBS; collect and combine the wash into the corresponding wells of the collection plate. Centrifuge the collection plate for 10 minutes at 350×g. With a multi-channel pipetor, carefully remove the supernatants without disturbing the pellet in each well. Discard the supernatants in a beaker or tray containing 10% bleach. Resuspend and wash the pellets with 150 µl FACS buffer per well. Centrifuge the collection plate for 10 minutes at 350×g. Carefully remove the supernatants without disturbing the pellet in each well. Resuspend the pellets in FACS buffer containing 2-5 µg/ml anti-CD3-APC. Incubate at room temperature in the dark for 45 minutes.

Centrifuge the collection plate for 10 minutes at 350×g. Carefully remove the supernatants without disturbing the pellet in each well. Resuspend and wash the pellets with 150 µl FACS buffer per well. Repeat centrifuge steps.

Resuspend and wash the pellets with 100 µl FACS buffer containing 1 µg/ml propidium iodide per well. Analyze the cells with the Accuri. Assess transduction efficiency by estimating the percentage of live cells that express $GFP^+$. Assess the percentage of $GFP^+$ cells that are CD3+ by gating on the $GFP^+$ population.

10. Co-Culture Transduced T-Cells and MEFs (Days 3-30):

This procedure describes a procedure for co-culturing human T-cells transduced with reprogramming factors on mouse embryonic fibroblasts (MEFs). The protocol describes the co-culture of transduced T-cells on adherent MEFs and methods for re-feeding these cells.

1. Prepare MEF-conditioned media according to Procedure 8. Prepare this reagent before proceeding to Step 4 below.

2. Plate Irradiated MEFs for Reprogramming (according to Procedure 8). Receive and plate 2.5 ml of MEFs per well (in 6 well format) or 200 µl per well (in 96 well format). 24-72 hours later, replace the media with 2 ml of hES:D10F media (for 6 well format) or 100 µl per well (for 96 well format).

3. Perform quality control assays to assess the transduction efficiency (see Document #100405.RDL.09) two days after T-cells have been exposed to retrovirus. For T-cell reprogramming, this time point is designated as Day 2. If the transduction efficiency is adequate, proceed to Step 4.

4. Collect transduced T-cells (according to Procedure 7) and confirm that activation and transduction were successful according to Procedure.

For 6-well MEF plates: transfer 0.5-4×105 cells (in a volume of 25-100 ul) per well. Add dropwise across the entire surface. Optional: titrate the input cell number across 3 wells on the MEF plate. For 96-well MEF plates: transfer $1\text{-}8\times10^4$ cells (in a volume of 10-25 ul) per well. (Note: avoid using the perimeter wells if possible.) Optional: titrate the input cell# across multiple wells on the MEF plate.

The example below follows that described in Doc#100405_RDL_03; there are 10 sets of activated T-cell cultures derived from 10 blood donor samples. Each donor sample was arrayed across seven (7) wells of a 96-well plate and T-cells were activated. Two wells (2) were infected with SO+CK MMLV vectors; two wells (2) were infected with SO+NL MMLV vectors.

From each donor, collect the SO+CK infected T-cells and combine the cells in a FACS tube or 15 ml conical tube. From each donor, collect SO+NL infected T-cells and combine them in separate tubes. Optional: to precisely account for the seeding density (i.e. how many T-cells are delivered to the MEF plates), mix cells, remove 10 µl aliquots, combine with 10 µl Trypan blue and count cells with a hemacytometer. Centrifuge the samples at 350×g for 10 minutes using the appropriate biocontainment devices and centrifuge adapters. Carefully remove the supernatant and discard this media in a beaker or tray containing 10% bleach. Resuspend the cells with 400 µl of hES:D10F (approximately $4\text{-}8\times10^5$ cells total). Mix and transfer 200 µl of cells ($2\text{-}4\times10^5$ cells) dropwise to one well on a MEF plate (6-well format).

Dilute the remaining cells 2-fold with hES:D10F media, then transfer 200 µl of cells ($1\text{-}2\times10^5$ cells) dropwise to a second well on the same MEF plate. Dilute the remaining cells 2-fold with hES:D10F media, then transfer 200 µl of cells (approximately $0.5\text{-}1\times10^5$ cells) dropwise to a third well on the same MEF plate. Incubate overnight at 37°/5% $CO_2$.

5. Maintenance: Feeding Schedule (Day 4-Day 30). Two days later (on day 4), replace 50% of the media from each well with hES media+100 ng/ml of zebrafish FGF (growth media) using the following method: Remove the 6-well plates from the incubator. Stand one side of the plate on a discarded/unused 10 cm-culture dish lid, allowing the culture media to flow to one side of the well. (Note: at this angle, the media should still be covering the entire monolayer of MEFs and not spilling out of the well). Let the cells settle for 10 minutes. Remove each lid from the MEF plate, and carefully/slowly aspirate 50% of the media from the surface of the culture. Be careful not to aspirate cells. Keep the lid(s) for all subsequent feedings. Optional: Collect the aspirate, centrifuge 350×g for 4 minutes, resuspend in 1 ml media and count on Cedex. Verify that you are losing less than 1% of the cells. Add 1.25 ml of fresh growth media dropwise in a circular motion trying not to disturb the cells. Return the plate to the incubator. To replace the media in a 96-well plate co-culture, use a multi-channel pipettor and insert the tips approximately halfway to the bottom of the wells. Slowly aspirate 100 ul from the surface of the culture. Be careful not to aspirate cells. (Note: compared to the 6-well co-culture format, the T-cells will appear more stationary since the media is not easily agitated in this format.) Add 100 ul of fresh media (hES media+100 ng/ml of zFGF) dropwise trying not to disturb cells. Return the plate to the incubator.

On Day 6, repeat the feeding method on Day 4 described above. On Day 8, re-feed the cells (as above) with growth media+20% MEF-conditioned media. Repeat the feeding step on Day 8 every 48 hours. Visually inspect the wells during this time period to monitor colony formation.

11. Identify and Pick Colonies Expressing Tra1-60:

The procedure describes a guidelines for identifying and picking Tra1-60$^+$ colonies grown on MEF co-cultures under reprogramming conditions. Under the appropriate conditions, colonies of iPS cells will arise following the introduction of reprogramming factors into primary human cells. This protocol utilizes an antibody to Tra1-60 to fluorescently label putative iPSC colonies that arise in MEF co-cultures. By comparing the fluorescent labeling pattern and the morphology of the colonies, colonies are assigned a score which is a qualitative measure of pluripotency. This scoring system facilitates selective expansion of putative iPS cells for further characterization.

Following transduction with reprogramming factors, human cells are co-cultured on MEFs for 15-30 days. During this period of time, the cells should be visually inspected for colony formation. When colonies are visible, but not overgrown, count or estimate the total number of colonies present.

If the reprogramming vector(s) do NOT include a fluorescent reporter, go the following step: one or two days before picking colonies, seed irradiated MEFs on to a set of gelatin-coated 6 well plates or 96-well plates (according to Procedure 8) or 10 cm dishes.

If the reprogramming vector(s) include a fluorescent reporter, nascent colonies should be monitored under the fluorescent microscope. Make note of fluorescent and non-fluorescent colonies. Reprogramming events typically silence fluorescent reporters. However, in some cases, the cells may remain fluorescent. For this reason it is important to avoid using a fluorescent antibody (below) with fluorescent spectra that overlaps with that of the reporter.

Carry out the anti-Tra1-60 live cell labeling protocol, as follows: Wash wells to be stained with DMEM/F12 (serum-free) media two times. Dilute primary antibody in growth medium (hES) to the working dilution. Filter the diluted antibody using a 0.22 um sterile filter. Add diluted primary antibody to the cells. Add a sufficient volume to cover the monolayer. Incubate at 37° C. and 5% $CO_2$ for 45 min-1 hr. Wash the cells with DMEM/F12 media two times. Note: If you use a fluorescently labeled primary antibody, replace media with fresh hES and image the cells. Otherwise: Dilute the secondary antibody in growth medium (hES). Filter the diluted secondary antibody using a 0.22 um sterile filter. Add diluted antibody to the cells. Incubate at 37° C. and 5% $CO_2$ for 30 min. Wash cells once with DMEM/F12 and replace the media fresh hES+CM and use the fluorescent microscope to take images.

If there are numerous colonies, assign scores after acquiring and observing digital images. For only a few colonies, score each colony while the samples are under the microscope. Assign a "morphology" score using bright field microscopy, according to the descriptions below: 1=the colony would be described as partially reprogrammed; the colony has a diffuse border, and/or differentiated cells at the border; and/or differentiated cells that are fibroblast-like with discernable cytoplasm and nuclei. 2=the colony is distinct enough to be picked manually; this may comprise a colony of non-differentiated cells (with low cytoplasmic: nuclei ratio) with a semi-contiguous tight border interrupted by differentiated areas, or a colony with a completely contiguous tight border surrounded by a halo of differentiated cells (a "fried egg" morphology). 3=a colony with classic morphology; tight borders; free of differentiated cells, cells have low cytoplasmic: nuclei ratio.

Assign a "Tra1-60" score while visualizing each colony under fluorescence microscopy, according to the descriptions below: 0=no labeling; 1=weak or spotty; 2=heterogeneous or irregular labeling pattern; little or no evidence of a defined border; 3=uniform labeling with defined border.

Identify and Pick Tra1-60-Positive Colonies

Mark the plate with ink to identify colonies with the highest score. A score of "3-3" is ideal, however, there is precedence for picking and successfully propagating colonies with less than ideal morphology (e.g., those that might be scored as "2-3" or "2-2").

To pick colonies from a 6-well plate (or 10-cm dish), transfer the cells to a picking hood. While visualizing the colony with a dissecting microscope, manually draw a pipet tip across the surface of the dish (in a "tic tac toe board" fashion) around the colony border. This action should break the colony up into 3-6 pieces, freeing it from the surrounding MEFs. Draw the colony fragments into the pipet tip. (Note: Be aware that dislodged fragments that remain in the original well will likely re-attach and produce secondary colonies. This may confound your colony counts and estimates of reprogramming efficiency). Transfer the fragments directly into a recipient well of a 6 well plate containing MEFs with hES media+100 ng/ml zebrafish bFGF (growth media).

To pick colonies from 96-well format, identify wells with only a single colony with good morphology and Tra1-60 labeling scores. Aspirate the media from the wells. Add dispase and incubate for 7 minutes at 37° C. Dislodge the colony by gently pipetting up and down. Transfer the colony fragments in a 15 ml tube and dilute with hES media. Centrifuge at 350×g for 10 min. Aspirate the supernatant, then resuspend in growth media.

Transfer the fragments directly into a recipient well of a 6 well plate containing MEFs in growth media. The colony fragments should attach to the new MEF and form multiple new colonies. 24 hours later, replace the media with fresh growth media. Monitor the proliferation, and morphology for until the cells become confluent. Replace the media each day with fresh growth media.

Example 10

Materials

Materials used in Examples 1-9 are shown in Tables 5-7.

TABLE 5

Reagents

| Reagent | Supplier | Catalog Number |
|---|---|---|
| DMEM | Invitrogen | 11965 |
| DMEM/F12 | Invitrogen | 11330 |
| FBS | Hyclone | SH30070.03 |
| AIM-V | Invitrogen | 12055-091 |
| Pen/Strep/L-Glutamine | Invitrogen | 10378-016 |
| Opti-MEM | Invitrogen | 31985 |
| KOSR | Invitrogen | 10828 |
| NEAA | Invitrogen | 11140 |
| B-mercaptoethanol (BME) | Invitrogen | M7522 |

TABLE 5-continued

Reagents

| Reagent | Supplier | Catalog Number |
|---|---|---|
| L-glutamine | Invitrogen | 21051-024 |
| zbFGF | in house | none |
| rhIL2 | Peprotech | 200-02 |
| OKT3 (anti-CD3) Functional Grade | eBiosciences | 16-0037-81 |
| High density irradiated MEF for CM | Wi-Cell | none |
| Irradiated MEF | Wi-Cell | none |
| PBMCs via leukophoresis or freshly isolated blood sample | Biological Specialty Corporation | 213-14-04 |
| 1M HEPES | Invitrogen | 15630 |
| 0.05% Trypsin/EDTA | Invitrogen | 25300 |
| PBS (Ca and Mg free) | Invitrogen | 14190 |
| Gelatin | Sigma | C1890 |
| Trypan Blue Stain | Invitrogen | 15250-061 |
| PEI | Sigma | 03880 |
| 10 cm tissue culture plates | Falcon | 353003 |
| 6 well tissue culture plates | Nunc | 140685 |
| 250 ml media filters | Nunc | 568-002 |

TABLE 6

| D10F | | FACS Buffer | |
|---|---|---|---|
| DMEM | 90% | PBS (Ca and Mg free) | |
| FBS + or − | 10% | | 2% |
| HEPES | 50 mM | | (0.1% NaN3 optional) |

TABLE 7

| Conditioned Media (CM) | |
|---|---|
| DMEM/F12 | 80% |
| KOSR | 20% |
| NEAA | 1% |
| BME | 0.1 mM |
| L-glutamine | 1 mM |
| zbFGF | 100 ng/ml |

Expose to high density MEF culture. Collect medium daily, for 8-10 days. Add zbFGF only before using for IPS culture then filter.

Example 11

Generation of iPS Cells from CD34+ Hematopoietic Cells

PBMCs were isolated from leukopak or freshly drawn blood samples as described in Example 1. MACS separation for CD34+ cells was performed using a Indirect CD34 Micro-Bead Kit (Miltenyi Biotec, Bergisch Gladbach, Germany) or a Direct CD34 MicroBead Kit or a lineage depletion kit (Miltenyi Biotec, Bergisch Gladbach, Germany) according to manufacturers instructions. A fraction of the CD34+ MACS purified cells were collected for FACS analysis, and the remaining cells were replated in low attachment 6 well plates using CD34+ cell expansion media, below. The CD34+ cell enrichment can be performed using the CD34 direct microbeads or the indirect CD34 hapten antibody staining kit.

TABLE 8

CD34 Expansion Media

| CD34 Exp. Media | Concentration | Supplier | Cat# |
|---|---|---|---|
| Stem Pro-34 | 48 ml | Invitrogen | 10639-011 |
| Step Pro-34 Supp | 650 ul | Invitrogen | |
| Penn/Strep | 0.5 ml | Invitrogen | |
| L-Glut/BME | 0.5 ml | Invitrogen/Sigma | |
| IL3 | 20 ng/ml | Invitrogen | PHC0034 |
| Flt3L | 100 ng/ml | Invitrogen | PHC1705 |
| SCF | 100 ng/ml | Invitrogen | PHC2115 |

CD34+ cell expansion media: Stem Pro 34 (Invitrogen) is mixed the desired volume of nutrient supplement according to the Manufacturer's instructions. Stem Pro complete is supplemented with 100 ng/ml of recombinant Stem Cell Factor and recombinant 100 ng/ml of Flt-3 Ligand and 20 ng/ml of recombinant human interleukin-3 (IL-3). The medium is also supplemented with fresh 1% Glutamine and 1% Penicillin Streptomycin solution, All the supplements were mixed and the media was filtered before use.

Cells were seeded approximately 24 hours prior to transfection, via the method described above. 293T cells were also transfected for retrovirus production, and hematopoietic cells were then transfected with either (OCT4, SOX2, NANOG, and Lin28) or (OCT4, SOX2, KLF4, c-MYC) genes, delivered by MMLV retroviruses, as described above. As a result of these experiments, it was observed that CD34+ hematopoietic cells transfected with either set of the above genes resulted in the generation of new iPS cell lines.

The following protocol was used for reprogramming PBMCs using MMLV retroviruses: Place MACS LS separation column at −20° C. for quick cooling (Alternately the columns and MACs buffer can be cooled overnight at 4° C.). Thaw appropriate number of PBMC vials to collect ~3×10$^8$ cells. Bring cells up to 5 ml with MACS Buffer (keep buffer cold throughout procedure). Centrifuge at 1200 rpm×5 min, aspirate supernatant and resuspend in MACS Buffer. Count cells using hemacytometer. Divide cell suspension into 3 tubes of 1×10$^8$ and centrifuge 300×g for 10 minutes. The CD34+ cell enrichment can be performed using the CD34 direct microbeads or the indirect CD34 hapten antibody staining kit. Resuspend each cell pellet in 300 ul of MACS Buffer. Add 100 ul of FcR Blocking Reagent per tube, mix. Add 100 ul of CD34-Hapten-Antibody or direct CD34 beads per tube, mix. Incubate at 4° C. for 15 minutes. Wash cell with 5 ml of MACS Buffer and centrifuge 300×g for 10 minutes. Aspirate supernatant completely. Resuspend the cells in 500 ul of MACS Buffer. The cells are ready separation if using the one step CD34 direct microbeads. If using the indirect CD34 separation beads then there is one more incubation step with the anti-hapten micorbeads before separation. Add 100 ul of Anti-Hapten Microbeads, mix. Incubate at 4° C. for 15 minutes. Wash cells with 2 ml of MACS Buffer, centrifuge 300×g for 10 minutes. Resuspend in 500 ul MACS Buffer. Remove MACS LS Columns from 4° C. Place column on separator magnet. Rinse column with 3 ml of MACS Buffer. Apply cell suspension onto the column. Collect unlabeled cells that pass through and wash column with 3 ml of MACS Buffer. Repeat wash 2 additional times. Remove the column from the magnet and place in a suitable collection tube. Add 3 ml of MACS Buffer and collect enriched CD34+ cell fraction by flushing out the column with plunger provided. Collect a fraction of enriched population for FACS analysis. Replate the remaining cells in low attachment 6 well plate using CD34+ cell expansion media. When using the lineage Cell Depletion kit the cells are incubated with a biotinlylated cocktail of lineage positive antibodies (CD2, CD3, CD11b, CD14, CD15, CD16, CD19, CD56, CD123, CD235a) to remove mature hematopoietic cell types such as T cells, B cells, NK cells, dendritic cells, monocytes, granulocytes, erythroid cells. Following the incubation the cells are washed and incubated with anti-Biotin micro beads. The cell suspension is washed and separated manually column or by using the AutoMACs cell separator.

Identifying and Picking iPS colonies was done via the following method: Morphologically colonies were generally dense and comprised of small, compact cells with enlarged nuclei and 2 distinct nucleoli. Colonies are frequently too dense to observe such distinct features and appear to have differentiated material on the center of the colony. Borders of colony are usually defined. However, the blood iPS cells (BiPSCs) appeared more diffuse with shaggy boundaries, a feature not typically consistent with previous iPSCs derived from fibroblasts. Colonies will silence the GFP and RFP expressed from the integrated viral DNA. Some bona fide colonies will lose fluorescence by 20 days post infection and some have lost fluorescence after they have been picked and transferred ~35-40 days post-infection. All colonies should be lacking GFP and RFP expression (though some expression was noted in single cells nearby. To pick manually, a pipet tip was used to break it up colonies into 3-6 pieces to increase the probability of freeing stem cells from the surrounding MEF and hematopoietic stem cells. Picking was avoided until multiple colonies have formed so as to avoid confounding your counts of total colonies, i.e. to avoid the possibility that a small chunk of a colony resettles and could be falsely counted as a new clone. Cells were then transferred directly into a recipient well of a 6 well plate containing MEFs with hES media+100 ng/ml zebrafish bFGF. Proliferation, morphology, and loss of fluorescence were monitored for 1-2 weeks to be confident that clones are indeed fully reprogrammed. Cells were fed daily. After the picked and plated colonies adhere and display characteristic ES-like morphology, colonies were manually picked as described above again onto a new set of 6 well MEF plates, with daily feeding. As wells become confluent, passage as normal iPSC line with collagenase, freeze down aliquots at various passages, and test thaw each set.

The colonies that are picked and expanded are stained for the presence of pluripotency markers (SSEA-4, Oct3/4, Tra-160, Tra-181). The colonies were also stained for the presence of alkaline phosphatase activity. The clones were tested for the presence of a normal karyotype and the identity of the iPS clones was confirmed to the parental cell type by FISH analysis. The results of these tests indicated that $CD34^+$ cells had been successfully converted into iPS cells. It was observed that, although the efficiency of the transfection was higher when $CD34^+$ cells were transfected with (Sox2, Oct4, c-Myc, and Klf-4), iPS cells derived from the transfection of $CD34^+$ cells with (Sox2, Oct4, Nanog, and Lin28) factors were observed to be more stable during maintenance of clones on irradiated MEFs and Matrigel. In further experiments, $CD34^+$ cells obtained from leukopak and donor blood were successfully converted into iPS cells via transfection with (Sox2, Oct4, c-Myc, and Klf-4). The reprogramming efficiency of the progenitor cell type was observed to be approximately 10 colonies per 100,000 cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 4,684,611
U.S. Pat. No. 4,952,500
U.S. Pat. No. 5,302,523
U.S. Pat. No. 5,322,783
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,624
U.S. Patent Publn. 20030211603
U.S. Patent Publn. 20070238170
U.S. Patent Publn. 20080038820
U.S. Patent Publn. 20080226558
U.S. Patent Publn. 20080254003
U.S. Patent Publn. 20090047739
U.S. Patent Ser. No. 61/058,858
U.S. Patent Ser. No. 61/088,054
U.S. Patent Ser. No. 61/156,304
U.S. Patent Ser. No. 61/172,079
Aasen et al., *Nat. Biotechnol.*, 26:1276-1284, 2008.
Akkina et al., *J. Virol.* 70:2581-2585, 1996.
Alexander et al., *Proc. Nat. Acad. Sci. USA*, 85:5092-5096, 1988.
Almquist et al., *Med. Chem.*, 23(12):1392-1398, 1980.
Andrews et al., In: *Teratocarcinomas and Embryonic Stem Cells*, Robertson (Ed.), IRL Press, 207-246, 1987.
Ausubel et al., Current Protocols in Molecular Biology, Greene Publishing Associates and Wiley Interscience, N.Y., 1994.
Berger et al., *Blood*, 101:476-484, 2003.
Biswas et al., *Annals NY Acad. Sci.*, 590:582-583, 1990.
Biswas, et al., *J. Clin. Microbiol.*, 29:2228-2233, 1991.
Bode et al., *Gene Ther. Mol. Biol.*, 6:33-46, 2001.

Boland et al., *Nature*. Aug. 2, 2009. [Epub ahead of print]
Boyer et al., *Cell*, 122(6):947-56, 2005.
Carbonelli et al., *FEMS Microbiol. Lett.*, 177(1):75-82, 1999.
Chadwick et al., *Blood*, 102(3):906-15, 2003.
Chambers et al., *Cell*, 113(5):643-55, 2003.
Chandler et al., *Proc. Natl. Acad. Sci. USA*, 94(8):3596-601, 1997.
Chatenoud, *Curr. Opin. Immunol.*, 17:632-637, 2005.
Chen and Okayama, *Mol. Cell Biol.*, 7(8):2745-2752, 1987.
Choi et al., *Stem Cells*, 27(3):559-67, 2009.
Christ et al., *Haematologica* 92(9):1165-72, 2007.
Cocea, *Biotechniques*, 23(5):814-816, 1997.
Ebert et al., *Nature*, 457:277-280, 2009.
Eminli et al., *Nat. Genet.*, 41:968-976, 2009.
EP 45665
EPO 0273085
Ercolani et al., *J. Biol. Chem.*, 263:15335-15341, 1988.
Evans, et al., In: *Cancer Principles and Practice of Oncology*, Devita et al. (Eds.), Lippincot-Raven, NY, 1054-1087, 1997.
Fechheimer et al., *Proc Natl. Acad. Sci. USA*, 84:8463-8467, 1987.
Fraley et al., *Proc. Natl. Acad. Sci. USA*, 76:3348-3352, 1979.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gopal, *Mol. Cell Biol.*, 5:1188-1190, 1985.
Graham and Van Der Eb, *Virology*, 52:456-467, 1973.
Gratwohl et al., *Blood*, 100:2374-2386, 2002.
Guo et al. *Stem Cells*. 21(1):15-20, 2003.
Hanna et al., *Cell*, 133:250-264, 2008.
Harland and Weintraub, *J. Cell Biol.*, 101(3):1094-1099, 1985.
Hess et al. *Blood*, 104(6): 1648-55, 2004.
Hong et al., *Nature*, 460:1132-1135, 2009.
Johnson et al., *Blood*, 114:535-546, 2009.
Kadaja-Saarepuu et al. *Oncogene*, 27(12):1705-15, 2008.
Kaeppler et al., *Plant Cell Reports*, 9:415-418, 1990.
Kaji et al., *Nature*, 458, 771-775, 2009.
Kaneda et al., *Science*, 243:375-378, 1989.
Karanu et al. *Leukemia* 17, 1366-1374.
Karin et al. *Cell*, 36:371-379, 1989
Kato et al, *J. Biol. Chem.*, 266:3361-3364, 1991.
Kawamura et al., *Nature*, 460:1140-1144, 2009.
Kim et al., *J. Virol.*, 66:3879-3882, 1992.
Kleeberger et al., *Clin. Diagn. Lab Immunol.*, 6:14-19, 1999.
Klein et al., *Nature*, 327:70-73, 1987.
Ladi et al., *Nature Immunology*, 7: 338-343, 2006.
Langle-Rouault et al., *J. Virol.*, 72(7):6181-6185, 1998.
Levenson et al., *Hum. Gene Ther.*, 9(8):1233-1236, 1998.
Levitskaya et al., *Proc. Natl. Acad. Sci. USA*, 94(23):12616-12621, 1997.
Li et al., *Nature*, 460:1136-1139, 2009.
Lichtman and Williams, In: *Williams hematology*. McGraw-Hill Medical Pub. Division. 1 (various pagings), NY, 2006.
Loh et al., *Blood*, 113:5476-5479, 2009.
Ludwig et al., *Nat. Biotechnol.*, 24(2):185-187, 2006b.
Ludwig et al., *Nat. Methods*, 3(8):637-46, 2006a.
Ludwig et al., *Nat. Methods*, 3:637-646, 2006.
Macejak and Sarnow, *Nature*, 353:90-94, 1991.
Maherali and Hochedlinger, *Cell Stem Cell*, 3: 595-605, 2008.
Maniatis, et al., Molecular Cloning, A Laboratory Manual, Cold Spring Harbor Press, Cold Spring Harbor, N.Y., 1988.
Marion et al., *Nature*, 460:1149-1153, 2009.
Meuer et al., *Cell*, 36:897-906, 1984.
Mitchell et al., *PLoS Biol.*, 2:E234, 2004.
Morgan et al., *Science*, 314:126-129, 2006.
Nabel et al., *Science*, 244(4910):1342-1344, 1989.
Narazaki et al., *Circulation*, 118(5): 498-506, 2008.
Ng et al., *Blood*, 106(5): 1601-1603, 2005.
Ng et al., *Nuc. Acids Res.*, 17:601-615, 1989.
Nicolau and Sene, *Biochim. Biophys. Acta*, 721:185-190, 1982.
Nicolau et al., *Methods Enzymol.*, 149:157-176, 1987.
Omirulleh et al., *Plant Mol. Biol.*, 21(3):415-428, 1993.
O'Shea et al., *Proc. Natl. Acad. Sci. USA*, 89:10306, 1992.
PCT Appln. WO 94/09699
PCT Appln. WO 94/09699
PCT Appln. WO 95/03408
PCT Appln. WO 95/06128
PCT Appln. WO 99/20741
Scymczak et al., *Nat. Biotechnol.*, 22(5):589-94, 2004.
Ryan et al., *Biochemistry*, 36(42):12802-12813, 1997.
De Felipe, *Prog. Brain Res.*, 136:215-38, 2002.
Pelletier and Sonenberg, *Nature*, 334(6180):320-325, 1988.
Perales et al., *Proc. Natl. Acad. Sci. USA*, 91:4086-4090, 1994.
Potrykus et al., *Mol. Gen. Genet.*, 199(2):169-177, 1985.
Potter et al., *Proc. Natl. Acad. Sci. USA*, 81:7161-7165, 1984.
Quitsche et al., *J. Biol. Chem.*, 264: 9539-9545, 1989.
Richards et al., *Cell*, 37:263-272, 1984.
Rippe, et al., *Mol. Cell Biol.*, 10:689-695, 1990.
Sambrook and Russell, Molecular Cloning: A Laboratory Manual, 3rd Edition, Cold Spring Harbor Laboratory, N.Y., 1989.
Takahashi et al., *Cell*, 126(4):663-676, 2006.
Takahashi et al., *Cell*, 126(4):663-76, 2007a.
Takahashi et al., *Cell*, 131:861-872, 2007.
Thomson et al., *Science*, 282:1145-1147, 1998.
Tur-Kaspa et al., *Mol. Cell Biol.*, 6:716-718, 1986.
Utikal et al., *Nature*, 460:1145-1148, 2009.
van Dongen et al., *Leukemia*, 17:2257-2317, 2003.
van Lent et al., *J. Immunol.*, 179:4959-4968, 2007.
Vodyanik et al., *Blood*, 108(6):2095-2105, 2006.
Wagner et al., *Proc. Natl. Acad. Sci. USA* 87(9):3410-3414, 1990.
Wang et al., *Nature Biotechnology*, 25 (3): 317-318, 2007
Wilson et al., *Nature Reviews Immunology*, 9: 91-105, 2009.
Wilson et al., *Science*, 244:1344-1346, 1989.
Woltjen et al., *Nature*, 458, 766-770, 2009.
Wong et al., *Gene*, 10:87-94, 1980.
Wu and Wu, *Adv. Drug Delivery Rev.*, 12:159-167, 1993.
Wu and Wu, *Biochemistry*, 27: 887-892, 1988.
Wu and Wu, *J. Biol. Chem.*, 262:4429-4432, 1987.
Wynn, *Nature Immunology*, 6:1069-1070, 2005.
Yamanaka et al., *Cell*, 131(5):861-72, 2007.
Yang and Russell, *Proc. Natl. Acad. Sci. USA*, 87:4144-4148, 1990.
Ye et al., *Blood*, 114(27):5473-80, 2009.
Yu et al., *Science*, 318:1917-1920, 2007.
Yu et al., *Science*, 324(5928):797-801, 2009.
Zhang et al., *Nat. Biotechnol.*, 19:1129-1133, 2001.
Zhang, et al., *Circ Res.*, 104(4):e30-41, 2009.
Zhou, et al., *Cell Stem Cell*, 4 (5):381-4, 2009.

The invention claimed is:
1. A method for producing human induced pluripotent stem cells from $CD34^+$ hematopoietic progenitor cells comprising the steps of:
    (a) obtaining a cell population comprising human $CD34^+$ hematopoietic progenitor cells, wherein the $CD34^+$ hematopoietic progenitor cells are from a subject whose cells have not been mobilized; and

(b) producing iPS cells from the CD34+ hematopoietic progenitor cells of the cell population through the introduction of nucleic acids encoding reprogramming factors selected from Oct4, Sox2, cMyc, Klf4, Nanog and Lin28, the nucleic acids being comprised in one or more episomal vectors, and culturing the cells under defined, feeder-free conditions to provide a human iPS cell population that is essentially free of integrated, exogenous viral elements.

2. The method of claim 1, wherein the source of the cell population is a blood sample, blood components, bone marrow, lymph node, fetal liver, or umbilical cord.

3. The method of claim 2, wherein the source of the cell population is a blood sample of from about 1 to about 5 ml.

4. The method of claim 3, wherein the source of the cell population is a blood sample of about 3 ml.

5. The method of claim 1, wherein the cell population has been cryopreserved.

6. The method of claim 1, wherein the cell population CD34+ hematopoietic progenitor cells is cultured in vitro with one or more cytokines to expand the T cell or CD34+ hematopoietic progenitor cells population therein.

7. The method of claim 6, wherein the one or more cytokines comprises at least one of SCF, Flt3L, or IL-3.

8. The method of claim 1, wherein the reprogramming factors are encoded on one or more expression cassettes that comprise at least one polycistronic transcript unit.

9. The method of claim 8, wherein the polycistronic transcript unit comprises at least two reprogramming genes.

10. The method of claim 8, wherein the polycistronic transcript unit comprises a reprogramming gene and a selectable or screenable marker.

11. The method of claim 1, wherein producing iPS cells from the CD34+ hematopoietic progenitor cells of the population further comprises selecting the iPS cells for one or more characteristics of embryonic stem cells.

12. The method of claim 11, wherein the characteristic is an adherent property, an undifferentiated morphology, an embryonic stem cell-specific marker or pluripotency.

13. The method of claim 12, wherein the characteristic is an adherent property.

14. The method of claim 12, wherein the characteristic is an undifferentiated morphology.

15. The method of claim 1, wherein the method further comprises differentiating the iPS cells to a differentiated cell.

16. The method of claim 15, wherein the differentiated cell comprises a cardiomyocyte, a hematopoietic cell, a neuron, a fibroblast or an epidermal cell.

\* \* \* \* \*

UNITED STATES PATENT AND TRADEMARK OFFICE
CERTIFICATE OF CORRECTION

PATENT NO. : 8,741,648 B2
APPLICATION NO. : 13/376361
DATED : June 3, 2014
INVENTOR(S) : Deepika Rajesh and Amanda Mack Page 1 of 1

It is certified that error appears in the above-identified patent and that said Letters Patent is hereby corrected as shown below:

On the Title page, item (56) References Cited - Other Publications, delete the 10th reference on page 1 "Bode et aL., "The hitchhiking principle: Optimizing episomal vectors for the use in gene therapy and biotechnology" *Gene Ther. Mol. Biol.*, 6:33-46, 2001." and insert --Bode et al., "The hitchhiking principle: Optimizing episomal vectors for the use in gene therapy and biotechnology," *Gene Ther. Mol. Biol.*, 6:33-46, 2001.-- therefor.

On the Title page, item (56) References Cited - Other Publications, delete the 3rd reference on page 2 "Loh et al., "Reprogramming ofT cells from human peripheral blood," *Cell Stem Cell*, 7:15-19, 2010." and insert --Loh et al., "Reprogramming of T cells from human peripheral blood," *Cell Stem Cell*, 7:15-19, 2010.-- therefor.

In the Claims

In claim 6, column 71, lines 19-22, delete "6. The method of claim 1, wherein the cell population $CD34^+$ hematopoietic progenitor cells is cultured in vitro with one or more cytokines to expand the T cell or $CD34^+$ hematopoietic progenitor cells population therein." and insert --6. The method of claim 1, wherein the cell population comprising $CD34^+$ hematopoietic progenitor cells is cultured in vitro with one or more cytokines to expand the $CD34^+$ hematopoietic progenitor cells therein.-- therefor.

Signed and Sealed this
Ninth Day of September, 2014

Michelle K. Lee
*Deputy Director of the United States Patent and Trademark Office*